(12) United States Patent
Inoue et al.

(10) Patent No.: US 9,406,894 B2
(45) Date of Patent: Aug. 2, 2016

(54) ORGANOMETALLIC COMPLEX, ORGANIC LIGHT-EMITTING ELEMENT, LIGHT-EMITTING DEVICE, ELECTRONIC DEVICE, AND LIGHTING DEVICE

(75) Inventors: Hideko Inoue, Kanagawa (JP); Tomoka Nakagawa, Kanagawa (JP); Satoshi Seo, Kanagawa (JP); Nobuharu Ohsawa, Tochigi (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 409 days.

(21) Appl. No.: 13/486,260

(22) Filed: Jun. 1, 2012

(65) Prior Publication Data

US 2012/0305896 A1 Dec. 6, 2012

(30) Foreign Application Priority Data

Jun. 3, 2011 (JP) .................................. 2011-125640

(51) Int. Cl.
*H01L 51/54* (2006.01)
*C09K 11/06* (2006.01)
*H01L 51/00* (2006.01)
*C07F 15/00* (2006.01)
*H01L 51/50* (2006.01)

(52) U.S. Cl.
CPC ........ *H01L 51/0085* (2013.01); *C07F 15/0033* (2013.01); *C09K 11/06* (2013.01); *H01L 51/009* (2013.01); *H01L 51/0067* (2013.01); *C09K 2211/1059* (2013.01); *C09K 2211/185* (2013.01); *H01L 51/0072* (2013.01); *H01L 51/5012* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 8,673,459 B2 | 3/2014 | Seo et al. | |
| 8,758,903 B2 | 6/2014 | Sugita et al. | |
| 9,005,770 B2 | 4/2015 | Taka et al. | |
| 2006/0008670 A1* | 1/2006 | Lin et al. ............. | C07D 231/12 428/690 |
| 2006/0036097 A1 | 2/2006 | Qiu et al. | |
| 2007/0085073 A1 | 4/2007 | Inoue et al. | |
| 2009/0102370 A1* | 4/2009 | Taka et al. ..................... | 313/504 |
| 2011/0101854 A1 | 5/2011 | Inoue et al. | |
| 2011/0198988 A1 | 8/2011 | Inoue et al. | |
| 2011/0220882 A1 | 9/2011 | Inoue et al. | |
| 2012/0133273 A1 | 5/2012 | Inoue et al. | |
| 2012/0205645 A1 | 8/2012 | Fuchs et al. | |

FOREIGN PATENT DOCUMENTS

| | | |
|---|---|---|
| EP | 1 777 229 A1 | 4/2007 |
| EP | 1 953 843 A1 | 8/2008 |
| JP | 2006-60198 | 3/2006 |
| JP | 2007-137872 | 6/2007 |
| JP | 2007-208102 | 8/2007 |
| JP | 2007-284408 A | 11/2007 |
| JP | 2008-69221 | 3/2008 |
| JP | 2008-69268 A * | 3/2008 |
| JP | 2009-046601 A | 3/2009 |
| JP | 2009-130094 A | 6/2009 |
| JP | 2011-253980 A * | 12/2011 |
| WO | WO 2005/123873 A1 | 12/2005 |
| WO | WO 2007/052431 A1 | 5/2007 |
| WO | WO 2008/035664 A1 | 3/2008 |
| WO | WO 2009/107497 A1 | 9/2009 |
| WO | WO 2011/051404 A1 | 5/2011 |

OTHER PUBLICATIONS

Machine translation of JP 2008-69268 A (Mar. 2008).*
Machine translation of JP 2011-253980 A (Dec. 2011).*
Van Diemen, J.H. et al., "Synthesis and Characterization of Orthometalated Rhodium (III) Complexes Containing Substituted Triazoles," Inorganic Chemistry, vol. 30, No. 21, 1991, pp. 4038-4043, American Chemical Society.
Zamora, F. et al., "Synthesis of Several Palladium Complexes Derived from 2,5-diphenyl-1,3,4-Oxadiazole. Reactivity Against Nucleobase Models,", Journal of Inorganic Biochemistry, vol. 68, No. 4, Dec. 1, 1997, pp. 257-263.
Baldo, M.A. et al., "Very High-Efficiency Green Organic Light-Emitting Devices Based on Electrophosphorescence," Applied Physics Letters, vol. 75, No. 1, Jul. 5, 1999, pp. 4-6.

(Continued)

*Primary Examiner* — Marie R. Yamnitzky
(74) *Attorney, Agent, or Firm* — Husch Blackwell LLP

(57) ABSTRACT

A novel and highly reliable organometallic complex which has an emission region in the wavelength band of blue to yellow is provided. A light-emitting element using the organometallic complex, a light-emitting device, an electronic device, and a lighting device each using the light-emitting element are provided. An organometallic complex including a structure represented by General Formula (G1) is provided. The organometallic complex including the structure represented by General Formula (G1) is a novel and highly reliable organometallic complex which has an emission region in the wavelength band of blue to yellow. In addition, a light-emitting element using the organometallic complex, a light-emitting device, an electronic device, and a lighting device each including the light-emitting element are provided.

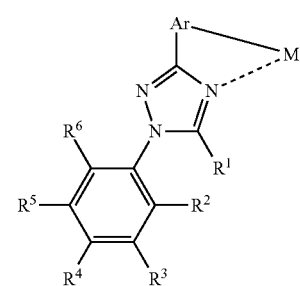

(G1)

52 Claims, 30 Drawing Sheets

(56) References Cited

OTHER PUBLICATIONS

Liu, J. et al., "Green-Yellow Electrophosphorescence from di [2,5-diphenyl-1,3,4-oxadiazole $C^{2'}$, $N^3$] Platinum( II ) Doped PVK Devices," Chinese Physics Letters, vol. 22, No. 3, pp. 2005, 723-726.

Wu, Z.L. et al., "Synthesis and Photoluminescence of a Novel Iridium Complex (BuPhOXD)2Ir(acac) with Unit of 1,3,4-Oxadiazole," Chinese Chemical Letters, vol. 16, No. 2, 2005, pp. 241-244.

Chen, L. et al., "Synthesis, Structure, Electrochemistry, Photophysics and Electroluminescence of 1,3,4-Oxadiazole-Based Ortho-Metalated Iridium(III) Complexes,", Journal of Organometallic Chemistry, vol. 691, No. 16, Aug. 1, 2006, pp. 3519-3530.

Lo, S.-C. et al, "Blue Phosphorescence from Iridium(III) Complexes at Room Temperature," Chemistry of Materials, vol. 18, No. 21, 2006, pp. 5119-5129, American Chemical Society.

"4 Oxidation by Other Oxidizing Agents," *Experimental Chemistry 17 Synthesis of Organic Compounds V—Oxidation Reaction*—5th edition, Jul. 30, 2004, p. 122, Maruzen Co., Ltd.

\* cited by examiner

ORGANOMETALLIC COMPLEX, ORGANIC LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to an organic light-emitting element and an organometallic complex. In particular, the present invention relates to an organometallic complex that is capable of converting triplet excited energy into luminescence. In addition, the present invention relates to a light-emitting element, a light-emitting device, an electronic device, and a lighting device each using the organometallic complex.

2. Description of the Related Art

In recent years, a light-emitting element using a light-emitting organic compound or inorganic compound as a light-emitting material has been actively developed. In particular, a light-emitting element called an EL (electroluminescence) element has attracted attention as a next-generation flat panel display element because it has a simple structure in which a light-emitting layer containing a light-emitting material is provided between electrodes, and characteristics such as feasibility of being thinner and more lightweight and responsive to input signals and capability of driving with direct current at a low voltage. In addition, a display using such a light-emitting element has a feature that it is excellent in contrast and image quality, and has a wide viewing angle. Further, since such a light-emitting element is a plane light source, the light-emitting element is considered to be applicable to a light source such as a backlight of a liquid crystal display and lighting.

In the case where the light-emitting substance is an organic compound having a light-emitting property, the emission mechanism of the light-emitting element is a carrier-injection type. That is, by applying a voltage with a light-emitting layer interposed between electrodes, electrons and holes injected from electrodes recombine to make the light-emitting substance excited, and light is emitted when the excited state returns to a ground state. There are two types of the excited states which are possible: a singlet excited state (S*) and a triplet excited state (T*). In addition, the statistical generation ratio thereof in a light-emitting element is considered to be S*:T*=1:3.

In general, the ground state of a light-emitting organic compound is a singlet state. Light emission from a singlet excited state (S*) is referred to as fluorescence where electron transition occurs between the same multiplicities. On the other hand, light emission from a triplet excited state (T*) is referred to as phosphorescence where electron transition occurs between different multiplicities. Here, in a compound emitting fluorescence (hereinafter referred to as fluorescent compound), in general, phosphorescence is not observed at room temperature, and only fluorescence is observed. Accordingly, the internal quantum efficiency (the ratio of generated photons to injected carriers) in a light-emitting element using a fluorescent compound is assumed to have a theoretical limit of 25% based on S*:T*=1:3.

On the other hand, the use of a phosphorescent compound can increase the internal quantum efficiency to 100% in theory. In other words, emission efficiency can be 4 times as much as that of the fluorescence compound. Therefore, the light-emitting element using a phosphorescent compound has been actively developed in recent years in order to achieve a highly efficient light-emitting element.

In particular, an organometallic complex in which iridium or the like is a central metal has attracted attention as a phosphorescent compound owing to its high phosphorescence quantum yield. As a typical phosphorescent material emitting green to blue light, there is a metal complex in which iridium (Ir) is a central metal (hereinafter referred to as "Ir complex") (for example, see Patent Document 1, Patent document 2, and Patent Document 3). Disclosed in Patent Document 1 is an Ir complex where a triazole derivative is a ligand.

REFERENCE

Patent Document

[Patent Document 1] Japanese Published Patent Application No. 2007-137872
[Patent Document 2] Japanese Published Patent Application No. 2008-069221
[Patent Document 3] PCT International Publication No. 2008-035664

SUMMARY OF THE INVENTION

As reported in Patent Documents 1 to 3, although phosphorescent materials emitting green or blue light have been developed, there is room for improvement in terms of emission efficiency, reliability, light-emitting characteristics, synthesis yield, cost, or the like, and further development is required for obtaining more excellent phosphorescent materials.

In view of the above problems, it is an object of one embodiment of the present invention to provide a novel substance that can emit phosphorescence in a wavelength band of blue to yellow. It is another object of one embodiment of the present invention to provide a novel substance that emits phosphorescence in a wavelength band of blue to yellow and has high emission efficiency. It is another object of one embodiment of the present invention to provide a novel substance that emits phosphorescence in a wavelength band of blue to yellow and has high reliability.

It is another object to provide a light-emitting element that emits light in a wavelength band of blue to yellow by using such a novel substance. Moreover, it is another object to provide a light-emitting device, an electronic device, and a lighting device each using the light-emitting element.

The present inventors have found that an organometallic complex in which nitrogen at the 4-position of a 1-phenyl-3-aryl-1H-1,2,4-triazole derivative is coordinated to a Group 9 metal or a Group 10 metal and the aryl group is bonded to the Group 9 metal or the Group 10 metal emits phosphorescence. Specifically, the present inventors have found that a tris-type organometallic complex which includes three 1-phenyl-3-aryl-1H-1,2,4-triazole derivatives in each of which nitrogen at the 4-position of the 1-phenyl-3-aryl-1H-1,2,4-triazole derivative is coordinated to iridium and the aryl group is bonded to the iridium emits blue phosphorescence with extremely high color purity.

Further, the present inventors have found that a light-emitting element including, between a pair of electrodes, an organometallic complex in which nitrogen at the 4-position of a 1-phenyl-3-aryl-1H-1,2,4-triazole derivative is coordinated to a Group 9 metal or a Group 10 metal and the aryl group is bonded to the Group 9 metal or the Group 10 metal emits phosphorescence highly efficiently by application of voltage. Specifically, the present inventors have found that a light-emitting element including, between a pair of electrode, a tris-type organometallic complex which includes three 1-phenyl-3-aryl-1H-1,2,4-triazole derivatives in each of which nitrogen at the 4-position of the 1-phenyl-3-aryl-1H-1,2,4-triazole derivative is coordinated to iridium and the aryl group is bonded to the iridium emits blue phosphorescence with extremely high color purity highly efficiently by application of voltage.

Thus, one embodiment of the present invention is an organometallic complex in which a 1H-1,2,4-triazole derivative is a ligand and a Group 9 element or a Group 10 element is a central metal. Specifically, one embodiment of the present invention is an organometallic complex including a structure represented by General Formula (G1). Note that an organometallic complex including the structure represented by General Formula (G1) can emit phosphorescence and thus can be advantageously applied to a light-emitting layer of a light-emitting element. Accordingly, a preferable mode of the present invention is a phosphorescent organometallic complex including the structure represented by General Formula (G1). In particular, an organometallic complex which includes the structure represented by General Formula (G1) and in which the lowest triplet excited state is formed in the structure is preferable because the organometallic complex can efficiently exhibit phosphorescence.

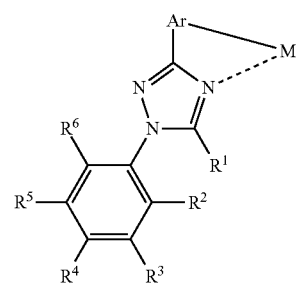

(G1)

Moreover, an organometallic complex in which only a 1H-1,2,4-triazole derivative is a ligand and a Group 9 element or a Group 10 element is a central metal emits blue phosphorescence with extremely high color purity highly efficiently. Thus, another embodiment of the present invention is an organometallic complex represented by General Formula (G2).

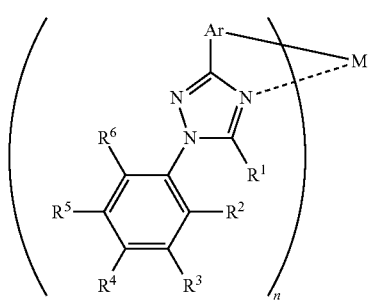

(G2)

A further embodiment of the present invention is an organometallic complex represented by General Formula (G3).

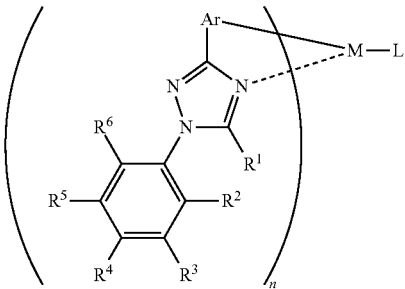

(G3)

In each of General Formulae (G1), (G2), and (G3), Ar represents an arylene group having 6 to 13 carbon atoms which may have a substituent. $R^1$ represents hydrogen or an alkyl group having 1 to 4 carbon atoms, and $R^2$ to $R^6$ separately represent any of hydrogen, an alkyl group having 1 to 4 carbon atoms, and a substituted or unsubstituted phenyl group. M is a central metal and represents a Group 9 element or a Group 10 element.

In addition, in General Formula (G2), n is 3 when the central metal M is a Group 9 element, and n is 2 when the central metal M is a Group 10 element.

In General Formula (G3), L represents a monoanionic bidentate ligand. Moreover, n is 2 when the central metal M is a Group 9 element, and n is 1 when the central metal M is a Group 10 element.

Specific examples of Ar include a phenylene group, a phenylene group substituted by one or more alkyl groups, a phenylene group substituted by one or more alkoxy groups, a phenylene group substituted by one or more alkylthio groups, a phenylene group substituted by one or more haloalkyl groups, a phenylene group substituted by one or more halogen groups, a phenylene group substituted by one or more phenyl groups, a biphenyl-diyl group, a naphthalene-diyl group, a fluorene-diyl group, a 9,9-dialkylfluorene-diyl group, and a 9,9-diarylfluorene-diyl group.

Specific examples of $R^1$ include hydrogen, a methyl group, an ethyl group, a propyl group, and an isopropyl group.

Further, specific examples of the alkyl group having 1 to 4 carbon atoms in $R^2$ to $R^6$ include a methyl group, an ethyl group, a propyl group, an isopropyl group, a butyl group, a sec-butyl group, an isobutyl group, a tert-butyl group, a phenyl group substituted by one or more alkyl groups, a phenyl group substituted by one or more alkoxy group groups, a phenyl group substituted by one or more alkylthio groups, a phenyl group substituted by one or more haloalkyl groups, and a phenyl group substituted by one or more halogen groups.

In addition, at least one of $R^2$ to $R^6$ preferably includes a substituent in which case generation of an organometallic complex in which a central metal is ortho-metalated by $R^2$ or $R^6$ can be suppressed and the synthesis yield is drastically improved.

M is a central metal and represents a Group 9 element or a Group 10 element; the Group 9 element is preferably iridium and the Group 10 element is preferably platinum. In terms of a heavy atom effect, a heavy metal is preferably used as the central metal of the organometallic complex in order to more efficiently emit phosphorescence.

Note that when the metal M is iridium, the spin-orbit interaction is increased. In addition, since the metal M and a ligand have metal-carbon bonding, charge is likely to be transferred to a 1H-1,2,4-triazole ring which is the ligand (this transfer is also called triplet metal to ligand charge transfer (triplet MLCT)). As a result, a forbidden transition such as phosphorescence is likely to occur and the triplet excitation lifetime decreases, so that there is an effect of increasing the emission efficiency of the phosphorescent organometallic complex, which is preferable.

Thus, a still further embodiment of the present invention is an organometallic complex including a structure represented by General Formula (G4).

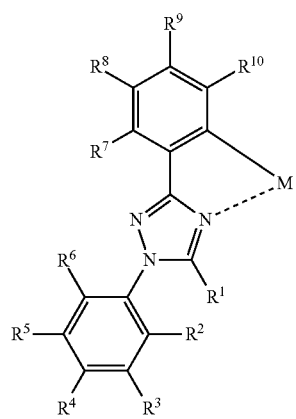

(G4)

Moreover, an organometallic complex in which only a 1H-1,2,4-triazole derivative is a ligand and a Group 9 element or a Group 10 element is a central metal emits blue phosphorescence with extremely high color purity highly efficiently. Thus, a yet still further embodiment of the present invention is an organometallic complex represented by General Formula (G5).

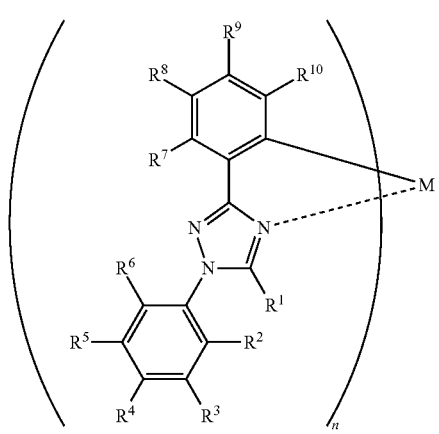

(G5)

A yet still further embodiment of the present invention is an organometallic complex represented by General Formula (G6).

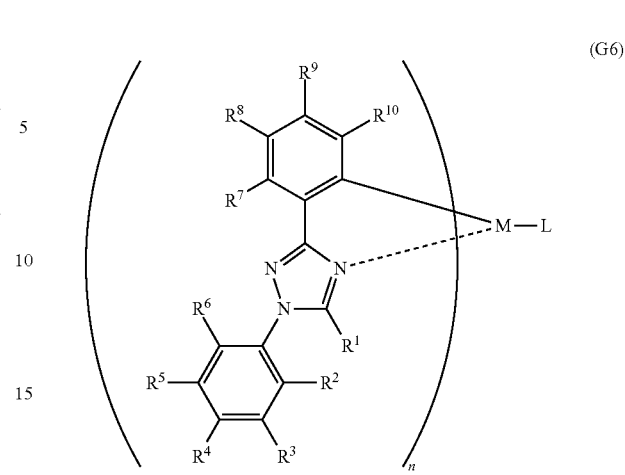

(G6)

In each of General Formulae (G4), (G5), and (G6), $R^1$ represents hydrogen or an alkyl group having 1 to 4 carbon atoms, and $R^2$ to $R^6$ separately represent any of hydrogen, an alkyl group having 1 to 4 carbon atoms, and a substituted or unsubstituted phenyl group. Further, $R^7$ to $R^{10}$ separately represent any of hydrogen, an alkyl group having 1 to 4 carbon atoms, an alkoxy group having 1 to 4 carbon atoms, an alkylthio group having 1 to 4 carbon atoms, a haloalkyl group having 1 to 4 carbon atoms, a halogen group, and a phenyl group. M is a central metal and represents a Group 9 element or a Group 10 element.

In addition, in General Formula (G5), n is 3 when the central metal M is a Group 9 element, and n is 2 when the central metal M is a Group 10 element.

In General Formula (G6), L represents a monoanionic bidentate ligand. Moreover, n is 2 when the central metal M is a Group 9 element, and n is 1 when the central metal M is a Group 10 element.

Here, specific examples of $R^1$ to $R^6$ can be the same as those of $R^1$ to $R^6$ in General Formulae (G1), (G2), and (G3).

Specific examples of $R^7$ to $R^{10}$ are a methyl group, an ethyl group, a propyl group, an isopropyl group, a butyl group, a sec-butyl group, an isobutyl group, a tert-butyl group, a methoxy group, an ethoxy group, a propoxy group, an isopropoxy group, a butoxy group, a sec-butoxy group, an isobutoxy group, a tert-butoxy group, a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a fluoro group, a fluoromethyl group, a difluoromethyl group, a trifluoromethyl group, a chloro group, a chloromethyl group, a dichloromethyl group, a trichloromethyl group, a bromomethyl group, a 2,2,2-trifluoroethyl group, a 3,3,3-trifluoropropyl group, a 1,1,1,3,3,3-hexafluoroisopropyl group, and the like.

Another embodiment of the present invention is a light-emitting element containing, between a pair of electrodes, any of the organometallic complexes described above. In particular, any organometallic complex described above is preferably contained in a light-emitting layer.

A light-emitting device, an electronic device, and a lighting device each using the above light-emitting element also belong to the category of the present invention. Note that the light-emitting device in this specification includes, in its category, an image display device, a light-emitting device, and a light source. In addition, the light-emitting device includes, in its category, all of a module in which a connector such as a flexible printed circuit (FPC), a tape automated bonding (TAB) tape or a tape carrier package (TCP) is connected to a panel, a module in which a printed wiring board is provided on the tip of a TAB tape or a TCP, and a module in which an integrated circuit (IC) is directly mounted on a light-emitting element by a chip on glass (COG) method.

According to one embodiment of the present invention, a novel organometallic complex that has an emission region in the wavelength band of blue to yellow and high emission efficiency can be provided.

According to another embodiment of the present invention, a novel organometallic complex that has an emission region in the wavelength band of blue to yellow and high reliability can be provided.

According to another embodiment of the present invention, a light-emitting element using the organometallic complex, and a light-emitting device, an electronic device, and a lighting device each using the light-emitting element can be provided.

DETAILED DESCRIPTION OF THE INVENTION

Figure 1:
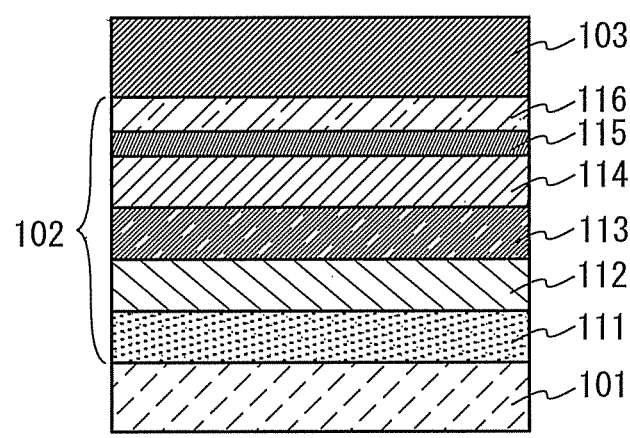
FIG. 1 illustrates a light-emitting element of one embodiment of the present invention.

Embodiments will now be described with reference to drawings in detail. Note that the invention is not limited to the following description, and it will be easily understood by those skilled in the art that various changes and modifications can be made without departing from the spirit and scope of the invention. Therefore, the invention should not be construed as being limited to the description in the following embodiments. Note that in the structures of the invention described below, the same portions or portions having similar functions are denoted by the same reference numerals in different drawings, and description of such portions is not repeated.

(Embodiment 1)

In Embodiment 1, an organometallic complex of one embodiment of the present invention is described.

One embodiment of the present invention is an organometallic complex in which a 1H-1,2,4-triazole derivative is a ligand and a Group 9 element or a Group 10 element is a central metal. Specifically, one embodiment of the present invention is any of an organometallic complex including a structure represented by General Formula (G1), an organometallic complex represented by General Formula (G2), and an organometallic complex represented by General Formula (G3).

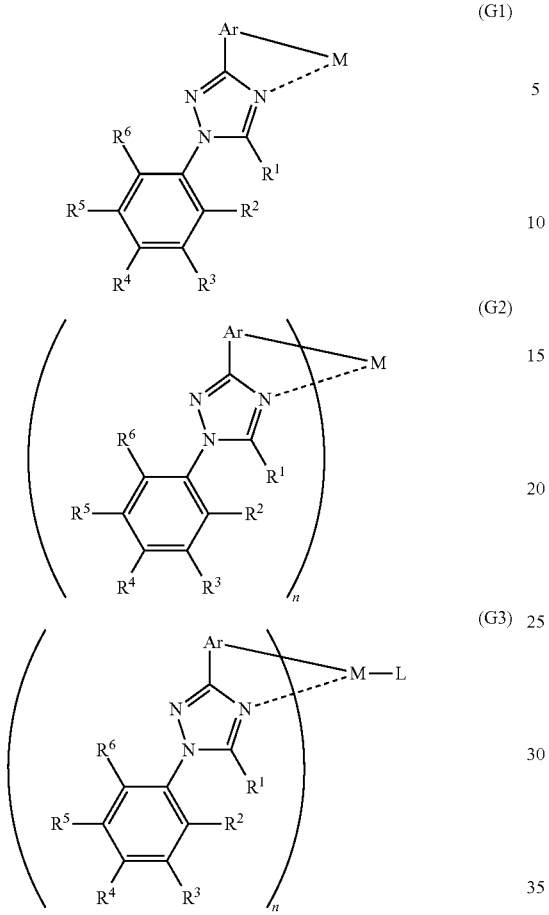

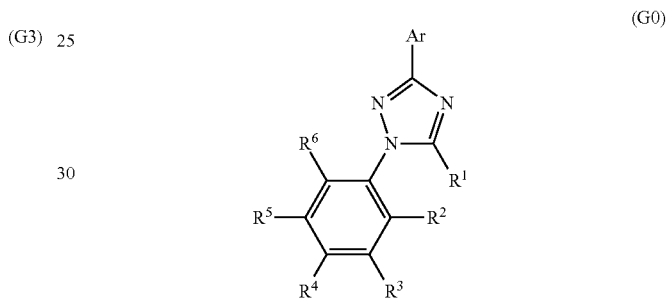

In each of General Formulae (G1), (G2), and (G3), Ar represents an arylene group having 6 to 13 carbon atoms which may have a substituent. $R^1$ represents hydrogen or an alkyl group having 1 to 4 carbon atoms, and $R^2$ to $R^6$ separately represent any of hydrogen, an alkyl group having 1 to 4 carbon atoms, and a substituted or unsubstituted phenyl group. M is a central metal and represents a Group 9 element or a Group 10 element.

In addition, in General Formula (G2), n is 3 when the central metal M is a Group 9 element, and n is 2 when the central metal M is a Group 10 element.

Further, in General Formula (G3), L represents a monoanionic bidentate ligand. Moreover, n is 2 when the central metal M is a Group 9 element, and n is 1 when the central metal M is a Group 10 element.

Note that an organometallic complex including the structure represented by General Formula (G1) can emit phosphorescence and thus can be advantageously applied to a light-emitting layer of a light-emitting element. Accordingly, a preferable mode of the present invention is a phosphorescent organometallic complex including the structure represented by General Formula (G1).

In particular, an organometallic complex which includes the structure represented by General Formula (G1) and in which the lowest triplet excited state is formed in the structure is preferable because the organometallic complex can efficiently exhibit phosphorescence. To obtain such a mode, another skeleton (another ligand) which is included in the organometallic complex can be selected such that the lowest triplet excitation energy of the structure is equal to or lower than the lowest triplet excitation energy of the another skeleton (the another ligand), for example. In that case, regardless of what a skeleton (ligand) other than the structure is, the lowest triplet excited state is formed in the structure at last, so that phosphorescence originating from the structure is thus obtained. Therefore, phosphorescence can be highly efficiently obtained. For example, vinyl polymer having the structure as a side chain can be given.

Here, examples of methods of synthesizing an organometallic complex including the structure represented by General Formula (G1), an organometallic complex represented by General Formula (G2), and an organometallic complex represented by General Formula (G3) are described.

<Method of Synthesizing a 1H-1,2,4-triazole Derivative Represented by General Formula (G0)>

First, an example of a method of synthesizing a 1H-1,2,4-triazole derivative represented by General Formula (G0) below is described.

First, an example of a method of synthesizing a 1H-1,2,4-triazole derivative represented by General Formula (G0) below is described.

In General Formula (G0), Ar represents an arylene group having 6 to 13 carbon atoms which may have a substituent. $R^1$ represents hydrogen or an alkyl group having 1 to 4 carbon atoms, and $R^2$ to $R^6$ separately represent any of hydrogen, an alkyl group having 1 to 4 carbon atoms, and a substituted or unsubstituted phenyl group.

As shown in a scheme (a) below, an acylamidine compound (A1) and a hydrazine compound (A2) react with each other, so that a 1H-1,2,4-triazole derivative can be obtained. Note that Z in the formula represents a group (a leaving group) that is detached through a ring closure reaction, such as an alkoxy group, an alkylthio group, an amino group, or a cyano group.

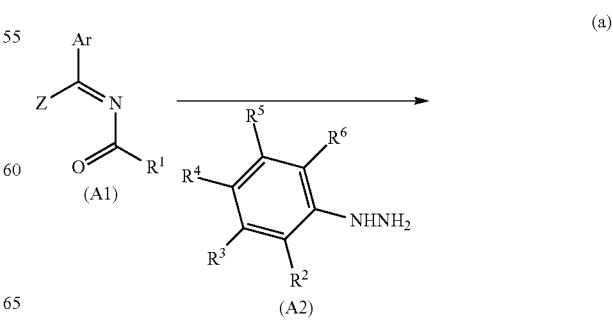

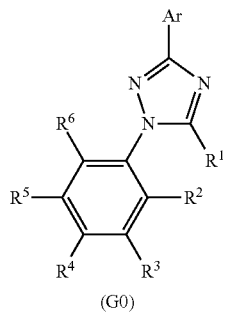

(G0)

In the scheme (a), Ar represents an arylene group having 6 to 13 carbon atoms which may have a substituent. $R^1$ represents hydrogen or an alkyl group having 1 to 4 carbon atoms, and $R^2$ to $R^6$ separately represent any of hydrogen, an alkyl group having 1 to 4 carbon atoms, and a substituted or unsubstituted phenyl group.

Note that the method of synthesizing a 1H-1,2,4-triazole derivative is not limited to the scheme (a). For example, there is also a method in which a 1,3,4-oxadiazole derivative and arylamine are heated.

As described above, a 1H-1,2,4-triazole derivative represented by General Formula (G0) can be synthesized by a simple synthesis scheme.

Note that various kinds of the above-described compounds (A1) and (A2) are commercially available or can be synthesized. For example, the acylamidine compound (A1) can be synthesized by making alkanoyl chloride and aryl imino ether react with each other; in this case, the leaving group Z is an alkoxyl group. In this manner, various types of the 1H-1,2,4-triazole derivative represented by General Formula (G0) can be synthesized. Thus, an organometallic complex of one embodiment of the present invention which includes the structure represented by General Formula (G1) features abundant variations in ligands. By using such an organometallic complex having wide variations of a ligand in manufacture of a light-emitting element, fine adjustment of element characteristics required for the light-emitting element can be performed easily.

<Method of Synthesizing an Organometallic Complex of One Embodiment of the Present Invention, Represented by General Formula (G2)>

The organometallic complex of one embodiment of the invention, represented by General Formula (G2), can be synthesized by a synthesis scheme (b) below. That is, the 1H-1,2,4-triazole derivative represented by General Formula (G0) is mixed with a metal compound of a Group 9 or Group 10 element which contains a halogen (e.g., rhodium chloride hydrate, palladium chloride, iridium chloride, iridium bromide, iridium iodide, or potassium tetrachloroplatinate) or with an organometallic complex compound of a Group 9 or Group 10 element (e.g., an acetylacetonate complex or a diethylsulfide complex) and the mixture is then heated, so that the organometallic complex represented by General Formula (G2) can be obtained.

Further, this heating process may be performed after the 1H-1,2,4-triazole derivative represented by General Formula (G0) and the metal compound of a Group 9 or Group 10 element which contains a halogen or the organometallic complex compound of a Group 9 or Group 10 element are dissolved in an alcohol-based solvent (e.g., glycerol, ethylene glycol, 2-methoxyethanol, or 2-ethoxyethanol). There is no particular limitation on a heating means, and an oil bath, a sand bath, or an aluminum block may be used. Alternatively, microwaves can be used as a heating means.

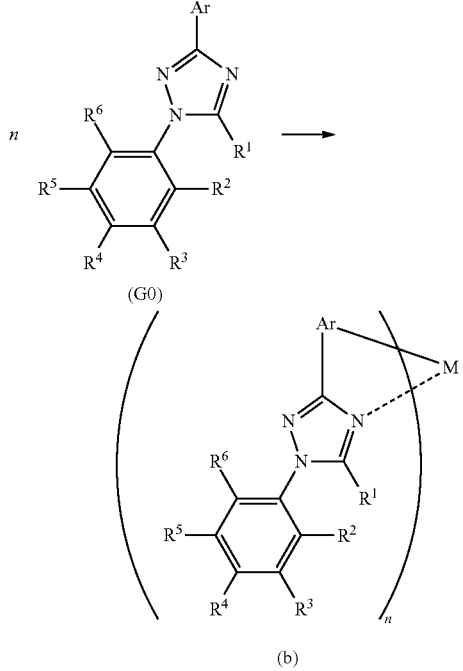

(b)

In the scheme (b), Ar represents an arylene group having 6 to 13 carbon atoms which may have a substituent. $R^1$ represents hydrogen or an alkyl group having 1 to 4 carbon atoms, and $R^2$ to $R^6$ separately represent any of hydrogen, an alkyl group having 1 to 4 carbon atoms, and a substituted or unsubstituted phenyl group. M is a central metal and represents a Group 9 element or a Group 10 element. In addition, n is 3 when the central metal M is a Group 9 element, and n is 2 when the central metal M is a Group 10 element.

Note that the method of synthesizing the organometallic complex of one embodiment of the present invention which is represented by General Formula (G2) is not limited to the scheme (b). For example, there is also a method in which a halogen-bridged dinuclear complex (B) illustrated in the following scheme (c) and the 1H-1,2,4-triazole derivative represented by General Formula (G0) are heated. In that case, a silver salt such as silver trifluoroacetate or silver trifluoromethylsulfonate may be added to enhance the reaction.

<Method of Synthesizing an Organometallic Complex of One Embodiment of the Present Invention, Represented by General Formula (G3)>

The organometallic complex of one embodiment of the invention, represented by General Formula (G3), can be synthesized by the synthesis scheme (c) below. That is, the 1H-1,2,4-triazole derivative represented by General Formula (G0) and a metal compound of a Group 9 or Group 10 element which contains a halogen (e.g., rhodium chloride hydrate, palladium chloride, iridium chloride, iridium bromide, iridium iodide, or potassium tetrachloroplatinate) are heated in an inert gas atmosphere by using no solvent, an alcohol-based solvent (e.g., glycerol, ethylene glycol, 2-methoxyethanol, or 2-ethoxyethanol) alone, or a mixed solvent of water and one or more of the alcohol-based solvents, whereby the dinuclear complex (B), which is one type of an organometallic complex including a halogen-bridged structure and is a novel substance, can be obtained. There is no particular limitation on a heating means, and an oil bath, a sand bath, or an aluminum block may be used. Alternatively, microwaves can be used as a heating means.

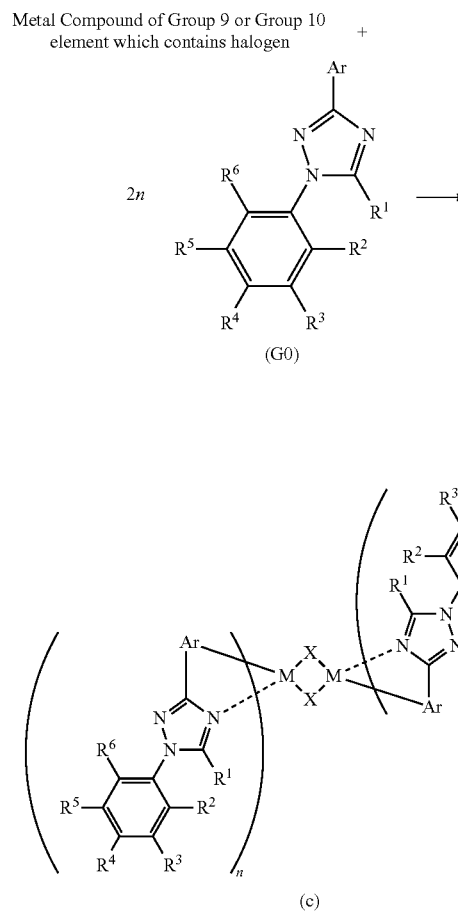

In the synthesis scheme (c), X represents a halogen, and Ar represents an arylene group having 6 to 13 carbon atoms which may have a substituent. $R^1$ represents hydrogen or an alkyl group having 1 to 4 carbon atoms, and $R^2$ to $R^6$ separately represent any of hydrogen, an alkyl group having 1 to 4 carbon atoms, and a substituted or unsubstituted phenyl group. M represents a Group 9 element or a Group 10 element. In addition, n is 2 when M is a Group 9 element, and n is 1 when M is a Group 10 element.

Furthermore, as shown in a synthesis scheme (d) below, the dinuclear complex (B) obtained in the synthesis scheme (c) above is reacted with HL which is a material of a monoanionic ligand in an inert gas atmosphere, whereby a proton of HL is separated and L coordinates to the central metal M. Thus, the organometallic complex of one embodiment of the present invention which is represented by General Formula (G3) can be obtained. There is no particular limitation on a heating means, and an oil bath, a sand bath, or an aluminum block may be used. Alternatively, microwaves can be used as a heating means.

In the synthesis scheme (d), L represents a monoanionic bidentate ligand, X represents a halogen, and Ar represents an arylene group having 6 to 13 carbon atoms which may have a substituent. $R^1$ represents hydrogen or an alkyl group having 1 to 4 carbon atoms, and $R^2$ to $R^6$ separately represent any of hydrogen, an alkyl group having 1 to 4 carbon atoms, and a substituted or unsubstituted phenyl group. M represents a Group 9 element or a Group 10 element. In addition, n is 2 when M is a Group 9 element, and n is 1 when M is a Group 10 element.

Note that examples of a monoanionic bidentate ligand include a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen; specifically, ligands represented by Structural Formulae (L1) to (L6) below can be given.

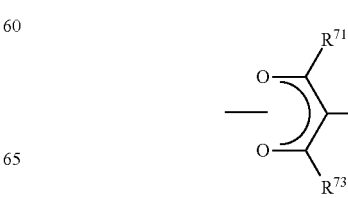

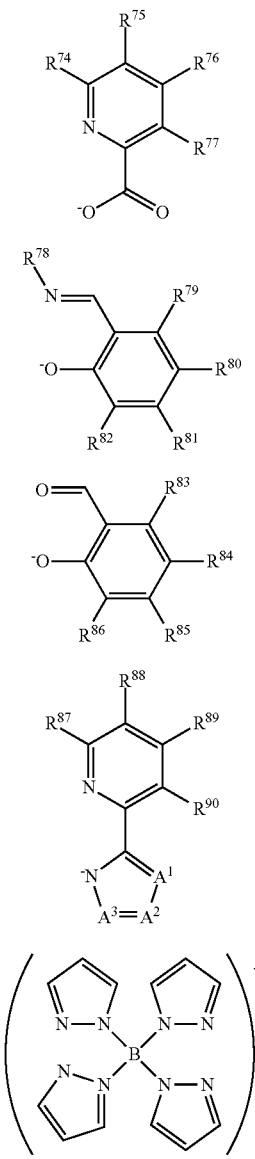

(L2)

(L3)

(L4)

(L5)

(L6)

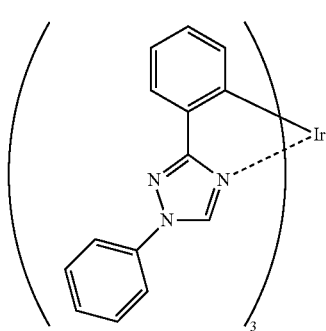

(100)

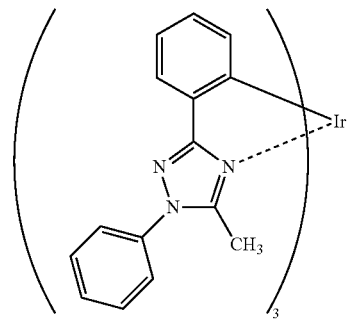

(101)

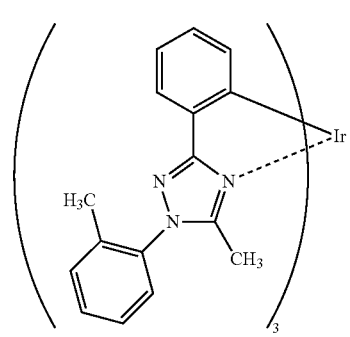

(102)

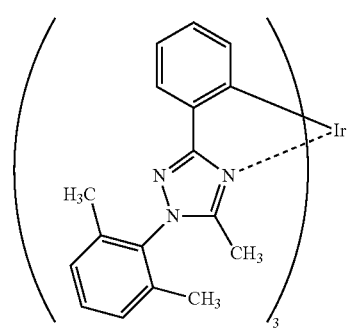

(103)

In Structural Formulae (L1) to (L6), $R^{71}$ to $R^{90}$ separately represent any of hydrogen, an alkyl group having 1 to 4 carbon atoms, a halogen group, a haloalkyl group, an alkoxy group having 1 to 4 carbon atoms, and an alkylthio group having 1 to 4 carbon atoms. In addition, $A^1$, $A^2$, and $A^3$ separately represent nitrogen N or carbon C—R. R represents hydrogen, an alkyl group having 1 to 4 carbon atoms, a halogen group, a haloalkyl group having 1 to 4 carbon atoms, or a phenyl group.

Although examples of the synthesis methods are described above, organometallic complexes which are disclosed embodiments of the present invention may be synthesized by any other synthesis method.

As specific examples of organometallic complexes including the structures represented by General Formulae (G1) to (G3), organometallic complexes represented by Structural Formulae (100) to (135) can be given. Note that the present invention is not limited to the organometallic complexes represented by these structural formulae.

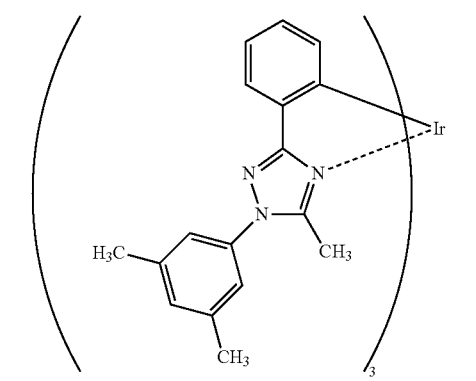
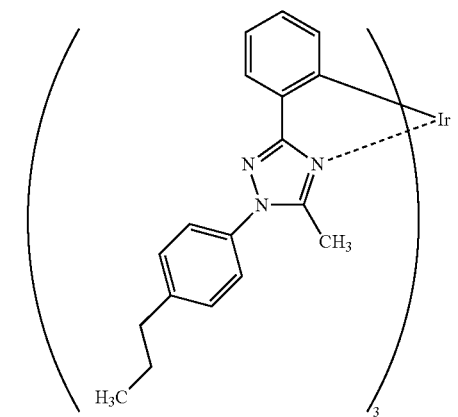
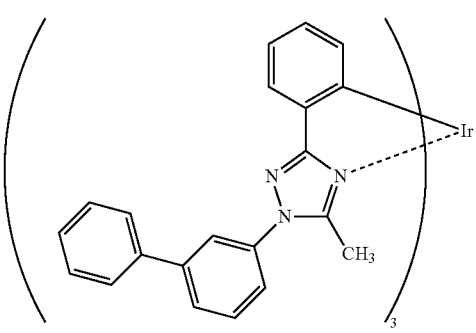
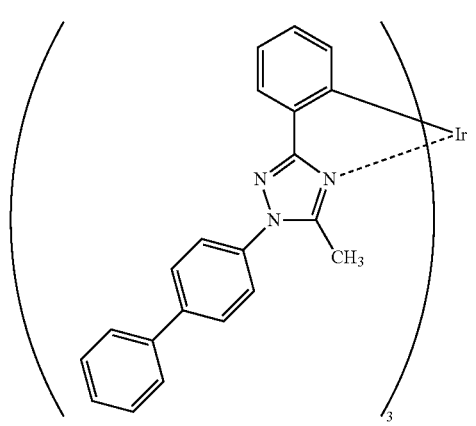
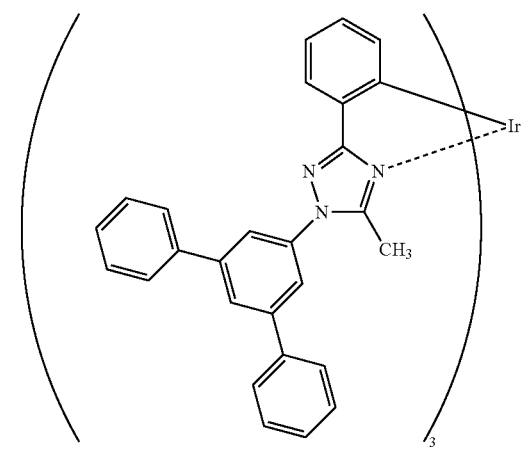
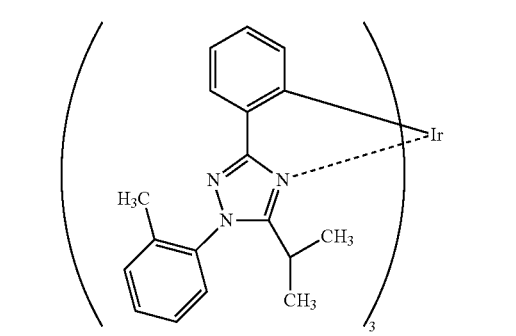
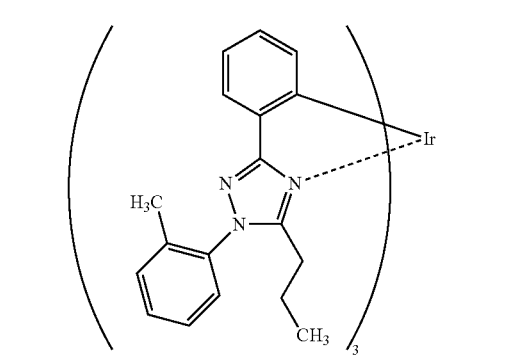
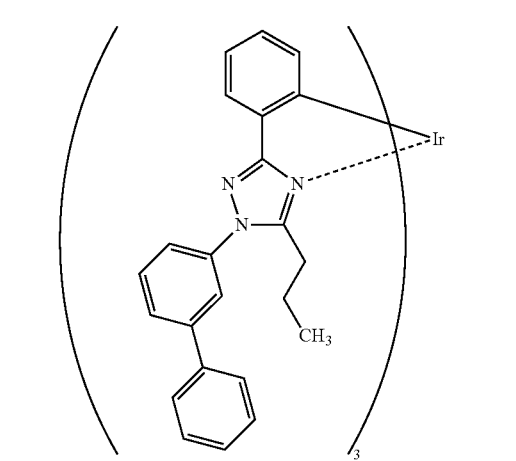

(112) 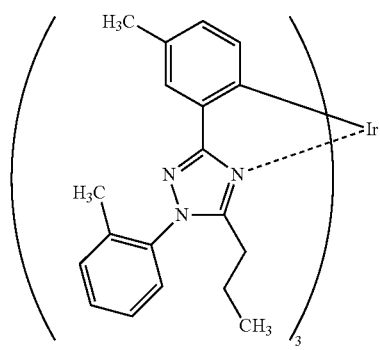
(113) 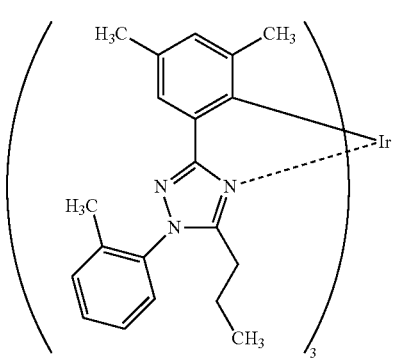
(114) 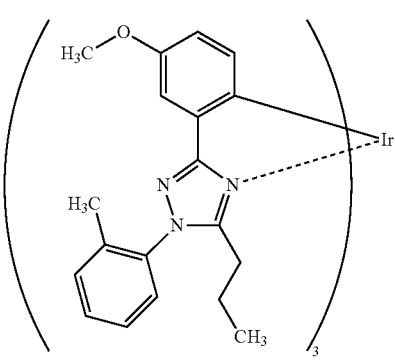
(115) 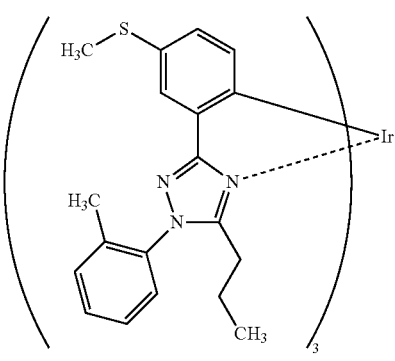
(116) 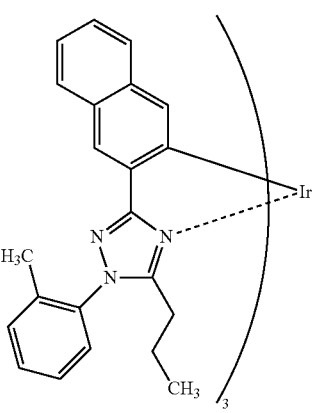
(117) 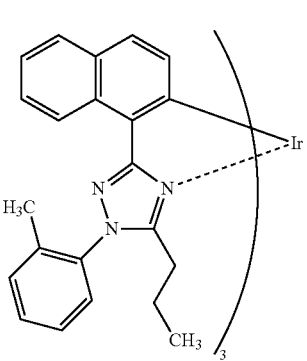
(118) 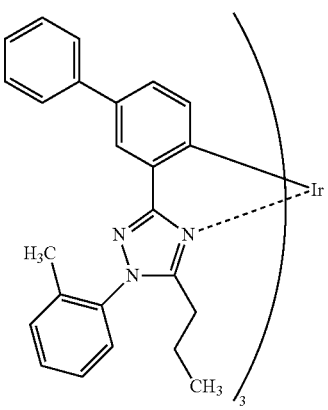
(119) 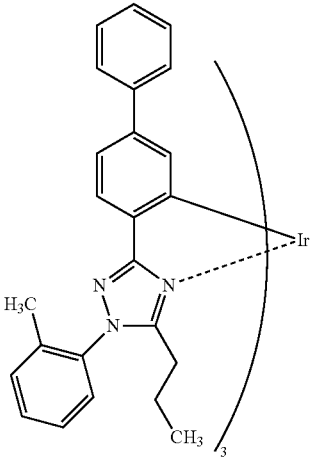

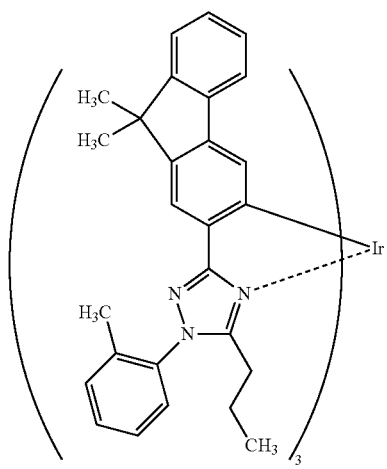
(120)
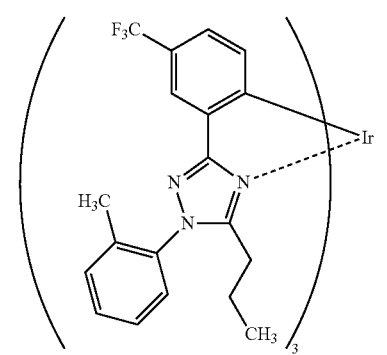
(121)
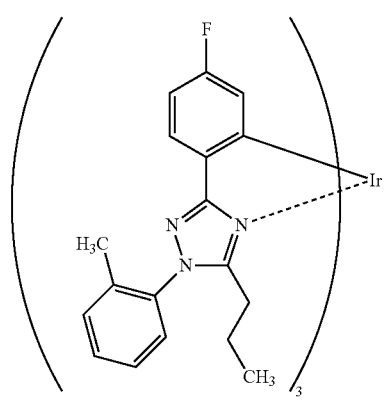
(122)
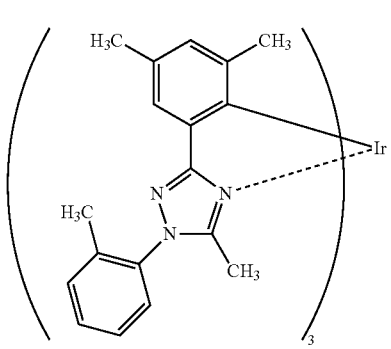
(123)
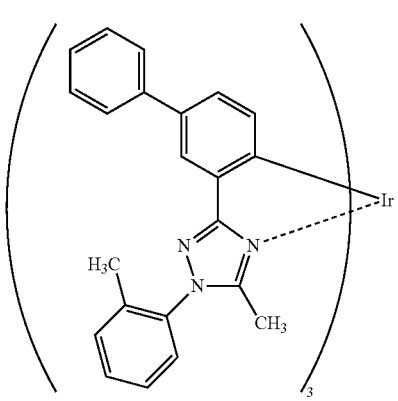
(124)
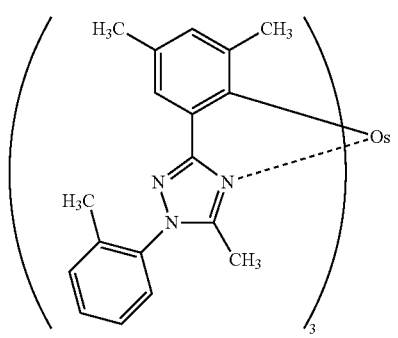
(125)
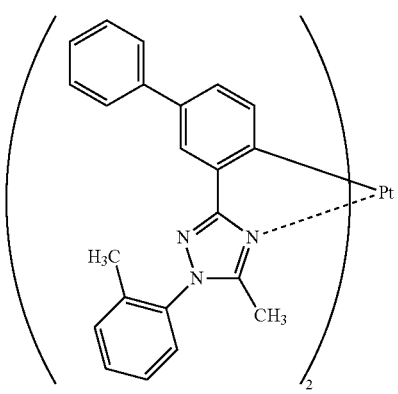
(126)
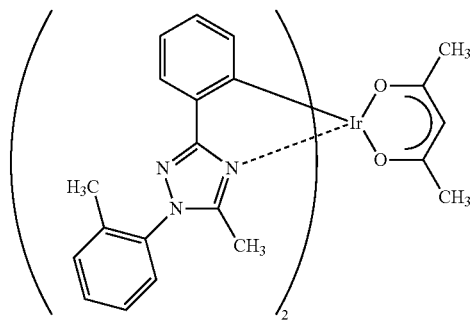
(127)

(128)
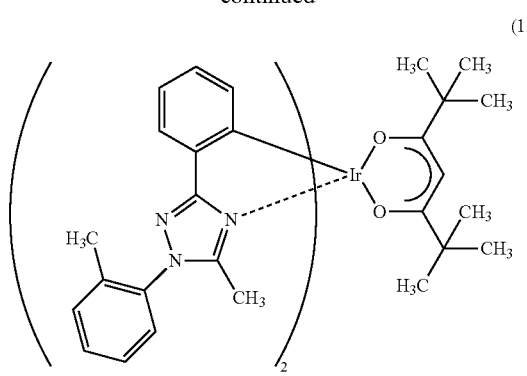

(129)
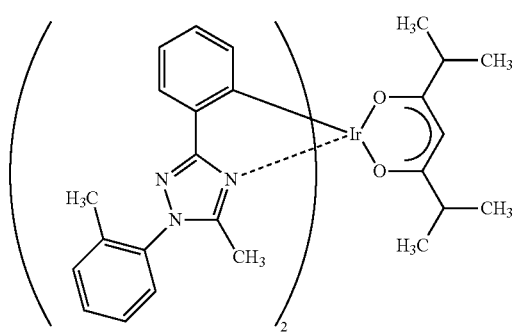

(130)
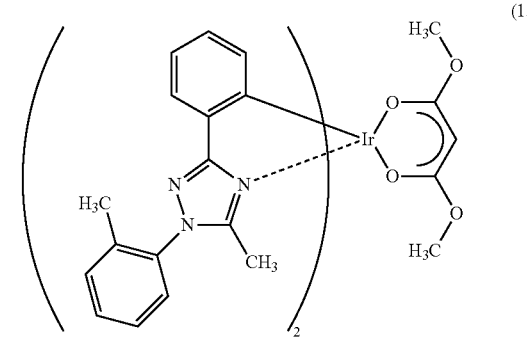

(131)
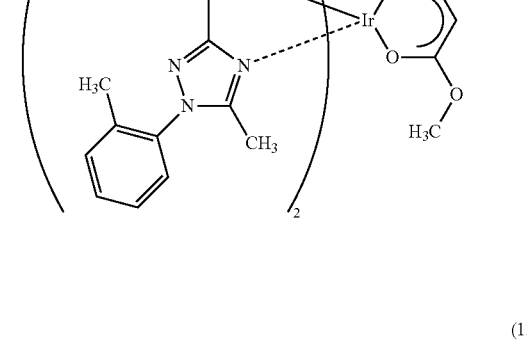

(132)
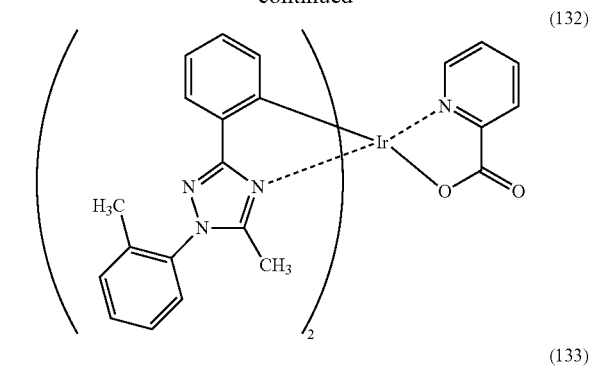

(133)
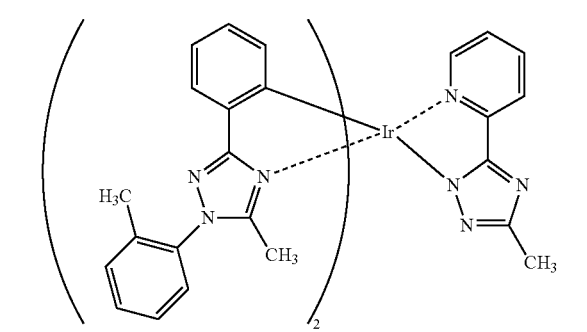

(134)
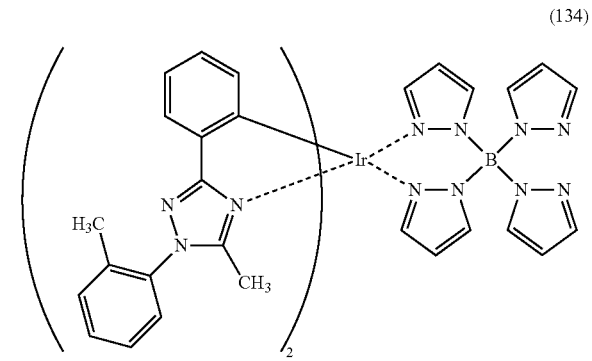

(135)
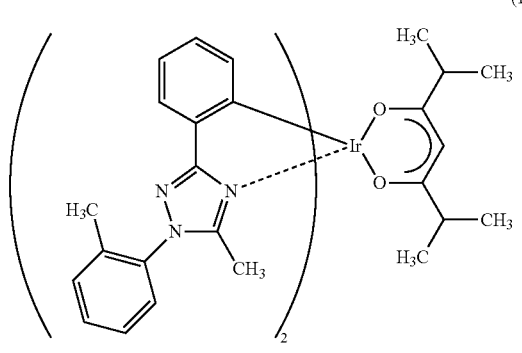

Depending on the type of the ligand, there can be stereoisomers of the organometallic complexes represented by Structural Formulae (100) to (135) above, and such isomers are included in the category of an organometallic complex of one embodiment of the present invention.

The above-described organometallic complexes each of which is one embodiment of the present invention are novel substances capable of emitting phosphorescence.

This embodiment can be implemented in appropriate combination with the other embodiments.

(Embodiment 2)

In this embodiment, a light-emitting element using the organometallic complex in which a 1H-1,2,4-triazole derivative is a ligand and which is described in Embodiment 1 as one embodiment of the present invention is described. Specifically, a light-emitting element in which the organometallic complex is used for a light-emitting layer is described with reference to FIG. 1.

In a light-emitting element described in this embodiment, as illustrated in FIG. 1, an EL layer 102 including a light-emitting layer 113 is provided between a pair of electrodes (a first electrode 101 and a second electrode 103), and the EL layer 102 includes a hole-injection layer 111, a hole-transport layer 112, an electron-transport layer 114, an electron-injection layer 115, a charge-generation layer 116, and the like in addition to the light-emitting layer 113.

In this embodiment, the first electrode 101 functions as an anode, and the second electrode 103 functions as a cathode.

By application of a voltage to such a light-emitting element, holes injected from the first electrode 101 side and electrons injected from the second electrode 103 side recombine in the light-emitting layer 113 to raise the organometallic complex to an excited state. Then, light is emitted when the organometallic complex in the excited state returns to the ground state. Thus, the organometallic complex of one embodiment of the present invention functions as a light-emitting substance in the light-emitting element.

The hole-injection layer 111 included in the EL layer 102 is a layer containing a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge-generation layer 116 is a layer containing a substance having a high hole-transport property and an acceptor substance. Owing to the acceptor substance, electrons are extracted from the substance having a high hole-transport property and the extracted electrons are injected from the electron-injection layer 115 having an electron-injection property into the light-emitting layer 113 through the electron-transport layer 114.

A specific example in which the light-emitting element described in this embodiment is manufactured is described.

As the first electrode 101 and the second electrode 103, a metal, an alloy, an electrically conductive compound, a mixture thereof, and the like can be used. Specifically, indium oxide-tin oxide (ITO: indium tin oxide), indium oxide-tin oxide containing silicon or silicon oxide, indium oxide-zinc oxide, indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg, AlLi), a rare earth metal such as europium (Eu) or ytterbium (Yb), an alloy containing such an element, graphene, and the like can be used. The first electrode 101 and the second electrode 103 can be formed by, for example, a sputtering method, an evaporation method (including a vacuum evaporation method), or the like.

As the substance having a high hole-transport property used for the hole-injection layer 111, the hole-transport layer 112, and the charge-generation layer 116, the following can be given, for example: aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1',1'-biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like. In addition, the following carbazole derivatives and the like can be used: 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances mentioned here are mainly ones that have a hole mobility of $10^{-6}$ cm$^2$/Vs or higher. However, substances other than the above-described ones may also be used as long as the substances have hole-transport properties higher than electron-transport properties.

Further, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can be used.

As examples of the acceptor substance that is used for the hole-injection layer 111 and the charge-generation layer 116, a transition metal oxide or an oxide of a metal belonging to any of Group 4 to Group 8 of the periodic table can be given. Specifically, molybdenum oxide is particularly preferable.

The light-emitting layer 113 contains the organometallic complex described in Embodiment 1 as a guest material serving as a light-emitting substance and a substance that has higher triplet excitation energy than this organometallic complex as a host material.

Preferable examples of the substance (i.e., host material) used for dispersing any of the above-described organometallic complexes include: any of compounds having an arylamine skeleton, such as 2,3-bis(4-diphenylaminophenyl)quinoxaline (abbreviation: TPAQn) and NPB, carbazole derivatives such as CBP and 4,4',4"-tris(carbazol-9-yl)triphenylamine (abbreviation: TCTA), and metal complexes such as bis[2-(2-hydroxyphenyl)pyridinato] zinc (abbreviation: Znpp$_2$), bis[2-(2-hydroxyphenyl)benzoxazolato] zinc (abbreviation: Zn(BOX)$_2$), bis(2-methyl-8-quinolinolato)(4-phenylphenolato)aluminum (abbreviation: BAlq), and tris(8-quinolinolato)aluminum (abbreviation: Alq$_3$). Alternatively, a high molecular compound such as PVK can be used.

Note that in the case where the light-emitting layer 113 contains the above-described organometallic complex (guest material) and the host material, phosphorescence with high emission efficiency can be obtained from the light-emitting layer 113.

The electron-transport layer 114 is a layer containing a substance having a high electron-transport property. For the electron-transport layer 114, metal complexes such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)benzothiazolato]zinc (abbreviation: Zn(BTZ)$_2$) can be used. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can be used. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances described here are mainly ones having an electron mobility of $10^{-6}$ cm$^2$/Vs or higher. Note that other than these substances, any substance that has a property of transporting more holes than electrons may be used for the electron-transport layer.

Further, the electron-transport layer 114 is not limited to a single layer, and a stacked layer in which two or more layers containing any of the above-described substances are stacked may be used.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiOx), can be used. Alternatively, a rare earth metal compound such as erbium fluoride (ErF$_3$) can be used. Further alternatively, the substances for forming the electron-transport layer 114, which are described above, can be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, for example, the substances for forming the electron-transport layer 114 (e.g., a metal complex and a heteroaromatic compound), which are described above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, alkali metal oxide or alkaline earth metal oxide such as lithium oxide, calcium oxide, barium oxide, and the like can be given. A Lewis base such as magnesium oxide can alternatively be used. An organic compound such as tetrathiafulvalene (abbreviation: TTF) can alternatively be used.

Note that each of the above-described hole-injection layer 111, hole-transport layer 112, light-emitting layer 113, electron-transport layer 114, electron-injection layer 115, and charge-generation layer 116 can be formed by a method such as an evaporation method (e.g., a vacuum evaporation method), an ink-jet method, or a coating method.

In the above-described light-emitting element, current flows due to a potential difference generated between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a light-transmitting property.

The above-described light-emitting element can emit phosphorescence originating from the organometallic complex and thus can have higher efficiency than a light-emitting element using a fluorescent compound.

Note that the light-emitting element described in this embodiment is an example of a light-emitting element manufactured using the organometallic complex that is one embodiment of the present invention. Further, as a light-emitting device including the above light-emitting element, a passive matrix light-emitting device and an active matrix light-emitting device can be manufactured. It is also possible to manufacture a light-emitting device with a microcavity structure including a light-emitting element which is a different light-emitting element from the above light-emitting elements as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, there is also no particular limitation on crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

(Embodiment 3)

In this embodiment, as one embodiment of the present invention, a light-emitting element in which two or more kinds of organic compounds as well as a phosphorescent organometallic iridium complex are used for a light-emitting layer is described.

Figure 2:
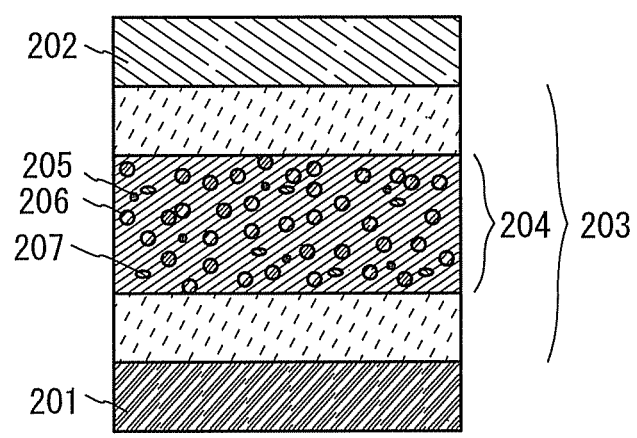
FIG. 2 illustrates a light-emitting element of one embodiment of the present invention.

A light-emitting element described in this embodiment includes an EL layer 203 between a pair of electrodes (a first electrode 201 and a second electrode 202) as illustrated in FIG. 2. Note that the EL layer 203 includes at least a light-emitting layer 204 and may include a hole-injection layer, a hole-transport layer, an electron-transport layer, an electron-injection layer, a charge-generation layer, and the like. Note that substances for the hole-injection layer, the hole-transport layer, the electron-transport layer, the electron-injection layer, and the charge-generation layer can be similar to the substances for the hole-injection layer 111, the hole-transport layer 112, the electron-transport layer 114, the electron-injection layer 115, and the charge-generation layer 116, respectively, which are described in Embodiment 2.

In this embodiment, the first electrode 201 functions as an anode, and the second electrode 202 functions as a cathode. Note that structures of the first electrode 201 and the second electrode 202 can be similar to those of the first electrode 101 and the second electrode 103 described in Embodiment 2.

The light-emitting layer 204 described in this embodiment contains a phosphorescent compound 205 using the phosphorescent organometallic iridium complex described in Embodiment 1, a first organic compound 206, and a second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

Note that it is preferable that a triplet excitation energy level ($T_1$ level) of each of the first organic compound 206 and the second organic compound 207 be higher than that of the phosphorescent compound 205. This is because, when the $T_1$ level of the first organic compound 206 (or the second organic compound 207) is lower than that of the phosphorescent compound 205, the triplet excitation energy of the phosphorescent compound 205, which is to contribute to light emission, is quenched by the first organic compound 206 (or the second organic compound 207) and accordingly the emission efficiency decreases.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (a fluorescence spectrum in energy transfer from a singlet excited state, and a phosphorescence spectrum in energy transfer from a triplet excited state) largely overlap with an absorption spectrum of a guest material (specifically, a spectrum in an absorption band on the longest wavelength (lowest energy) side). However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side as compared to the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, in this embodiment, a combination of the first organic compound 206 and the second organic compound 207 preferably forms an exciplex (also referred to as excited complex). In that case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex which is located on a longer wavelength side. Moreover, when the first organic compound 206 and the second organic compound 207 are selected in such a manner that the emission spectrum of the exciplex largely overlaps with the absorption spectrum of the guest material, energy transfer from a singlet excited state can be maximized. Note that also in the case of a triplet excited state, energy transfer from the exciplex, not the host material, is assumed to occur.

For the phosphorescent compound 205, the phosphorescent organometallic iridium complex described in Embodiment 1 is used. Although the combination of the first organic compound 206 and the second organic compound 207 can be determined such that an exciplex is formed, a combination of a compound which is likely to accept electrons (a compound having an electron-trapping property) and a compound which is likely to accept holes (a compound having a hole-trapping property) is preferably employed.

As examples of a compound which is likely to accept electrons, the following can be given: 2-[3-(dibenzothiophen-4-yl)phenyl]dibenzo[f,h]quinoxaline (abbreviation: 2mDBTPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl] dibenzo[f,h]quinoxaline (abbreviation: 7mDBTPDBq-II), and 6-[3-(dibenzothiophen-4-yl)phenyl] dibenzo[f,h] quinoxaline (abbreviation: 6mDBTPDBq-II).

As examples of a compound which is likely to accept holes, the following can be given: 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-N,N'-diphenylamino-9H-fluoren-7-yl)diphenylamine (abbreviation: DPNF), N,N', N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino] biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

As for the above-described first and second organic compounds 206 and 207, the present invention is not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound 206 to the second organic compound 207 is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of a light-emitting element.

Note that in another structure of the present invention, the light-emitting layer 204 can be formed using a host molecule having a hole-trapping property and a host molecule having an electron-trapping property as the two kinds of organic compounds other than the phosphorescent compound 205 that is the guest material so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds which are likely to accept holes and the above-described compounds which are likely to accept electrons.

Note that the light-emitting element described in this embodiment is an example of a structure of a light-emitting element; it is possible to apply a light-emitting element having another structure, which is described in another embodiment, to a light-emitting device that is one embodiment of the present invention. Further, as a light-emitting device including the above light-emitting element, a passive matrix light-emitting device and an active matrix light-emitting device can be manufactured. It is also possible to, manufacture a light-emitting device with a microcavity structure including the above light-emitting element, whose structure is changed as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, there is also no particular limitation on crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

(Embodiment 4)

In this embodiment, as one embodiment of the present invention, a light-emitting element (hereinafter referred to as tandem light-emitting element) in which a plurality of EL layers are included so as to sandwich a charge-generation layer will be described.

Figure 3A:
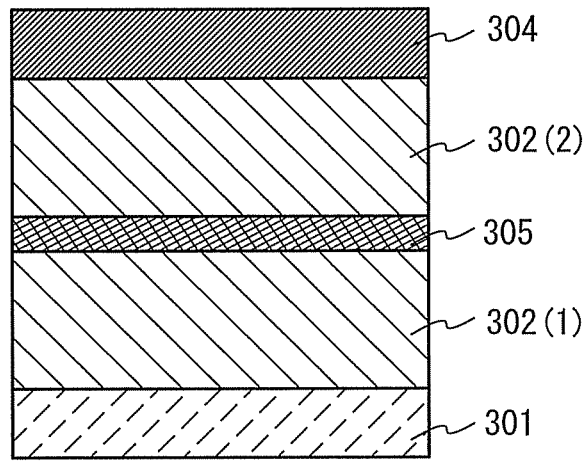
FIGS. 3A and 3B each illustrate a light-emitting element of one embodiment of the present invention.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those of the first electrode 101 and the second electrode 103 which are described in Embodiment 2.

In addition, although the plurality of EL layers (the first EL layer 302(1) and the second EL layer 302(2)) may have a structure similar to that of the EL layer described in Embodiment 2 or Embodiment 3, any of the EL layers may have a structure similar to that of the EL layer described in Embodiment 2 or 3. In other words, the structures of the first EL layer 302(1) and the second EL layer 302(2) may be the same or different from each other and can be similar to that of the EL layer described in Embodiment 2 or Embodiment 3.

Further, a charge-generation layer 305 is provided between the plurality of EL layers (the first EL layer 302(1) and the second EL layer 302(2)). The charge-generation layer 305 has a function of injecting electrons into one of the EL layers and injecting holes into the other of the EL layers when a voltage is applied between the first electrode 301 and the second electrode 304. For example, when a voltage is applied to the first electrode 301 such that the potential of the first electrode 301 is higher than that of the second electrode 304, the charge-generation layer 305 injects electrons into the first EL layer 302(1) and injects holes into the second EL layer 302(2).

Note that in terms of light extraction efficiency, the charge-generation layer 305 preferably has a light-transmitting property with respect to visible light (specifically, the charge-generation layer 305 has a visible light transmittance of 40% or more). Further, the charge-generation layer 305 functions even if it has lower conductivity than the first electrode 301 or the second electrode 304.

The charge-generation layer 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/Vs or higher. However, substances other than the above substances may be used as long as they are organic compounds having a hole-transport property higher than an electron-transport property.

Further, as the electron acceptor, 7,7,8,8-tetracyano-2,3,5,6-tetrafluoroquinodimethane (abbreviation: F$_4$-TCNQ), chloranil, or the like can be used. Alternatively, a transition metal oxide can be used. Further alternatively, an oxide of metals that belong to Group 4 to Group 8 of the periodic table can be used. Specifically, it is preferable to use vanadium oxide, niobium oxide, tantalum oxide, chromium oxide, molybdenum oxide, tungsten oxide, manganese oxide, or rhenium oxide because the electron-accepting property is high. Among these, molybdenum oxide is especially preferable because it is stable in the air, has a low hygroscopic property, and is easily handled.

On the other hand, in the case of the structure in which an electron donor is added to an organic compound having a high electron-transport property, as the organic compound having a high electron-transport property for example, a metal complex having a quinoline skeleton or a benzoquinoline skeleton, such as Alq, Almq$_3$, BeBq$_2$, or BAlq, or the like can be used. Alternatively, it is possible to use a metal complex having an oxazole-based ligand or a thiazole-based ligand, such as Zn(BOX)$_2$ or Zn(BTZ)$_2$. Further alternatively, instead of a metal complex, it is possible to use PBD, OXD-7, TAZ, BPhen, BCP, or the like. The substances mentioned here are mainly ones that have an electron mobility of $10^{-6}$ cm$^2$/Vs or higher. Note that substances other than the above substances may be used as long as they are organic compounds having an electron-transport property higher than a hole-transport property.

As the electron donor, it is possible to use an alkali metal, an alkaline earth metal, a rare earth metal, a metal belonging to Group 2 or 13 of the periodic table, or an oxide or a carbonate thereof. Specifically, it is preferable to use lithium (Li), cesium (Cs), magnesium (Mg), calcium (Ca), ytterbium (Yb), indium (In), lithium oxide, cesium carbonate, or the like. Alternatively, an organic compound such as tetrathianaphthacene may be used as the electron donor.

Note that forming the charge-generation layer 305 by using any of the above materials can suppress an increase in drive voltage caused by the stack of the EL layers.

Figure 3B:
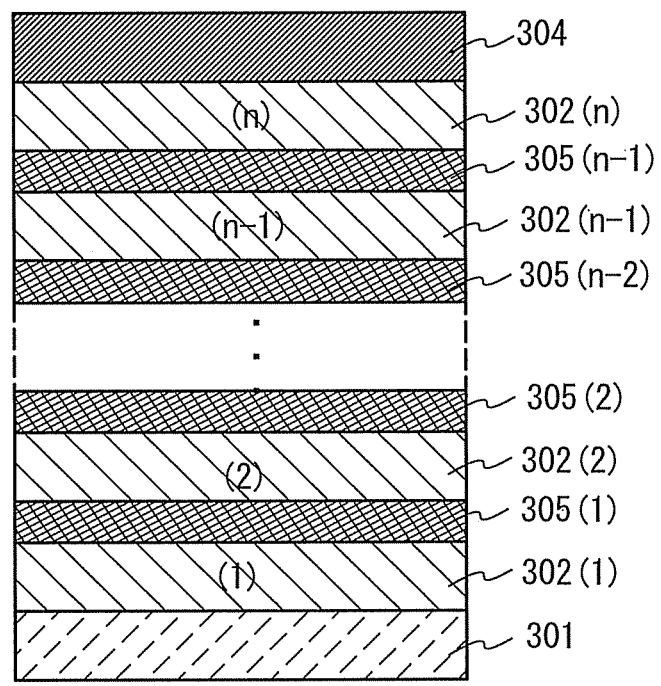

Although FIG. 3A illustrates the light-emitting element having two EL layers, the present invention can be similarly applied to a light-emitting element in which n EL layers (n is a natural number of three or more) are stacked as illustrated in FIG. 3B. In the case where a plurality of EL layers are included between a pair of electrodes as in the light-emitting element according to this embodiment, by provision of a charge-generation layer between the EL layers, light emission in a high luminance region can be obtained with current density kept low. Since the current density can be kept low, the element can have a long lifetime. When the light-emitting element is applied for lighting, voltage drop due to resistance of an electrode material can be reduced, thereby achieving homogeneous light emission in a large area. Moreover, it is possible to achieve a light-emitting device of low power consumption, which can be driven at a low voltage.

By making the EL layers emit light of different colors from each other, the light-emitting element can provide light emission of a desired color as a whole. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. In other words, when lights obtained from substances which emit light of complementary colors are mixed, white emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

(Embodiment 5)

In this embodiment, as a light-emitting device utilizing phosphorescence which is one embodiment of the present invention, a light-emitting device using a phosphorescent organometallic iridium complex is described.

Figure 4:
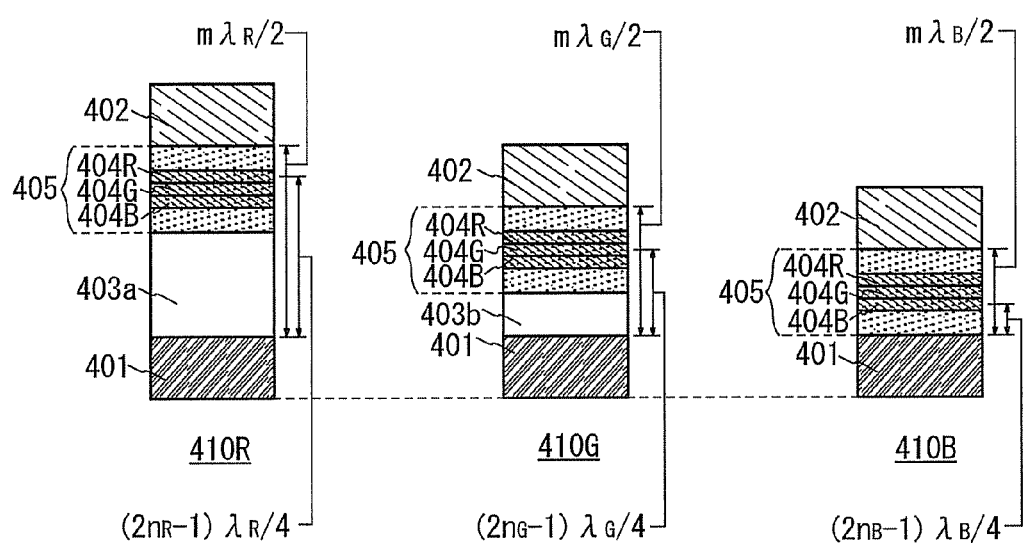
FIG. 4 illustrates a light-emitting element of one embodiment of the present invention.

A light-emitting device described in this embodiment has a micro optical resonator (microcavity) structure in which a light resonant effect between a pair of electrodes is utilized. The light-emitting device includes a plurality of light-emitting elements each of which has at least an EL layer 405 between a pair of electrodes (a reflective electrode 401 and a semi-transmissive and semi-reflective electrode 402) as illustrated in FIG. 4. Further, the EL layer 405 includes at least a light-emitting layer 404 serving as a light-emitting region and may further include a hole-injection layer, a hole-transport layer, an electron-transport layer, an electron-injection layer, a charge-generation layer, and the like. Note that the light-emitting layer 404 contains an organometallic complex of one embodiment of the present invention.

In this embodiment, a light-emitting device is described which includes light-emitting elements (a first light-emitting element 410R, a second light-emitting element 410G, and a third light-emitting element 410B) having different structures as illustrated in FIG. 4.

The first light-emitting element 410R has a structure in which a first transparent conductive layer 403a, an EL layer 405, and a semi-transmissive and semi-reflective electrode 402 are sequentially stacked over a reflective electrode 401. The second light-emitting element 410G has a structure in which a second transparent conductive layer 403b, the EL layer 405, and the semi-transmissive and semi-reflective electrode 402 are sequentially stacked over the reflective electrode 401. The third light-emitting element 410B has a structure in which the EL layer 405 and the semi-transmissive and semi-reflective electrode 402 are sequentially stacked over the reflective electrode 401.

Note that the reflective electrode 401, the EL layer 405, and the semi-transmissive and semi-reflective electrode 402 are common to the light-emitting elements (the first light-emitting element 410R, the second light-emitting element 410G, and the third light-emitting element 410B).

Further, the EL layer 405 includes a first light-emitting layer 404B, a second light-emitting layer 404G, and a third light-emitting layer 404R. Note that the first light-emitting layer 404B emits light ($\lambda_B$) having a peak in a wavelength range from 420 nm to 480 nm. The second light-emitting layer 404G emits light ($\lambda_G$) having a peak in a wavelength range from 500 nm to 550 nm. The third light-emitting layer 404R emits light ($\lambda_R$) having a peak in a wavelength range from 600 nm to 760 nm. Thus, in each of the light-emitting elements (the first light-emitting element 410R, the second light-emitting element 410G, and the third light-emitting element 410B), light emitted from the first light-emitting layer 404B, light emitted from the second light-emitting layer 404G, and light emitted from the third light-emitting layer 404R overlap with each other; accordingly, light having a broad emission spectrum that covers a visible light range can be emitted. Note that the above wavelengths satisfy the relation of $\lambda_B < \lambda_G < \lambda_R$.

Each of the light-emitting elements described in this embodiment has a structure in which the EL layer 405 is interposed between the reflective electrode 401 and the semi-transmissive and semi-reflective electrode 402. Light emitted in all directions from the light-emitting layers included in the EL layer 405 is resonated by the reflective electrode 401 and the semi-transmissive and semi-reflective electrode 402 which function as a micro optical resonator (microcavity). Note that the reflective electrode 401 is formed using a conductive material having reflectivity, and a film whose visible light reflectivity is 40% to 100%, preferably 70% to 100%, and whose resistivity is $1\times10^{-2}$ Ωcm or lower is used. In addition, the semi-transmissive and semi-reflective electrode 402 is formed using a conductive material having reflectivity and a conductive material having a light-transmitting property, and a film whose visible light reflectivity is 20% to 80%, preferably 40% to 70%, and whose resistivity is $1\times10^{-2}$ $\Omega$cm or lower is used.

In this embodiment, the thicknesses of the transparent conductive layers (the first transparent conductive layer 403a and the second transparent conductive layer 403b) provided in the first light-emitting element 410R and the second light-emitting element 410G, respectively, are varied between the light-emitting elements, whereby the light-emitting elements differ in the optical path length from the reflective electrode 401 to the semi-transmissive and semi-reflective electrode 402. In other words, in light having a broad emission spectrum, which is emitted from the light-emitting layers of each of the light-emitting elements, light with a wavelength that is resonated between the reflective electrode 401 and the semi-transmissive and semi-reflective electrode 402 can be enhanced while light with a wavelength that is not resonated therebetween can be attenuated. Thus, when the elements differ in the optical path length from the reflective electrode 401 to the semi-transmissive and semi-reflective electrode 402, light with different wavelengths can be extracted.

Note that the optical path length (also referred to as optical distance) is expressed as a product of an actual distance and a refractive index, and in this embodiment, is a product of an actual thickness and n (refractive index). That is, an optical path length=actual thickness×n.

Note that the optical path length from the reflective electrode 401 to the semi-transmissive and semi-reflective electrode 402 is set to $m\lambda_R/2$ (m is a natural number of 1 or more) in the first light-emitting element 410R; the optical path length from the reflective electrode 401 to the semi-transmissive and semi-reflective electrode 402 is set to $m\lambda_G/2$ (m is a natural number of 1 or more) in the second light-emitting element 410G; and the optical path length from the reflective electrode 401 to the semi-transmissive and semi-reflective electrode 402 is set to $m\lambda_B/2$ (m is a natural number of 1 or more) in the third light-emitting element 410B.

In this manner, the light ($\lambda_R$) emitted from the third light-emitting layer 404R included in the EL layer 405 is mainly extracted from the first light-emitting element 410R, the light ($\lambda_G$) emitted from the second light-emitting layer 404G included in the EL layer 405 is mainly extracted from the second light-emitting element 410G, and the light ($\lambda_B$) emitted from the first light-emitting layer 404B included in the EL layer 405 is mainly extracted from the third light-emitting element 410B. Note that the light extracted from each of the light-emitting elements is emitted from the semi-transmissive and semi-reflective electrode 402 side.

Further, strictly speaking, the optical path length from the reflective electrode 401 to the semi-transmissive and semi-reflective electrode 402 can be the length from a reflection region in the reflective electrode 401 to a reflection region in the semi-transmissive and semi-reflective electrode 402. However, it is difficult to precisely determine the positions of the reflection regions in the reflective electrode 401 and the semi-transmissive and semi-reflective electrode 402; therefore, it is assumed that the above effect can be sufficiently obtained wherever the reflection regions may be set in the reflective electrode 401 and the semi-transmissive and semi-reflective electrode 402.

Next, the optical path length from the reflective electrode 401 to the third light-emitting layer 404R is adjusted to $(2n_R-1)\lambda_R/4$, where $n_R$ is a natural number of 1 or more, because in the first light-emitting element 410R, light (third reflected light) that is reflected by the reflective electrode 401 of the light emitted from the third light-emitting layer 404R interferes with light (third incident light) that directly enters the semi-transmissive and semi-reflective electrode 402 from the third light-emitting layer 404R. By adjusting the optical path length, the phases of the first reflected light and the first incident light can be aligned with each other and the light emitted from the third light-emitting layer 404R can be amplified.

Note that strictly speaking, the optical path length from the reflective electrode 401 to the third light-emitting layer 404R can be the optical path length from a reflection region in the reflective electrode 401 to a light-emitting region in the third light-emitting layer 404R. However, it is difficult to precisely determine the positions of the reflection region in the reflective electrode 401 and the light-emitting region in the third light-emitting layer 404R; therefore, it is assumed that the above effect can be sufficiently obtained wherever the reflection region and the light-emitting region may be set in the reflective electrode 401 and the third light-emitting layer 404R, respectively.

Next, the optical path length from the reflective electrode 401 to the second light-emitting layer 404G is adjusted to $(2n_G-1)\lambda_G/4$, where $n_G$ is a natural number of 1 or more, because in the second light-emitting element 410G, light (second reflected light) that is reflected by the reflective electrode 401 of the light emitted from the second light-emitting layer 404G interferes with light (second incident light) that directly enters the semi-transmissive and semi-reflective electrode 402 from the second light-emitting layer 404G. By adjusting the optical path length, the phases of the second reflected light and the second incident light can be aligned with each other and the light emitted from the second light-emitting layer 404G can be amplified.

Note that strictly speaking, the optical path length from the reflective electrode 401 to the second light-emitting layer 404G can be the optical path length from a reflection region in the reflective electrode 401 to a light-emitting region in the second light-emitting layer 404G. However, it is difficult to precisely determine the positions of the reflection region in the reflective electrode 401 and the light-emitting region in the second light-emitting layer 404G; therefore, it is assumed that the above effect can be sufficiently obtained wherever the reflection region and the light-emitting region may be set in the reflective electrode 401 and the second light-emitting layer 404G, respectively.

Next, the optical path length from the reflective electrode 401 to the first light-emitting layer 404B is adjusted to $(2n_B-1)\lambda_B/4$, where $n_B$ is a natural number of 1 or more, because in the third light-emitting element 410B, light (first reflected light) that is reflected by the reflective electrode 401 of the light emitted from the first light-emitting layer 404B interferes with light (first incident light) that directly enters the semi-transmissive and semi-reflective electrode 402 from the first light-emitting layer 404B. By adjusting the optical path length, the phases of the third reflected light and the third incident light can be aligned with each other and the light emitted from the first light-emitting layer 404B can be amplified.

Note that strictly speaking, the optical path length from the reflective electrode 401 to the first light-emitting layer 404B can be the optical path length from a reflection region in the reflective electrode 401 to a light-emitting region in the first light-emitting layer 404B. However, it is difficult to precisely determine the positions of the reflection region in the reflective electrode 401 and the light-emitting region in the first light-emitting layer 404B; therefore, it is assumed that the above effect can be sufficiently obtained wherever the reflection region and the light-emitting region may be set in the reflective electrode 401 and the first light-emitting layer 404B, respectively.

Note that although each of the light-emitting elements in the above-described structure includes a plurality of light-emitting layers in the EL layer, the present invention is not limited thereto; for example, the structure of the tandem light-emitting element which is described in Embodiment 4 can be combined, in which case a plurality of EL layers are provided so as to sandwich a charge-generation layer in one light-emitting element and one or more light-emitting layers are formed in each of the EL layers.

The light-emitting device described in this embodiment has a microcavity structure, in which light with wavelengths which differ depending on the light-emitting elements can be extracted even when they include the same EL layers, so that it is not needed to form light-emitting elements for the colors of R, G, and B. Therefore, the above structure is advantageous for full color display owing to easiness in achieving higher resolution display or the like. In addition, emission intensity with a predetermined wavelength in the front direction can be increased, whereby power consumption can be reduced. The above structure is particularly useful in the case of being applied to a color display (image display device) including pixels of three or more colors but may also be applied to lighting or the like.

(Embodiment 6)

In this embodiment, a light-emitting device including a light-emitting element in which an organometallic complex that is one embodiment of the present invention is used for a light-emitting layer is described.

The light-emitting device can be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 5A and 5B.

Figure 5A:
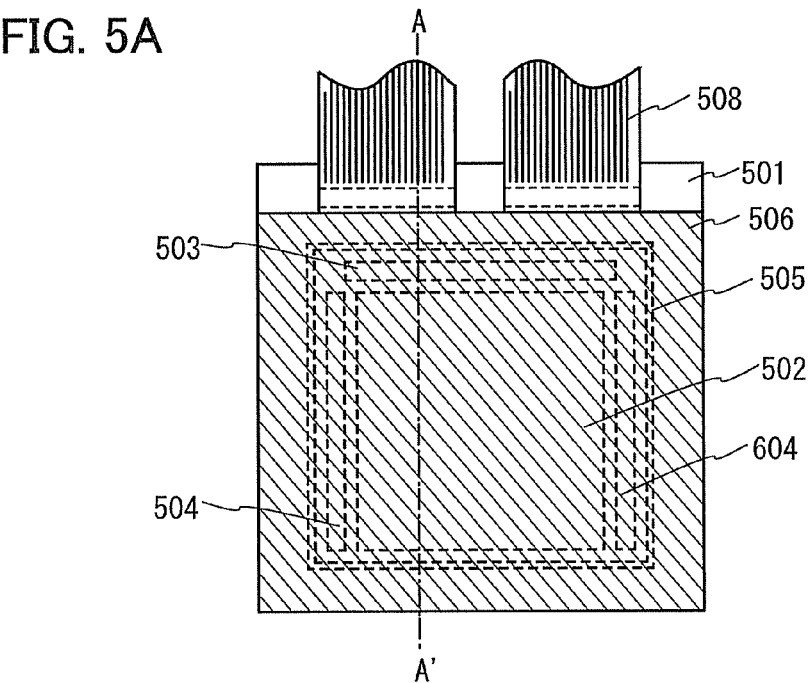
FIGS. 5A and 5B illustrate an active matrix light-emitting device.
Figure 5B:
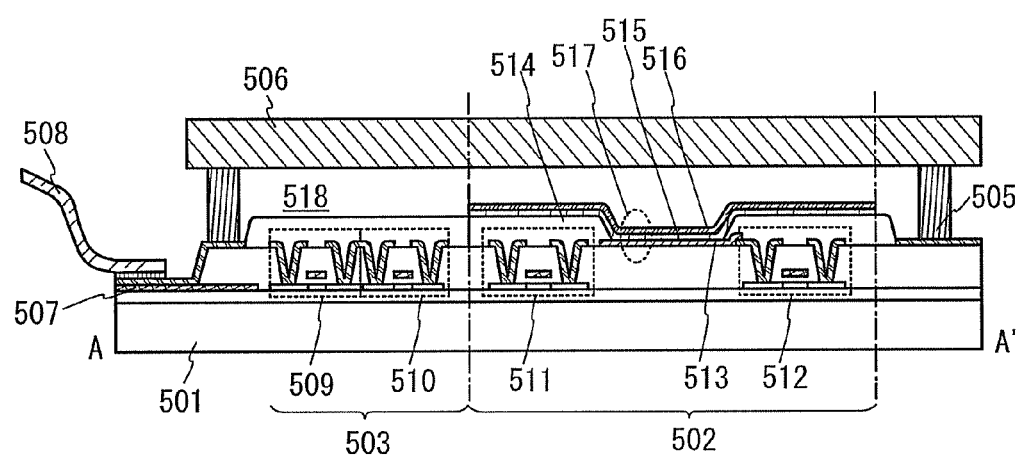

Note that FIG. 5A is a top view illustrating a light-emitting device and FIG. 5B is a cross-sectional view taken along the chain line A-A' in FIG. 5A. The active matrix light-emitting device according to this embodiment includes a pixel portion 502 provided over an element substrate 501, a driver circuit portion (a source line driver circuit) 503, and a driver circuit portion (a gate line driver circuit) 504. The pixel portion 502, the driver circuit portion 503, and the driver circuit portion 504 are sealed between the element substrate 501 and a sealing substrate 506 by a sealant 505.

In addition, a lead wiring 507 is provided over the element substrate 501. The lead wiring 507 is provided for connecting an external input terminal through which a signal (e.g., a video signal, a clock signal, a start signal, and a reset signal) or a potential from the outside is transmitted to the driver circuit portion 503 and the driver circuit portion 504. Here is shown an example in which a flexible printed circuit (FPC) 508 is provided as the external input terminal. Although the FPC 508 is illustrated alone, this FPC may be provided with a printed wiring board (PWB). The light-emitting device in the present specification includes, in its category, not only the light-emitting device itself but also the light-emitting device provided with the FPC or the PWB.

Next, a cross-sectional structure is described with reference to FIG. 5B. The driver circuit portion and the pixel portion are formed over the element substrate 501; here are illustrated the driver circuit portion 503 which is the source line driver circuit and the pixel portion 502.

The driver circuit portion 503 is an example where a CMOS circuit is formed, which is a combination of an n-channel TFT 509 and a p-channel TFT 510. Note that a circuit included in the driver circuit portion may be formed using various CMOS circuits, PMOS circuits, or NMOS circuits. Although this embodiment shows a driver integrated type in which the driver circuit is formed over the substrate, the driver circuit is not necessarily formed over the substrate, and the driver circuit can be formed outside, not over the substrate.

The pixel portion 502 is formed of a plurality of pixels each of which includes a switching TFT 511, a current control TFT 512, and a first electrode 513 which is electrically connected to a wiring (a source electrode or a drain electrode) of the current control TFT 512. Note that an insulator 514 is formed to cover end portions of the first electrode 513. In this embodiment, the insulator 514 is formed using a positive photosensitive acrylic resin.

The insulator 514 preferably has a curved surface with curvature at an upper end portion or a lower end portion thereof in order to obtain favorable coverage by a film which is to be stacked over the insulator 514. For example, in the case of using a positive photosensitive acrylic resin as a material for the insulator 514, the insulator 514 preferably has a curved surface with a curvature radius (0.2 μm to 3 μm) at the upper end portion. Note that the insulator 514 can be formed using either a negative photosensitive resin that becomes insoluble in an etchant by light irradiation or a positive photosensitive resin that becomes soluble in an etchant by light irradiation. It is possible to use, without limitation to an organic compound, either an organic compound or an inorganic compound such as silicon oxide or silicon oxynitride.

An EL layer 515 and a second electrode 516 are stacked over the first electrode 513. In the EL layer 515, at least a light-emitting layer is provided which contains an organometallic complex that is one embodiment of the present invention. Further, in the EL layer 515, a hole-injection layer, a hole-transport layer, an electron-transport layer, an electron-injection layer, a charge-generation layer, and the like can be provided as appropriate in addition to the light-emitting layer.

A light-emitting element 517 is formed of a stacked structure of the first electrode 513, the EL layer 515, and the second electrode 516. For the first electrode 513, the EL layer 515, and the second electrode 516, the materials described in Embodiment 2 can be used. Although not illustrated, the second electrode 516 is electrically connected to an FPC 508 which is an external input terminal.

Note that in this embodiment, the first electrode 513 functions as an anode, and the second electrode 516 functions as a cathode.

Although the cross-sectional view of FIG. 5B illustrates only one light-emitting element 517, a plurality of light-emitting elements are arranged in matrix in the pixel portion 502. Light-emitting elements which provide three kinds of light emission (R, G, and B) are selectively formed in the pixel portion 502, whereby a light-emitting device capable of full color display can be fabricated. Alternatively, a light-emitting device which is capable of full color display may be fabricated by a combination with color filters.

Further, the sealing substrate 506 is attached to the element substrate 501 with the sealant 505, whereby a light-emitting element 517 is provided in a space 518 surrounded by the element substrate 501, the sealing substrate 506, and the sealant 505. The space 518 may be filled with an inert gas (such as nitrogen or argon), or the sealant 505.

An epoxy-based resin is preferably used for the sealant 505. It is preferable that such a material do not transmit moisture or oxygen as much as possible. As the sealing substrate 506, a glass substrate, a quartz substrate, or a plastic substrate formed of fiberglass reinforced plastic (FRP), polyvinyl fluoride (PVF), polyester, acrylic, or the like can be used.

As described above, an active matrix light-emitting device can be obtained.

Note that the structure described in this embodiment can be combined as appropriate with any of the structures described in the other embodiments.

(Embodiment 7)

In this embodiment, examples of a variety of electronic devices which are completed using a light-emitting device will be described with reference to FIGS. 6A to 6D. To the light-emitting device, an organometallic complex that is one embodiment of the present invention is applied.

Examples of the electronic devices to which the light-emitting device is applied are a television device (also referred to as television or television receiver), a monitor of a computer or the like, a camera such as a digital camera or a digital video camera, a digital photo frame, a mobile phone (also referred to as cellular phone or cellular phone device), a portable game machine, a portable information terminal, an audio reproducing device, and a large-sized game machine such as a pachinko machine. Specific examples of these electronic devices are illustrated in FIGS. 6A to 6D.

Figure 6A:
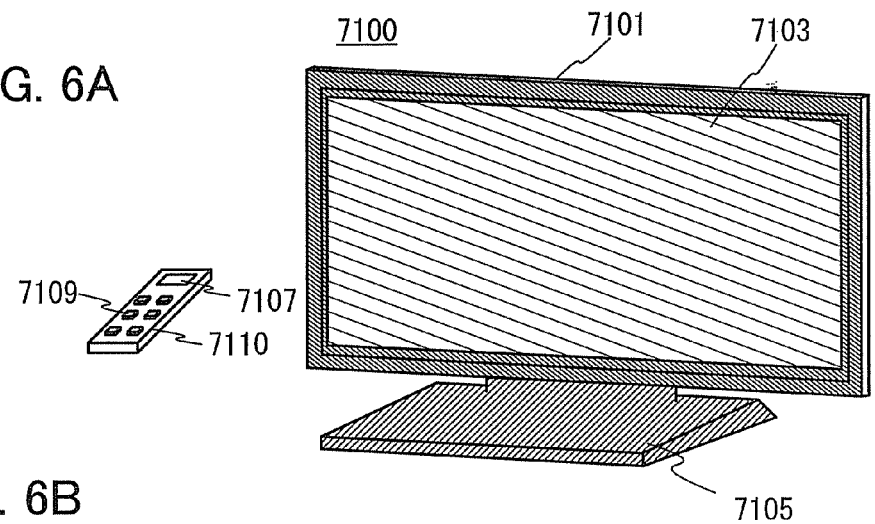
FIGS. 6A to 6D illustrate electronic devices.

FIG. 6A illustrates an example of a television set. In a television set 7100, a display portion 7103 is incorporated in a housing 7101. Images can be displayed on the display portion 7103, and the light-emitting device can be used for the display portion 7103. In addition, here, the housing 7101 is supported by a stand 7105.

Operation of the television set 7100 can be performed with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television set 7100 is provided with a receiver, a modem, and the like. With the receiver, a general television broadcast can be received. Furthermore, when the television set 7100 is connected to a communication network by wired or wireless connection via the modem, one-way (from a transmitter to a receiver) or two-way (between a transmitter and a receiver, between receivers, or the like) data communication can be performed.

Figure 6B:
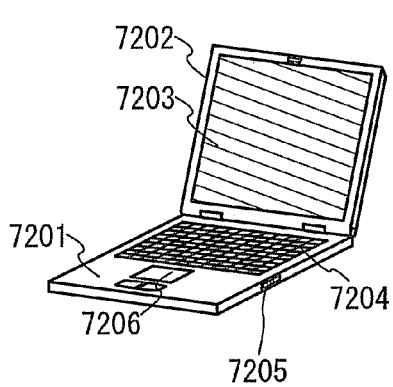

FIG. 6B illustrates a computer having a main body 7201, a housing 7202, a display portion 7203, a keyboard 7204, an external connection port 7205, a pointing device 7206, and the like. Note that this computer is manufactured using the light-emitting device for the display portion 7203.

Figure 6C:
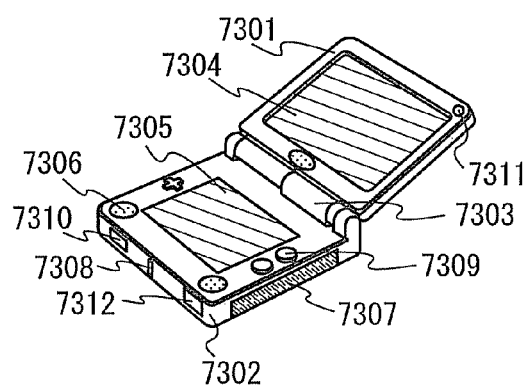

FIG. 6C illustrates a portable game machine having two housings, a housing 7301 and a housing 7302, which are connected with a joint portion 7303 so that the portable game machine can be opened or folded. A display portion 7304 is incorporated in the housing 7301, and a display portion 7305 is incorporated in the housing 7302. In addition, the portable game machine illustrated in FIG. 6C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the light-emitting device is used for at least one of the display portion 7304 and the display portion 7305, and may include other accessories as appropriate. The portable game machine illustrated in FIG. 6C has a function of reading out a program or data stored in a storage medium to display it on the display portion, and a function of sharing information with another portable game machine by wireless communication. The portable game machine illustrated in FIG. 6C can have a variety of functions without limitation to the above.

Figure 6D:
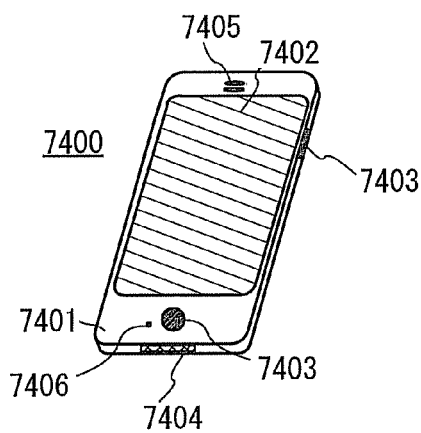

FIG. 6D illustrates an example of a mobile phone. A mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using the light-emitting device for the display portion 7402.

When the display portion 7402 of the mobile phone 7400 illustrated in FIG. 6D is touched with a finger or the like, data can be input to the mobile phone 7400. Further, operations such as making a call and composing an e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically switched by determining the orientation of the mobile phone 7400 (whether the mobile phone is placed horizontally or vertically for a landscape mode or a portrait mode).

The screen modes are switched by touching the display portion 7402 or operating the operation buttons 7403 of the housing 7401. The screen modes can also be switched depending on the kind of image displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken when the display portion 7402 is touched with the palm or the finger, whereby personal authentication can be performed. Further, by providing a backlight or a sensing light source which emits near-infrared light in the display portion, an image of a finger vein, a palm vein, or the like can be taken.

As described above, the electronic devices can be obtained by application of the light-emitting device according to one embodiment of the present invention. The light-emitting device has a remarkably wide application range, and can be applied to electronic devices in a variety of fields.

Note that the structure described in this embodiment can be combined as appropriate with any of the structures described in the other embodiments.

(Embodiment 8)

In this embodiment, examples of a lighting device to which a light-emitting device including an organometallic complex that is one embodiment of the present invention is applied will be described with reference to FIG. 7.

Figure 7:
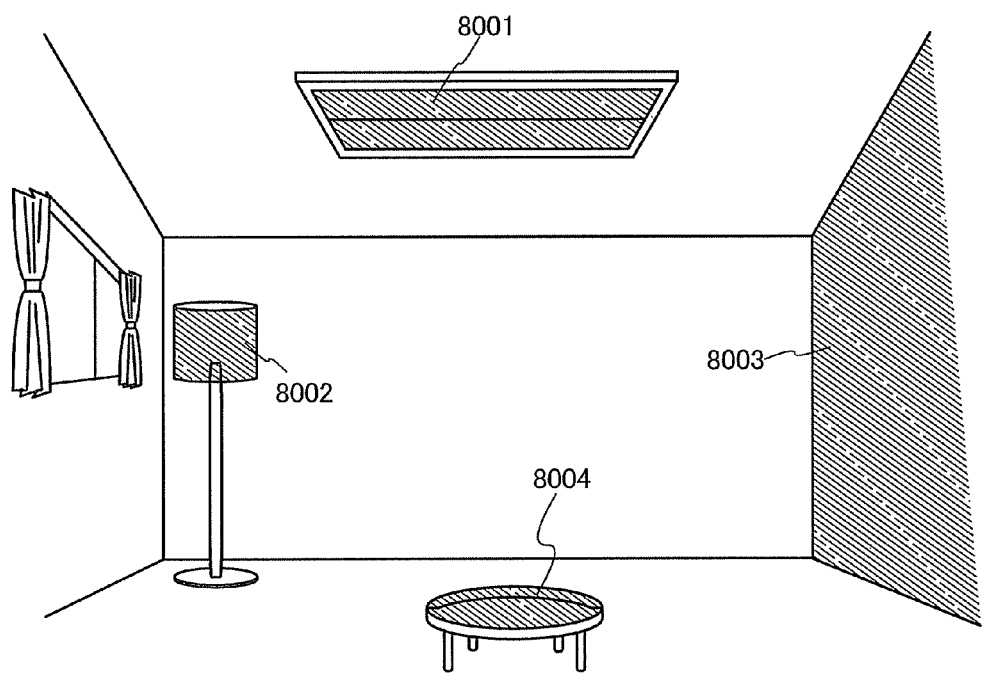
FIG. 7 illustrates lighting devices.

FIG. 7 illustrates an example in which the light-emitting device is used as an indoor lighting device 8001. Since the light-emitting device can have a larger area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large-sized lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

Note that the structure described in this embodiment can be combined as appropriate with any of the structures described in the other embodiments.

Example 1

Synthesis Example 1

This example specifically illustrates a synthesis example of tris[1-(2-methyphenyl)-3-phenyl-5-propyl-1H-1,2,4-triaz-olato]iridium(III) (abbreviation: [Ir(Prp3tz1-mp)₃]), the organometallic complex of one embodiment of the present invention which is represented by Structural Formula (110) in Embodiment 1. A structure of [Ir(Prp3tz1-mp)₃] (abbreviation) is shown below.

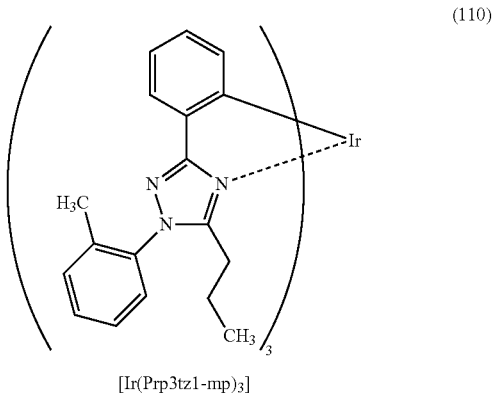

[Ir(Prp3tz1-mp)₃]

Step 1: Synthesis of N-(1-ethoxybenzylidene)butyramide

First, 10 g of ethyl benzimidate hydrochloride, 150 mL of toluene, and 11 g of triethylamine (Et₃N) were put into a 500-mL three-neck flask and this mixture was stirred at room temperature for 10 minutes. After a predetermined time elapsed, with a 50-mL dropping funnel, a mixed solution of 5.8 g of butyryl chloride and 30 mL of toluene was added dropwise to this mixture, and the mixture was stirred at room temperature for 24 hours. After the stirring, this mixture was suction-filtered, and the obtained filtrate was concentrated to give N-(1-ethoxybenzylidene)butyramide (a yellow oily substance, 100% yield). The synthesis scheme of Step 1 is shown in (A-1) below.

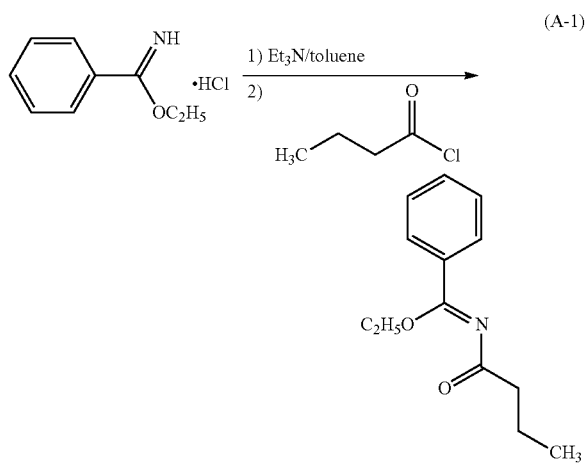

Step 2: Synthesis of 1-(2-Methylphenyl)-3-phenyl-5-propyl-1H-1,2,4-triazole (Abbreviation: HPrp3tz1-mp)

Next, 8.1 g of o-tolyl hydrazine hydrochloride and 100 mL of carbon tetrachloride were put into a 500-mL three-neck flask, 7.8 g of triethylamine (Et₃N) was added dropwise to this mixture little by little, and the mixture was stirred at room temperature for 1 hour. After a predetermined time elapsed, 11 g of N-(1-ethoxybenzylidene)butyramide obtained in Step 1 was added to the mixture, and the mixture was stirred at room temperature for 24 hours. After the stirring, the mixture was dissolved in chloroform and washed with water and saturated saline. After the washing, anhydrous magnesium sulfate was added to the organic layer for drying. This mixture was gravity-filtered, and the obtained filtrate was concentrated to give an oily substance. This oily substance was purified by silica gel column chromatography. As the developing solvent, a mixed solvent of dichloromethane and ethyl acetate in a ratio of 24:1 (v/v) was used. The obtained fraction was concentrated, so that 1-(2-methylphenyl)-3-phenyl-5-propyl-1H-1,2,4-triazole (abbreviation: HPrp3tz1-mp) was obtained (a red oily substance, 45% yield). The synthesis scheme of Step 2 is shown in (A-2) below.

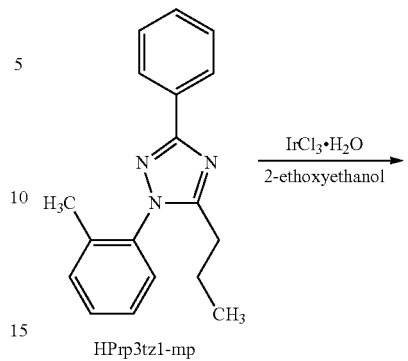

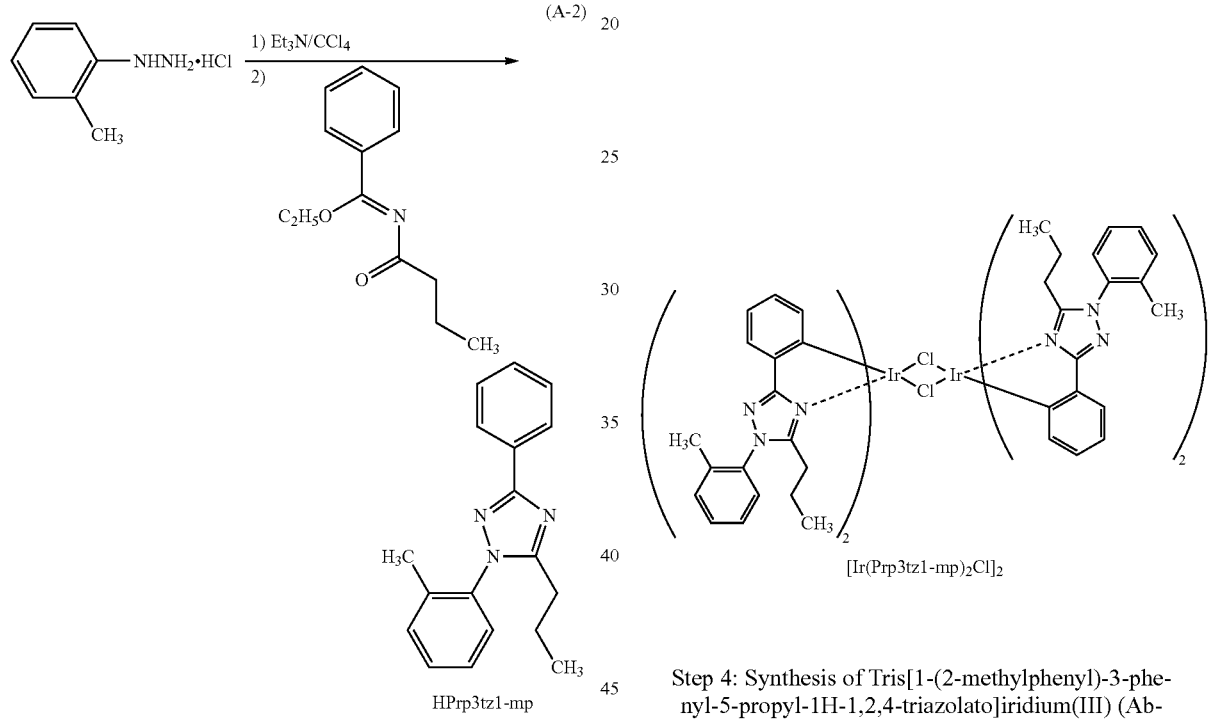

Step 3: Synthesis of Di-μ-chloro-bis[bis(1-(2-methylphenyl)-3-phenyl-5-propyl-1H-1,2,4-triazolato)iridium(III)] (Abbreviation: [Ir(Prp3tz1-mp)₂Cl]₂)>

Then, 1.0 g of HPrp3tz1-mp which is the ligand obtained in Step 2, 0.51 g of iridium chloride hydrate (IrCl₃.H₂O), 12 mL of 2-ethoxyethanol, and 4 mL of water were put into a 50-mL recovery flask and the air in the flask was replaced with argon. This reaction container was subjected to microwaves under conditions of 100 W and 100° C. for 1 hour to cause a reaction. After a predetermined time elapsed, the obtained reacted solution was dissolved in dichloromethane and washed with water and saturated saline. Anhydrous magnesium sulfate was added to the organic layer for drying, and the resulting mixture was gravity-filtered to give filtrate. This filtrate was concentrated, so that a dinuclear complex [Ir(Prp3tz1-mp)₂Cl]₂ (abbreviation) was obtained (brown powder, 91% yield). The synthesis scheme of Step 3 is shown in (A-3) below.

Step 4: Synthesis of Tris[1-(2-methylphenyl)-3-phenyl-5-propyl-1H-1,2,4-triazolato]iridium(III) (Abbreviation: [Ir(Prp3tz1-mp)₃])

Then, 1.2 g of [Ir(Prp3tz1-mp)₂Cl]₂ (abbreviation) which is the dinuclear complex obtained in Step 3, 3.2 g of HPrp3tz1-mp which is the ligand obtained in Step 2, and 0.80 g of silver trifluoromethanesulfonate (TfOAg) were put into a reaction container provided with a three-way cock and a cold tube and heated and stirred in a nitrogen atmosphere at 165° C. for 42 hours. The obtained reaction mixture was dissolved in dichloromethane and suction filtration was carried out to remove insoluble matter. The obtained filtrate was concentrated and purification by silica gel column chromatography was performed. Dichloromethane was used as a developing solvent. The obtained fraction was concentrated, the obtained residue was washed with a mixed solvent of toluene and hexane, and the solution was subjected to suction filtration to give a solid. This solid was recrystallized with a mixed solvent of toluene and hexane, so that [Ir(Prp3tz1-mp)₃] (abbreviation) was obtained (pale yellow powder, 21% yield). The synthesis scheme of Step 4 is shown in (A-4) below.

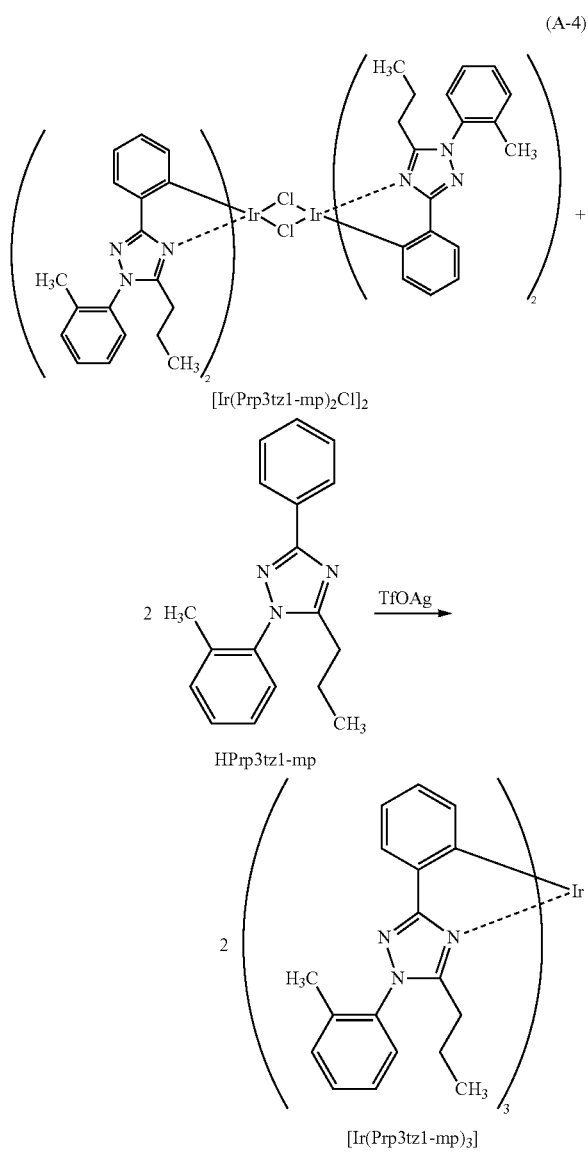

[Ir(Prp3tz1-mp)₂Cl]₂

HPrp3tz1-mp

[Ir(Prp3tz1-mp)₃]

Figure 8:
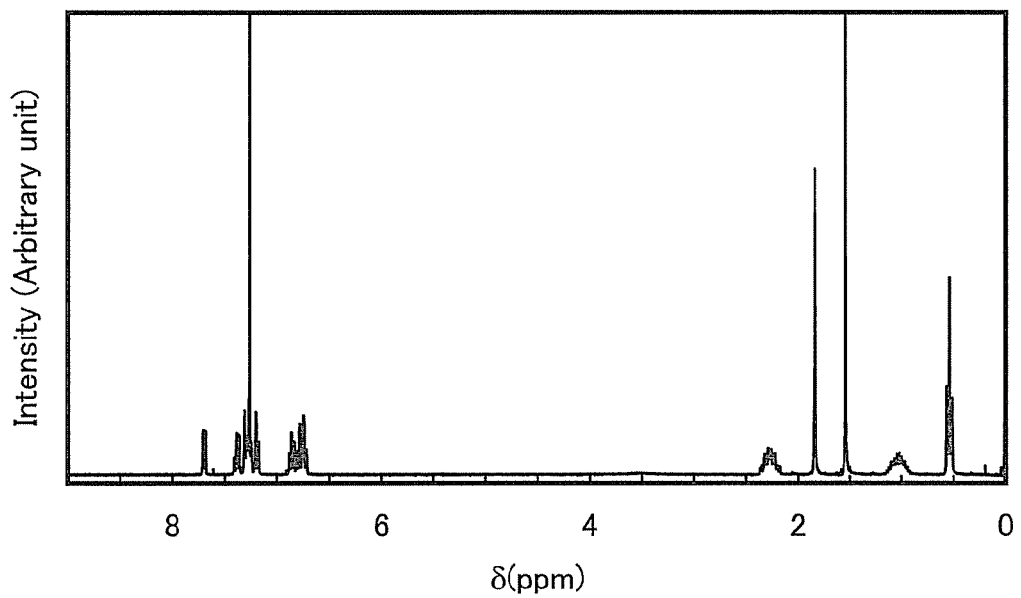
FIG. 8 is a $^1$H NMR chart of an organometallic complex represented by Structural Formula (110).

An analysis result by nuclear magnetic resonance spectrometry (¹H NMR) of the pale yellow powder obtained in Step 4 above is described below. The ¹H NMR chart is shown in FIG. 8. These results revealed that [Ir(Prp3tz1-mp)₃] (abbreviation), the organometallic complex of one embodiment of the present invention which is represented by Structural Formula (110), was obtained in Synthesis Example 1.

¹H NMR data of the obtained substance are as follows:
¹H-NMR. δ (CDCl₃): 0.51-0.56 (t, 9H), 0.94-1.12 (m, 6H), 1.84 (s, 9H), 2.17-2.36 (m, 6H), 6.71-6.88 (m, 9H), 7.18-7.44 (m, 12H), 7.69 (d, 3H).

Figure 9:
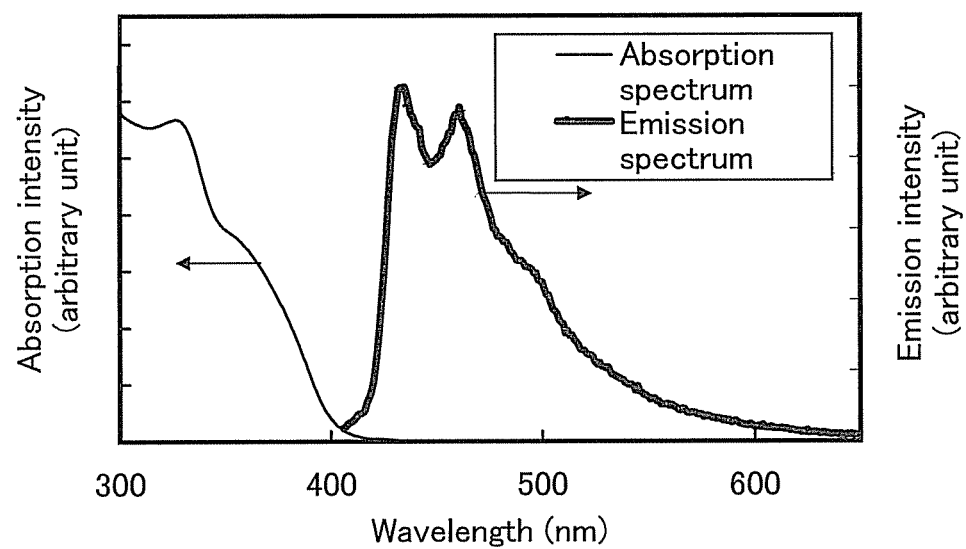
FIG. 9 shows an ultraviolet-visible absorption spectrum and an emission spectrum of an organometallic complex represented by Structural Formula (110) in a dichloromethane solution.

Next, an ultraviolet-visible absorption spectrum (hereinafter, simply referred to as absorption spectrum) and an emission spectrum of [Ir(Prp3tz1-mp)₃] (abbreviation) in a dichloromethane solution were measured. The absorption spectrum was measured with the use of an ultraviolet-visible light spectrophotometer (V-550, manufactured by JASCO Corporation) in the state where a dichloromethane solution (0.11 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.11 mmol/L) was put in a quartz cell at room temperature. FIG. 9 shows measurement results of the absorption spectrum and emission spectrum. The horizontal axis represents wavelength and the vertical axes represent absorption intensity and emission intensity. In FIG. 9, two solid lines are shown; a thin line represents the absorption spectrum, and a thick line represents the emission spectrum. Note that the absorption spectrum in FIG. 9 is a result obtained by subtraction of a measured absorption spectrum of only dichloromethane that was put in a quartz cell from the measured absorption spectrum of the dichloromethane solution (0.11 mmol/L) in a quartz cell.

As shown in FIG. 9, [Ir(Prp3tz1-mp)₃] (abbreviation), the organometallic complex of one embodiment of the present invention, has emission peaks at 435 nm and 461 nm, and blue light was observed from the dichloromethane solution.

Example 2

Synthesis Example 2

This example specifically illustrates a synthesis example of tris[5-methyl-1-(2-methylphenyl)-3-phenyl-1H-1,2,4-triazolato]iridium(III) (abbreviation: [Ir(Mp3tz1-mp)₃]), the organometallic complex of one embodiment of the present invention which is represented by Structural Formula (102) in Embodiment 1. A structure of [Ir(Mp3tz1-mp)₃] (abbreviation) is shown below.

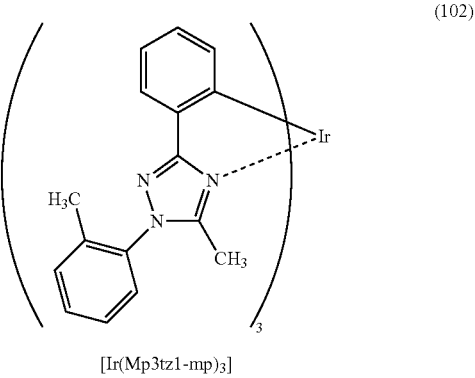

[Ir(Mp3tz1-mp)₃]

Step 1: Synthesis of
N-(1-ethoxybenzylidene)acetamide

First, 10 g of ethyl benzimidate hydrochloride, 150 mL of toluene, and 11 g of triethylamine (Et₃N) were put into a 500-mL three-neck flask and the mixture was stirred at room temperature for 10 minutes. After a predetermined time elapsed, with a 50-mL dropping funnel, a mixed solution of 3.8 g of acetyl chloride and 30 mL of toluene was added dropwise to this mixture, and the mixture was stirred at room temperature for 24 hours. The obtained mixture was suction-filtered, and the obtained filtrate was concentrated to give N-(1-ethoxybenzylidene)acetamide (a yellow oily substance, 100% yield). The synthesis scheme of Step 1 is shown in (B-1) below.

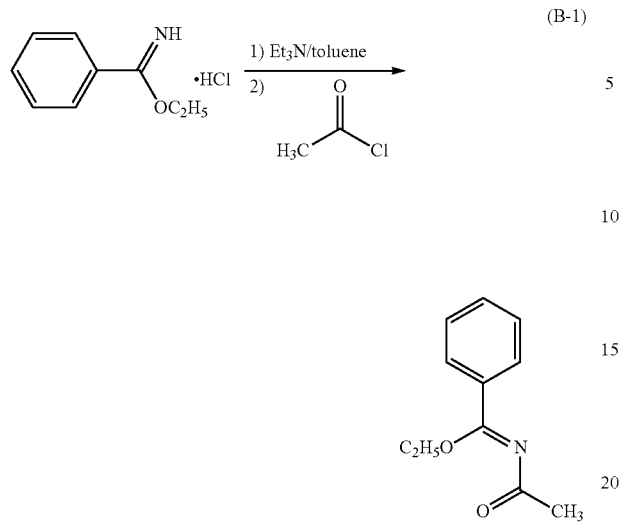

(B-1)

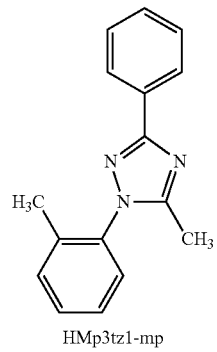

Step 2: Synthesis of 5-Methyl-1-(2-methylphenyl)-3-phenyl-1H-1,2,4-triazole (Abbreviation: HMp3tz1-mp)

Next, 9.1 g of o-tolyl hydrazine hydrochloride and 100 mL of carbon tetrachloride were put into a 300-mL three-neck flask, 12 mL of triethylamine ($Et_3N$) was added dropwise to the mixture little by little, and the mixture was stirred at room temperature for 1 hour. After a predetermined time elapsed, 10 g of N-(1-ethoxybenzylidene)acetamide was added, and the mixture was stirred at room temperature for 19 hours. Then, water was added to this reacted solution and the aqueous layer was subjected to extraction with chloroform. The obtained solution of the extract and the organic layer were combined and washed with saturated saline, and anhydrous magnesium sulfate was added to the organic layer for drying. The obtained mixture was gravity-filtered, and the filtrate was concentrated to give an oily substance. The obtained oily substance was purified by silica gel column chromatography. As the developing solvent, dichloromethane was used. The obtained fraction was concentrated, so that 5-methyl-1-(2-methylphenyl)-3-phenyl-1H-1,2,4-triazole (abbreviation: HMp3tz1-mp) was obtained (a red oily substance, 64% yield). The synthesis scheme of Step 2 is shown in (B-2) below.

Step 3: Synthesis of Di-μ-chloro-bis[bis(5-methyl-1-(2-methylphenyl)-3-phenyl-1H-1,2,4-triazolato)iridium(III)] (Abbreviation: [Ir(Mp3tz1-mp)$_2$Cl]$_2$)

Then, 2.21 g of HMp3tz1-mp which is the ligand obtained in Step 2, 1.26 g of iridium chloride hydrate ($IrCl_3.H_2O$), 15 mL of 2-ethoxyethanol, and 5 mL of water were put into a 50-mL recovery flask and the air in the flask was replaced with argon. This reaction container was subjected to microwaves under conditions of 100 W and 100° C. for 1 hour to cause a reaction. After a predetermined time elapsed, the obtained reacted solution was dissolved in dichloromethane and washed with water and saturated saline. Anhydrous magnesium sulfate was added to the organic layer for drying, and the resulting mixture was gravity-filtered to give filtrate. This filtrate was concentrated, so that a dinuclear complex [Ir(Mp3tz1-mp)$_2$Cl]$_2$ (abbreviation) was obtained (brown powder, 33% yield). The synthesis scheme of Step 3 is shown in (B-3) below.

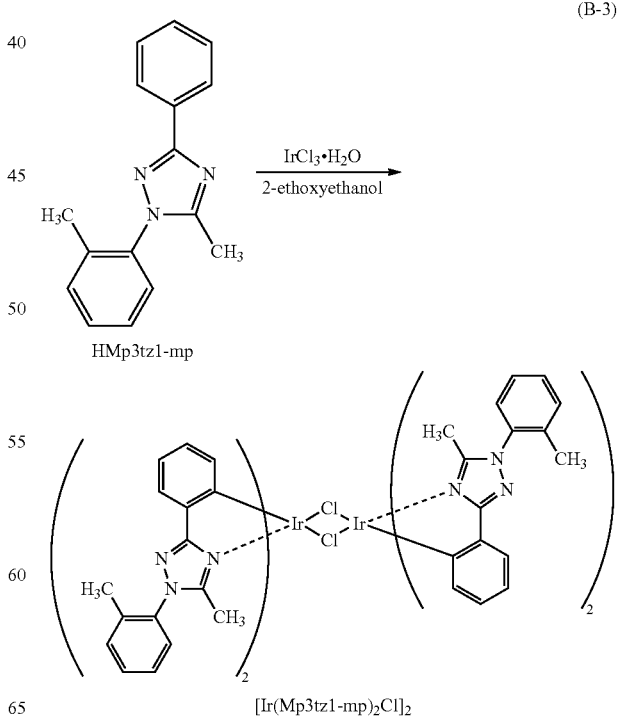

(B-3)

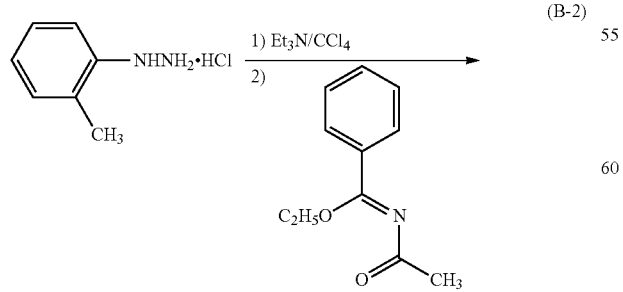

(B-2)

Step 4: Synthesis of Tris(5-methyl-1-(2-methylphenyl)-3-phenyl-1H-1,2,4-triazolato)iridium(III) (Abbreviation: [Ir(Mp3tz1-mp)₃])

Then, 0.5 g of [Ir(Mp3tz1-mp)₂Cl]₂ (abbreviation) which is the dinuclear complex obtained in Step 3, 1.3 g of HMp3tz1-mp which is the ligand obtained in Step 2, and 0.36 g of silver trifluoromethanesulfonate (TfOAg), were put into a reaction container provided with a three-way cock and a cold tube and heated and stirred in a nitrogen atmosphere at 165° C. for 40 hours. The obtained reaction mixture was dissolved in dichloromethane and suction filtration was carried out to remove insoluble matter. The obtained filtrate was concentrated and purification by silica gel column chromatography was performed. As the developing solvent, a mixed solvent of dichloromethane and ethyl acetate in a ratio of 20:1 (v/v) was used. The obtained fraction was concentrated to give a solid. This solid was recrystallized with a mixed solvent of dichloromethane and hexane, so that [Ir(Mp3tz1-mp)₃] (abbreviation) was obtained (pale yellow powder, 15% yield). The synthesis scheme of Step 4 is shown in (B-4) below.

(B-4)

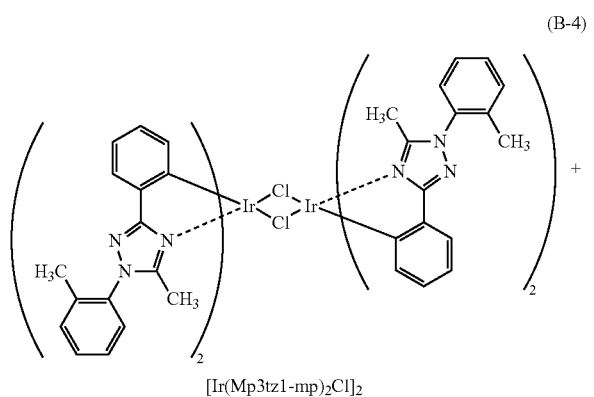

[Ir(Mp3tz1-mp)₂Cl]₂

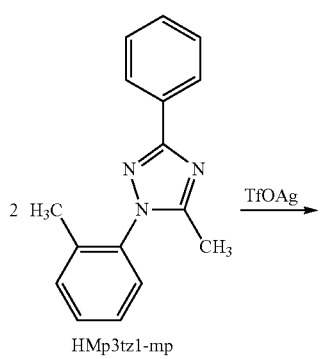

HMp3tz1-mp

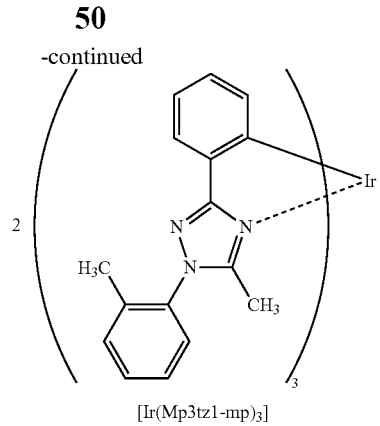

[Ir(Mp3tz1-mp)₃]

Figure 10:
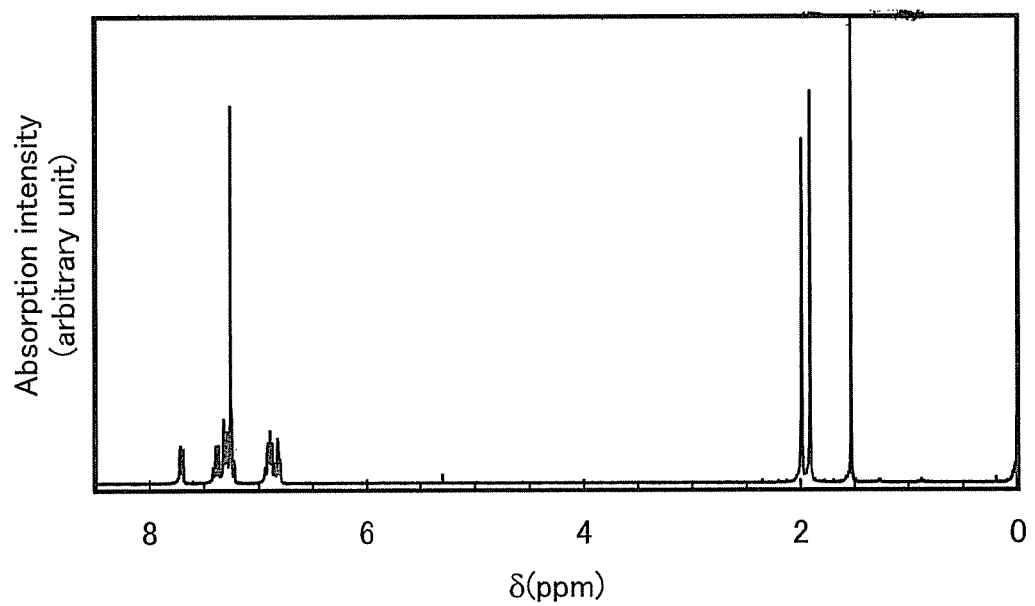
FIG. 10 is a $^1$H NMR chart of an organometallic complex represented by Structural Formula (102).

An analysis result by nuclear magnetic resonance spectrometry (¹H NMR) of the pale yellow powder obtained in Step 4 above is described below. The ¹H NMR chart is shown in FIG. 10. These results revealed that [Ir(Mp3tz1-mp)₃] (abbreviation), the organometallic complex of one embodiment of the present invention which is represented by Structural Formula (102), was obtained in Synthesis Example 2.

¹H NMR data of the obtained substance are as follows:

¹H-NMR. δ (CDCl₃): 1.91 (s, 9H), 1.99 (s, 9H), 6.80-6.95 (m, 9H), 7.22-7.41 (m, 12H), 7.70 (m, 3H).

Figure 11:
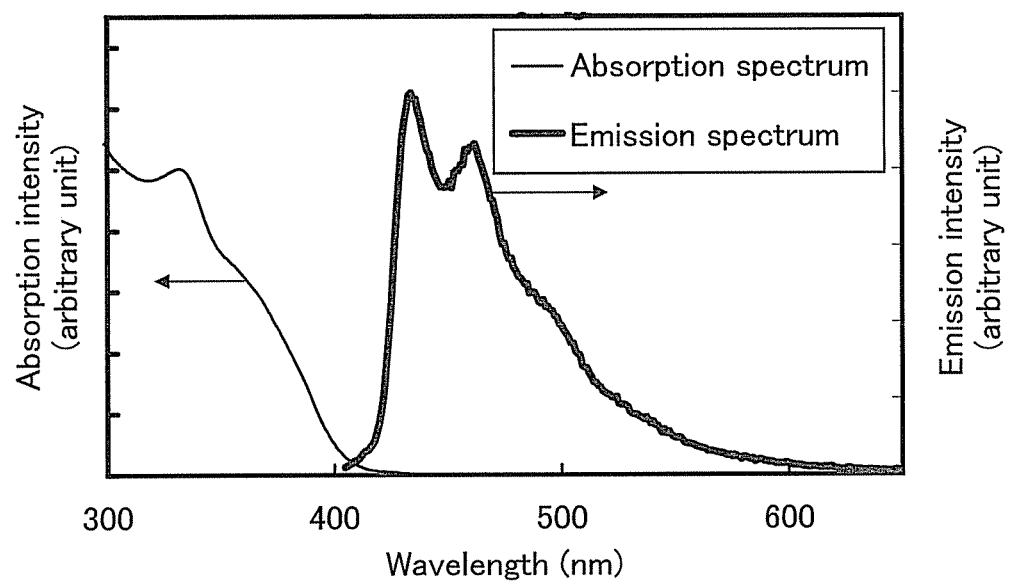
FIG. 11 shows an ultraviolet-visible absorption spectrum and an emission spectrum of an organometallic complex represented by Structural Formula (102) in a dichloromethane solution.

Next, an ultraviolet-visible absorption spectrum (hereinafter, simply referred to as absorption spectrum) and an emission spectrum of [Ir(Mp3tz1-mp)₃] (abbreviation) in a dichloromethane solution were measured. The absorption spectrum was measured with the use of an ultraviolet-visible light spectrophotometer (V-550, manufactured by JASCO Corporation) in the state where a dichloromethane solution (0.096 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.096 mmol/L) was put in a quartz cell at room temperature. FIG. 11 shows measurement results of the absorption spectrum and emission spectrum. The horizontal axis represents wavelength and the vertical axes represent absorption intensity and emission intensity. In FIG. 11, two solid lines are shown; a thin line represents the absorption spectrum, and a thick line represents the emission spectrum. Note that the absorption spectrum in FIG. 11 is a result obtained by subtraction of a measured absorption spectrum of only dichloromethane that was put in a quartz cell from the measured absorption spectrum of the dichloromethane solution (0.096 mmol/L) in a quartz cell.

As shown in FIG. 11, [Ir(Mp3tz1-mp)₃] (abbreviation), the organometallic complex of one embodiment of the present invention, has emission peaks at 434 nm and 462 nm, and blue light was observed from the dichloromethane solution.

Example 3

Synthesis Example 3

This example specifically illustrates a synthesis example of tris(1,3-diphenyl-5-propyl-1H-1,2,4-triazolato)iridium(III) (abbreviation: [Ir(Prp3tz1-Ph)₃]), the organometallic complex of one embodiment of the present invention which is represented by Structural Formula (135) in Embodiment 1. A structure of [Ir(Prp3tz1-Ph)₃] (abbreviation) is shown below.

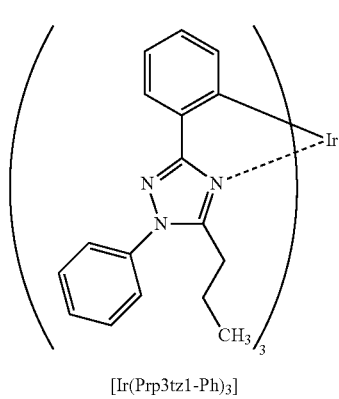

[Ir(Prp3tz1-Ph)₃]

(135)

Step 1: Synthesis of 1,3-Diphenyl-5-propyl-1H-1,2,4-triazole (Abbreviation: HPrp3tz1-Ph)

First, 14 g of phenyl hydrazine hydrochloride and 200 ml of carbon tetrachloride were put into a 500-mL three-neck flask, 30 mL of triethylamine (Et₃N) was added dropwise to the mixture little by little, and the mixture was stirred at room temperature for 1 hour. After a predetermined time elapsed, 17 g of N-(1-ethoxybenzylidene)butyramide obtained in Step 1 of Synthesis Example 1 was added to this mixture, and the mixture was stirred at room temperature for 24 hours. After the stirring, this mixture was dissolved in chloroform and washed with water and saturated saline. After the washing, anhydrous magnesium sulfate was added to the organic layer for drying. This mixture was gravity-filtered, and the obtained filtrate was concentrated to give an oily substance. This oily substance was purified by silica gel column chromatography. As the developing solvent, toluene was used. The obtained fraction was concentrated, so that 1,3-diphenyl-5-propyl-1H-1,2,4-triazole (abbreviation: HPrp3tz1-Ph) was obtained (a red oily substance, 29% yield). The synthesis scheme of Step 1 is shown in (C-1) below.

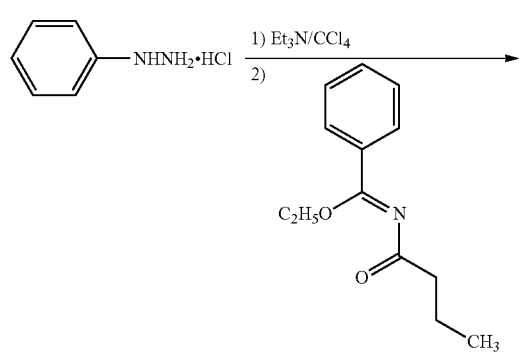

(C-1)

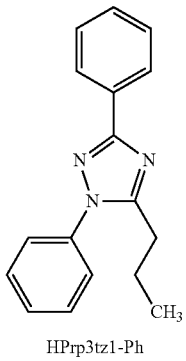

HPrp3tz1-Ph

Step 2: Synthesis of Tris(1,3-diphenyl-5-propyl-1H-1,2,4-triazolato)iridium(III) (Abbreviation: [Ir(Prp3tz1-Ph)₃])

Then, 1.43 g of the ligand HPrp3tz1-Ph obtained in Step 1 above and 0.53 g of tris(acetylacetonato)iridium(III) were put into a reaction container provided with a three-way cock, and the air in the reaction container was replaced with argon. Then, the mixture was heated at 250° C. for 44 hours and 30 minutes to be reacted. The reaction mixture was dissolved in dichloromethane and purification by silica gel column chromatography was performed. Dichloromethane was used as a developing solvent. The obtained fraction was concentrated, so that tris(1,3-diphenyl-5-propyl-1H-1,2,4-triazolato)iridium(III) (abbreviation: [Ir(Prp3tz1-Ph)₃]) was obtained (40 mg of pale yellow powder, 3.8% yield). The synthesis scheme of Step 2 is shown in (C-2) below.

(C-2)

[Ir(Prp3tz1-Ph)₃]

Figure 12:
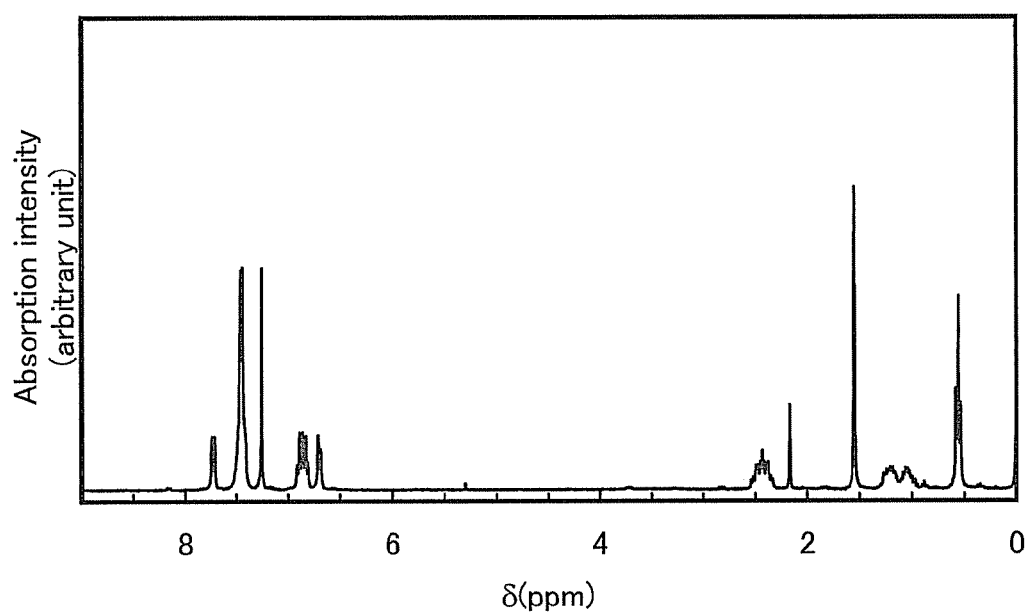
FIG. 12 is a $^1$H NMR chart of an organometallic complex represented by Structural Formula (135).

An analysis result by nuclear magnetic resonance spectrometry ($^1$H NMR) of the pale yellow powder obtained in Step 2 above is described below. The $^1$H NMR chart is shown in FIG. 12. These results revealed that [Ir(Prp3tz1-Ph)$_3$] (abbreviation), the organometallic complex of one embodiment of the present invention which is represented by Structural Formula (135), was obtained in Synthesis Example 3.

$^1$H NMR data of the obtained substance are as follows:

$^1$H-NMR. δ (CDCl$_3$): 0.56 (t, 9H), 0.99-1.27 (m, 6H), 2.33-2.53 (m, 6H), 6.70 (d, 3H), 6.81-6.92 (m, 6H), 7.42-7.51 (m, 15H), 7.73 (d, 3H).

Figure 13:
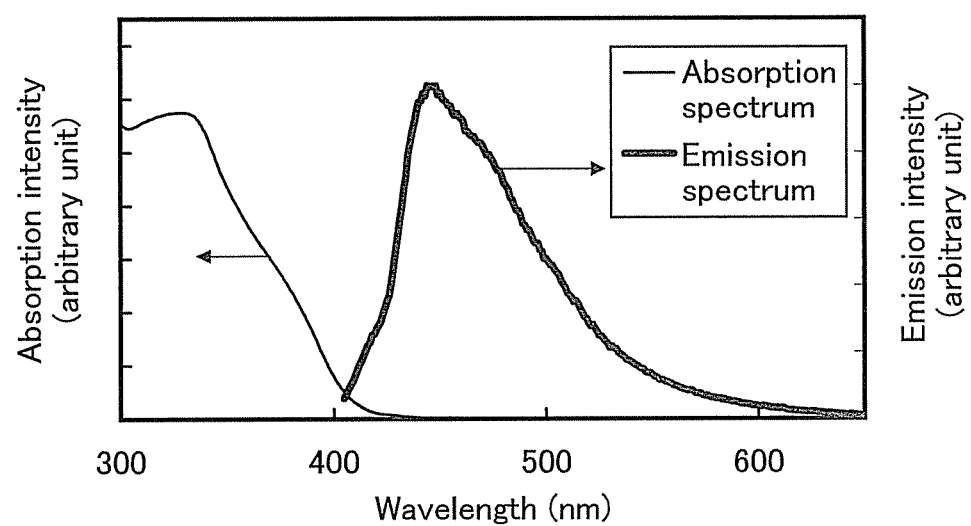
FIG. 13 shows an ultraviolet-visible absorption spectrum and an emission spectrum of an organometallic complex represented by Structural Formula (135) in a dichloromethane solution.

Next, an ultraviolet-visible absorption spectrum (hereinafter, simply referred to as absorption spectrum) and an emission spectrum of [Ir(Prp3tz1-Ph)$_3$] (abbreviation) in a dichloromethane solution were measured. The absorption spectrum was measured with the use of an ultraviolet-visible light spectrophotometer (V-550, manufactured by JASCO Corporation) in the state where a dichloromethane solution (0.051 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.051 mmol/L) was put in a quartz cell at room temperature. FIG. 13 shows measurement results of the absorption spectrum and emission spectrum. The horizontal axis represents wavelength and the vertical axes represent absorption intensity and emission intensity. In FIG. 13, two solid lines are shown; a thin line represents the absorption spectrum, and a thick line represents the emission spectrum. Note that the absorption spectrum in FIG. 13 is a result obtained by subtraction of a measured absorption spectrum of only dichloromethane that was put in a quartz cell from the measured absorption spectrum of the dichloromethane solution (0.051 mmol/L) in a quartz cell.

As shown in FIG. 13, [Ir(Prp3tz1-Ph)$_3$] (abbreviation), the organometallic complex of one embodiment of the present invention, has an emission peak at 444 nm, and blue light was observed from the dichloromethane solution.

Example 4

Synthesis Example 4

This example specifically illustrates a synthesis example of (acetylacetonato)bis[5-methyl-1-(2-methylphenyl)-3-phenyl-1H-1,2,4-triazolato] iridium (III) (abbreviation: [Ir(Mp3tz1-mp)$_2$(acac)]), the organometallic complex of one embodiment of the present invention which is represented by Structural Formula (127) in Embodiment 1. A structure of [Ir(Mp3tz1-mp)$_2$(acac)] (abbreviation) is shown below.

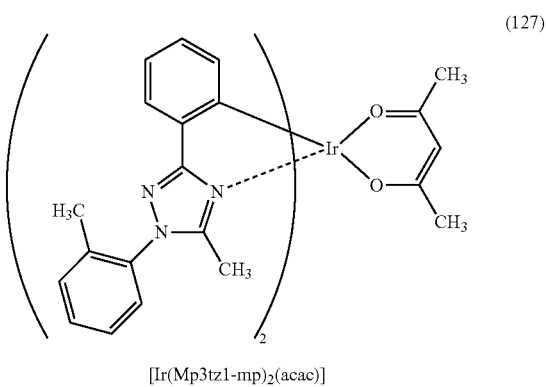

[Ir(Mp3tz1-mp)$_2$(acac)]

Synthesis of (Acetylacetonato)bis[5-methyl-1-(2-methylphenyl)-3-phenyl-1H-1,2,4-triazolato]iridium (III) (Abbreviation: [Ir(Mp3tz1-mp)$_2$(acac)])

First, 0.50 g of [Ir(Mp3tz1-mp)$_2$Cl]$_2$ (abbreviation) which is the dinuclear complex obtained in Step 3 of Synthesis Example 2, 0.10 g of acetyl acetone, 0.37 g of sodium carbonate, and 15 mL of 2-ethoxyethanol were put into a 50-mL recovery flask and the air in the flask was replaced with argon. This reaction container was subjected to microwaves under conditions of 120 W and 100° C. for 1 hour to cause a reaction. After a predetermined time elapsed, the obtained reaction mixture was suction-filtered, and the solid was washed with water to give a solid. This solid was washed with a mixed solvent of dichloromethane and hexane to obtain a solid. The obtained solid was purified by silica gel column chromatography. As the developing solvent, a mixed solvent of dichloromethane and ethyl acetate in a ratio of 10:1 (v/v) was used. The obtained fraction was concentrated to give a solid. This solid was recrystallized with a mixed solvent of dichloromethane and hexane, so that [Ir(Mp3tz1-mp)$_2$(acac)] (abbreviation) was obtained (164 mg of pale yellow powder, 30% yield). The synthesis scheme is shown in (D-1) below.

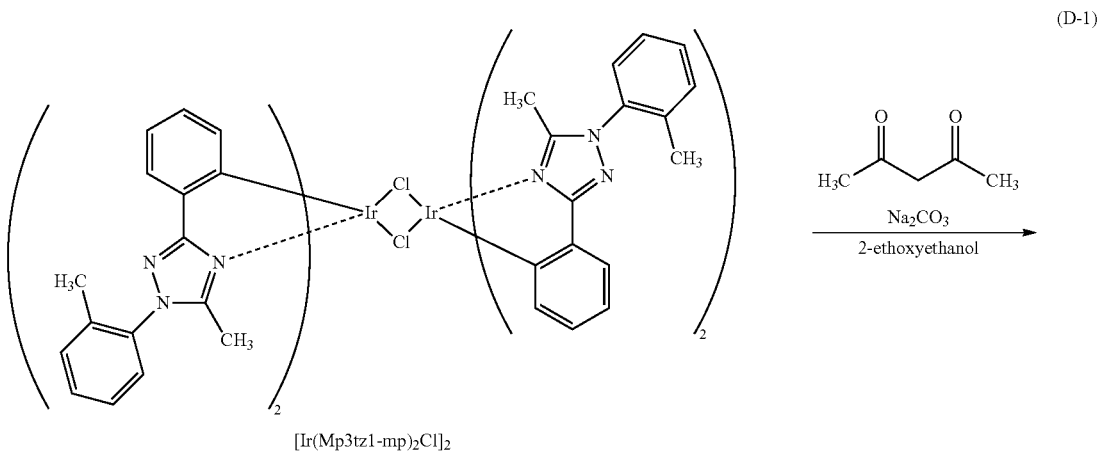

[Ir(Mp3tz1-mp)$_2$Cl]$_2$

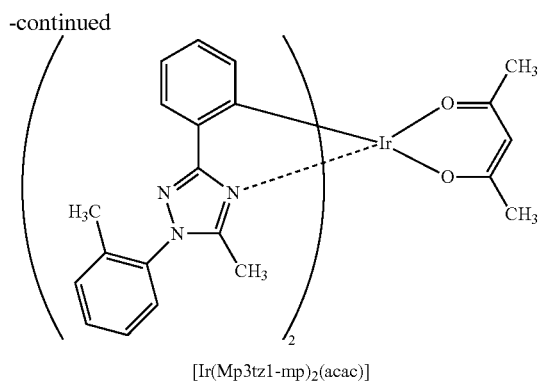

[Ir(Mp3tz1-mp)₂(acac)]

Figure 14:
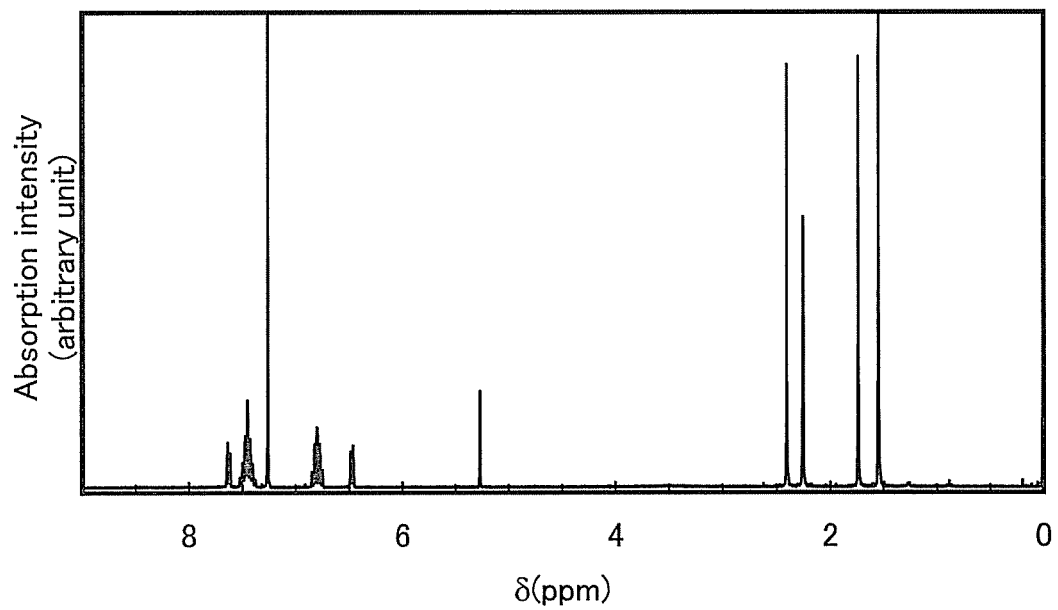
FIG. 14 is a $^1$H NMR chart of an organometallic complex represented by Structural Formula (127).

An analysis result by nuclear magnetic resonance spectrometry (¹H NMR) of the pale yellow powder obtained above is described below. The ¹H NMR chart is shown in FIG. 14. These results revealed that [Ir(Mp3tz1-mp)₂(acac)] (abbreviation), the organometallic complex of one embodiment of the present invention which is represented by Structural Formula (127), was obtained in Synthesis Example 4.

¹H NMR data of the obtained substance are as follows:
¹H-NMR. δ (CDCl₃): 1.91 (s, 9H), 1.99 (s, 9H), 6.80-6.95 (m, 9H), 7.22-7.41 (m, 12H), 7.70 (m, 3H).

Figure 15:
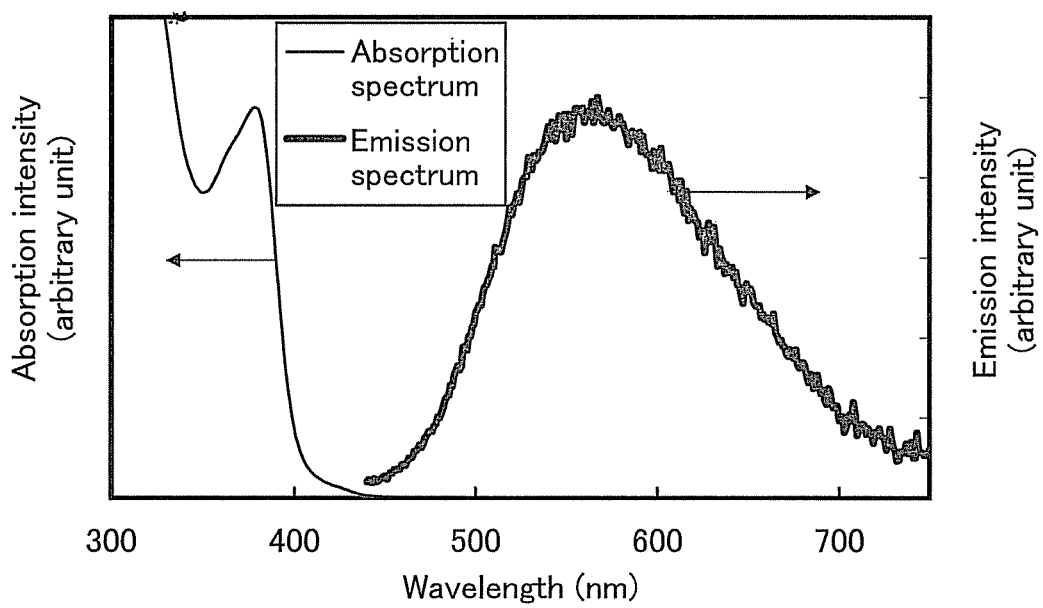
FIG. 15 shows an ultraviolet-visible absorption spectrum and an emission spectrum of an organometallic complex represented by Structural Formula (127) in a dichloromethane solution.

Next, an ultraviolet-visible absorption spectrum (hereinafter, simply referred to as absorption spectrum) and an emission spectrum of [Ir(Mp3tz1-mp)₂(acac)] (abbreviation) in a dichloromethane solution were measured. The absorption spectrum was measured with the use of an ultraviolet-visible light spectrophotometer (V-550, manufactured by JASCO Corporation) in the state where a dichloromethane solution (0.12 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.12 mmol/L) was put in a quartz cell at room temperature. FIG. 15 shows measurement results of the absorption spectrum and emission spectrum. The horizontal axis represents wavelength and the vertical axes represent absorption intensity and emission intensity. In FIG. 15, two solid lines are shown; a thin line represents the absorption spectrum, and a thick line represents the emission spectrum. Note that the absorption spectrum in FIG. 15 is a result obtained by subtraction of a measured absorption spectrum of only dichloromethane that was put in a quartz cell from the measured absorption spectrum of the dichloromethane solution (0.12 mmol/L) in a quartz cell.

As shown in FIG. 15, [Ir(Mp3tz1-mp)₂(acac)] (abbreviation), the organometallic complex of one embodiment of the present invention, has an emission peak at 567 nm, and yellow light was observed from the dichloromethane solution.

Example 5

Synthesis Example 5

This example specifically illustrates a synthesis example of tris[1-(3-biphenyl)-3-phenyl-5-propyl-1H-1,2,4-triazolato]iridium(III) (abbreviation: [Ir(Prp3tz1-3b)₃]), the organometallic complex of one embodiment of the present invention which is represented by Structural Formula (111) in Embodiment 1. A structure of [Ir(Prp3tz1-3b)₃] (abbreviation) is shown below.

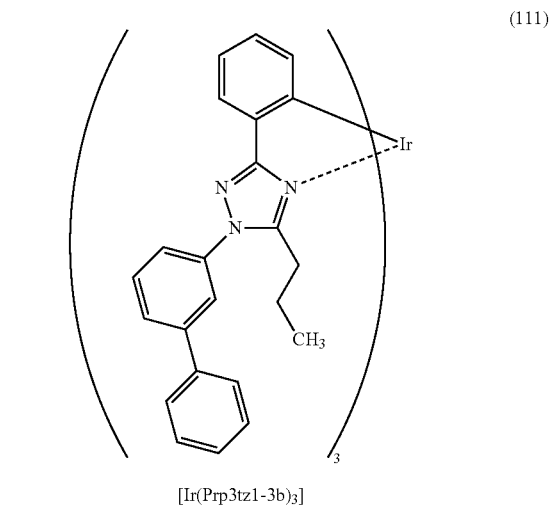

(111)

[Ir(Prp3tz1-3b)₃]

Step 1: Synthesis of 1-(3-Bromophenyl)-3-phenyl-5-propyl-1H-1,2,4-triazole

First, 7.4 g of 3-bromophenyl hydrazine hydrochloride and 80 mL of carbon tetrachloride were put into a 200-mL three-neck flask, 3.5 g of triethylamine (Et₃N) was added dropwise to this mixture little by little, and the mixture was stirred at room temperature for 1 hour. After a predetermined time elapsed, 8.8 g of N-(1-ethoxybenzylidene)butyramide obtained in Step 1 of Synthesis Example 1 was added to this mixture, and the mixture was stirred at room temperature for 24 hours. After the stirring, this mixture was dissolved in chloroform and washed with water and saturated saline. After the washing, anhydrous magnesium sulfate was added to the organic layer for drying. This mixture was gravity-filtered, and the obtained filtrate was concentrated to give an oily substance. This oily substance was purified by silica gel column chromatography. As the developing solvent, dichloromethane was used. The obtained fraction was concentrated to give a solid. This solid was recrystallized with a mixed solvent of toluene and hexane to give 1-(3-bromophenyl)-3-phenyl-5-propyl-1H-1,2,4-triazole (white powder, 47% yield). The synthesis scheme of Step 1 is shown in (E-1) below.

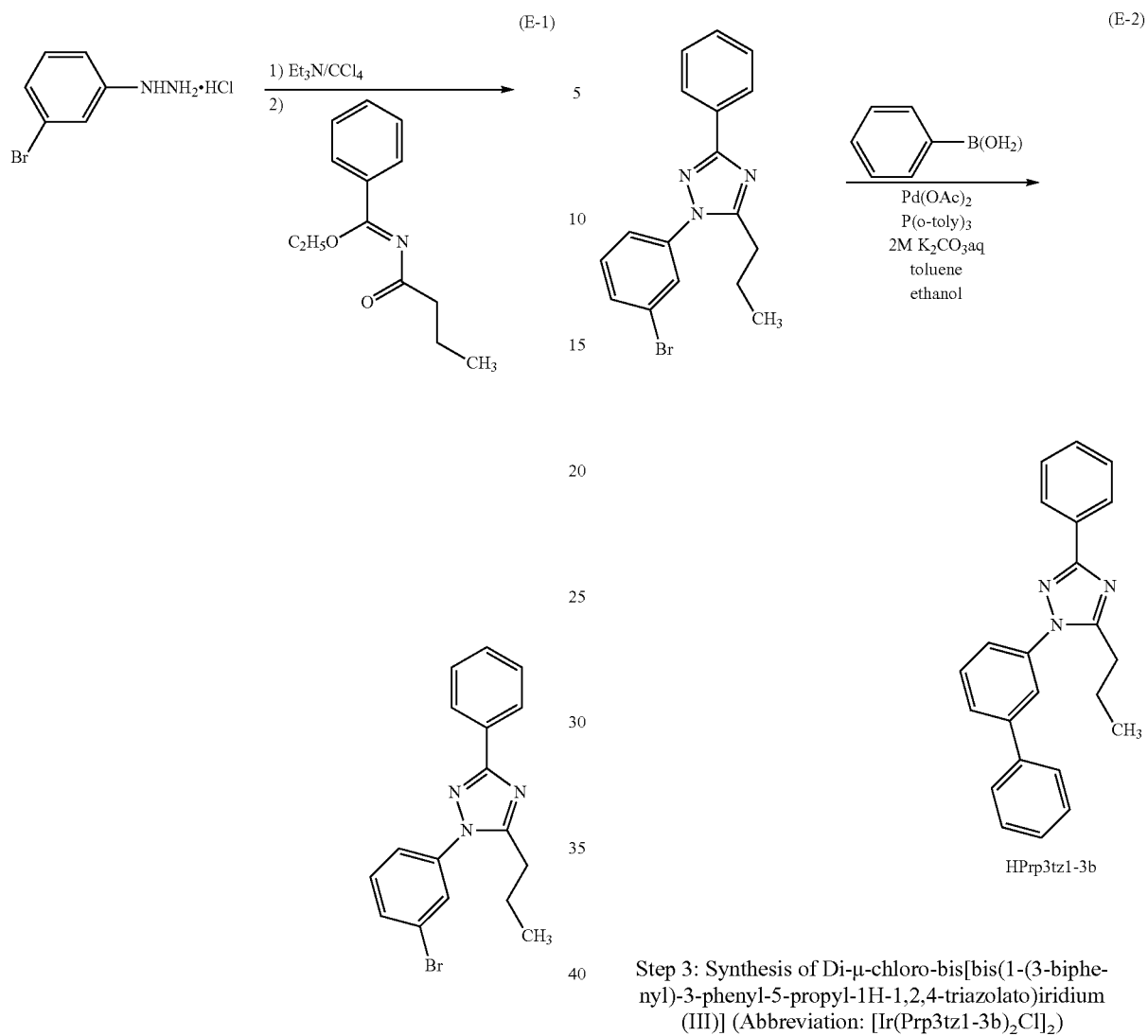

Step 2: Synthesis of 1-(3-Biphenyl)-3-phenyl-5-propyl-1H-1,2,4-triazole (Abbreviation: HPrp3tz1-3b)

Next, 6.44 g of 1-(3-bromophenyl)-3-phenyl-5-propyl-1H-1,2,4-triazole obtained in Step 1 above, 2.75 g of phenylboronic acid, 0.206 g of tri(ortho-tolyl)phosphine, 90 mL of toluene, 10 mL of ethanol, and 23 mL of 2M aqueous solution of potassium carbonate were put into a 200-mL three-neck flask, and the air in the flask was replaced with nitrogen. To this mixture was added 0.051 g of palladium(II) acetate, and the mixture was heated and stirred at 80° C. for 12 hours. The aqueous layer of the obtained reacted solution was subjected to extraction with toluene, and the obtained solution of the extract and the organic layer were combined and washed with a saturated aqueous solution of sodium hydrogen carbonate and saturated saline. Anhydrous magnesium sulfate was added to the organic layer for drying, and the resulting mixture was gravity-filtered to give filtrate. A solid given by concentration of this filtrate was washed with hexane, so that 1-(3-biphenyl)-3-phenyl-5-propyl-1H-1,2,4-triazole (abbreviation: HPrp3tz1-3b) was obtained (white powder, 97% yield). The synthesis scheme of Step 2 is shown in (E-2) below.

Step 3: Synthesis of Di-μ-chloro-bis[bis(1-(3-biphenyl)-3-phenyl-5-propyl-1H-1,2,4-triazolato)iridium (III)] (Abbreviation: [Ir(Prp3tz1-3b)$_2$Cl]$_2$)

Then, 2.5 g of HPrp3tz1-3b which is the ligand obtained in Step 2, 1.05 g of iridium chloride hydrate (IrCl$_3$.H$_2$O), 15 mL of 2-ethoxyethanol, and 5 mL of water were put into a 50-mL recovery flask and the air in the flask was replaced with argon. This reaction container was subjected to microwaves under conditions of 100 W and 100° C. for 1 hour to cause a reaction. After a predetermined time elapsed, the obtained reacted solution was dissolved in dichloromethane and washed with water and saturated saline. Anhydrous magnesium sulfate was added to the organic layer for drying, and the resulting mixture was gravity-filtered to give filtrate. This filtrate was concentrated to give a residue. To this residue, 1.05 g of iridium chloride hydrate (IrCl$_3$.H$_2$O), 15 mL of 2-ethoxyethanol, and 5 mL of water were further added. This mixture was put into a 50-mL recovery flask and the air in the flask was replaced with argon. This reaction container was subjected to microwaves under conditions of 100 W and 100° C. for 1 hour to cause a reaction. The obtained reacted mixed solution was concentrated and the obtained residue was washed with ethanol, so that a dinuclear complex [Ir(Prp3tz1-3b)$_2$Cl]$_2$ (abbreviation) was obtained (brown powder, 100% yield). The synthesis scheme of Step 3 is shown in (E-3) below.

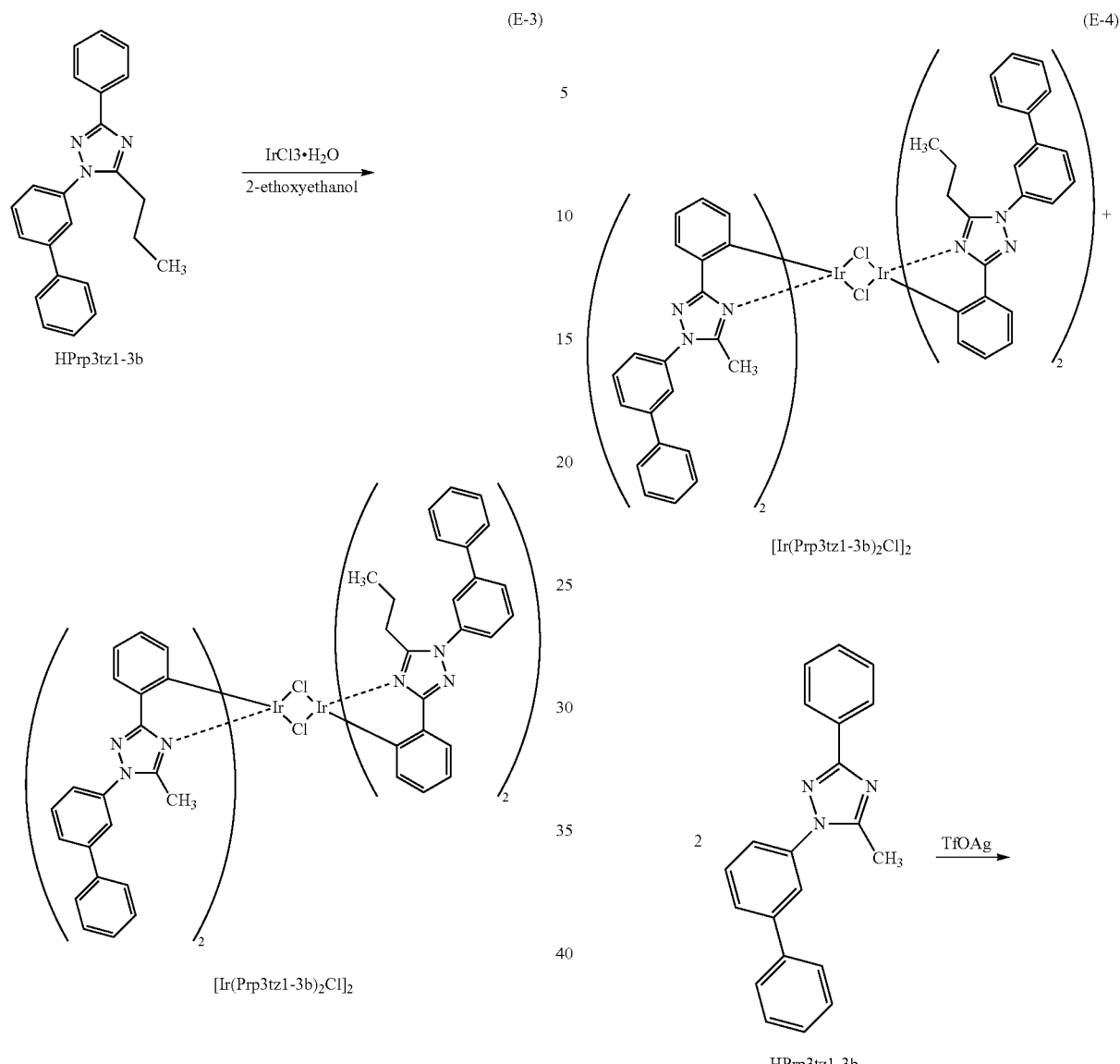

[Ir(Prp3tz1-3b)₂Cl]₂

Step 4: Synthesis of Tris[1-(3-biphenyl)-3-phenyl-5-propyl-1H-1,2,4-triazolato] iridium(III) (Abbreviation: [Ir(Prp3tz1-3b)₃])

Then, 1.3 g of [Ir(Prp3tz1-3b)₂Cl]₂ (abbreviation) which is the dinuclear complex obtained in Step 3 above, 3.6 g of HPrp3tz1-3b which is the ligand obtained in Step 2 above, and 0.79 g of silver trifluoromethanesulfonate (TfOAg) were put into a reaction container provided with a three-way cock and a cold tube and heated and stirred in a nitrogen atmosphere at 165° C. for 8 hours; then, the temperature was raised to 180° C. and stirring was performed for 31 hours. The obtained reaction mixture was dissolved in dichloromethane and suction filtration was carried out to remove insoluble matter. The obtained filtrate was concentrated and purification by silica gel column chromatography was performed. Dichloromethane was used as a developing solvent. A solid given by concentration of the obtained fraction was recrystallized with a mixed solvent of dichloromethane and hexane, so that [Ir(Prp3tz1-3b)₃] (abbreviation) was obtained (pale yellow powder, 7.5% yield). The synthesis scheme of Step 4 is shown in (E-4) below.

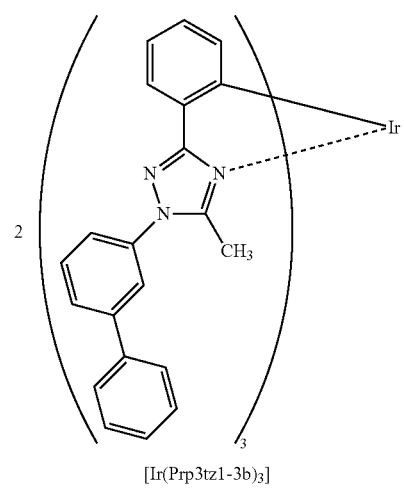

[Ir(Prp3tz1-3b)₃]

Figure 16:
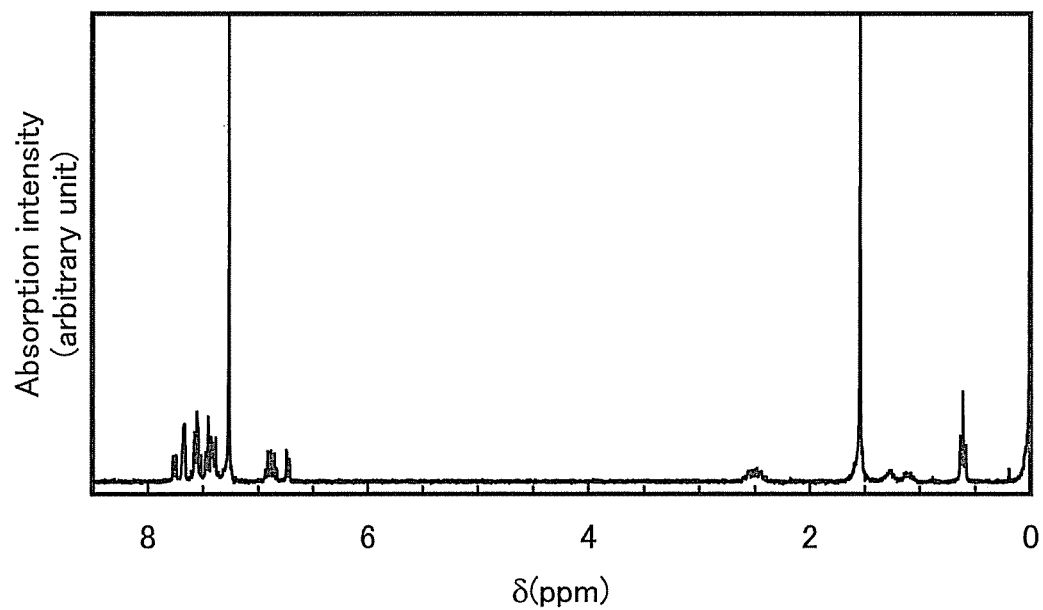
FIG. 16 is a $^1$H NMR chart of an organometallic complex represented by Structural Formula (111).

An analysis result by nuclear magnetic resonance spectrometry (¹H NMR) of the pale yellow powder obtained in Step 4 above is described below. The ¹H NMR chart is shown in FIG. 16. These results revealed that [Ir(Prp3tz1-3b)₃] (abbreviation), the organometallic complex of one embodiment of the present invention which is represented by Structural Formula (111), was obtained in Synthesis Example 5.

¹H NMR data of the obtained substance are as follows:

¹H-NMR. δ (CDCl₃): 0.61 (t, 9H), 1.05-1.31 (m, 6H), 2.39-2.60 (m, 6H), 6.73 (d, 3H), 6.83-6.93 (6H, m), 7.38-7.48 (m, 12H), 7.52-7.58 (m, 9H), 7.67-7.69 (m, 6H), 7.76 (3H, dd).

Figure 17:
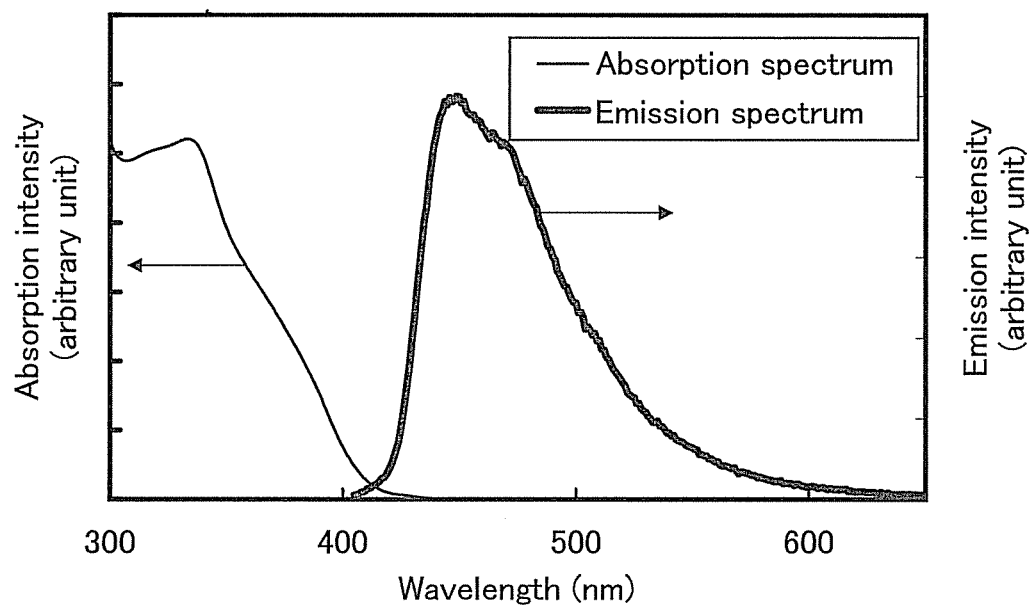
FIG. 17 shows an ultraviolet-visible absorption spectrum and an emission spectrum of an organometallic complex represented by Structural Formula (111) in a dichloromethane solution.

Next, an ultraviolet-visible absorption spectrum (hereinafter, simply referred to as absorption spectrum) and an emission spectrum of [Ir(Prp3tz1-3b)₃] (abbreviation) in a dichloromethane solution were measured. The absorption spectrum was measured with the use of an ultraviolet-visible light spectrophotometer (V-550, manufactured by JASCO Corporation) in the state where a dichloromethane solution (0.091 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.091 mmol/L) was put in a quartz cell at room temperature. FIG. 17 shows measurement results of the absorption spectrum and emission spectrum. The horizontal axis represents wavelength and the vertical axes represent absorption intensity and emission intensity. In FIG. 17, two solid lines are shown; a thin line represents the absorption spectrum, and a thick line represents the emission spectrum. Note that the absorption spectrum in FIG. 17 is a result obtained by subtraction of a measured absorption spectrum of only dichloromethane that was put in a quartz cell from the measured absorption spectrum of the dichloromethane solution (0.091 mmol/L) in a quartz cell.

As shown in FIG. 17, [Ir(Prp3tz1-3b)₃] (abbreviation), the organometallic complex of one embodiment of the present invention, has an emission peak at 449 nm, and blue light was observed from the dichloromethane solution.

Example 6

Synthesis Example 6

This example specifically illustrates a synthesis example of tris{3-[1-(2-methylphenyl)-5-propyl-1H-1,2,4-triazol-3-yl-κN4]-2-naphthalenyl-κC}iridium(III) (another name: tris[1-(2-methylphenyl)-3-(2-naphthyl)-5-propyl-1H-1,2,4-triazolato] iridium(III), abbreviation: [Ir(Prn3tz1-mp)₃]), the organometallic complex of one embodiment of the present invention which is represented by Structural Formula (116) in Embodiment 1. A structure of [Ir(Prn3tz1-mp)₃] (abbreviation) is shown below.

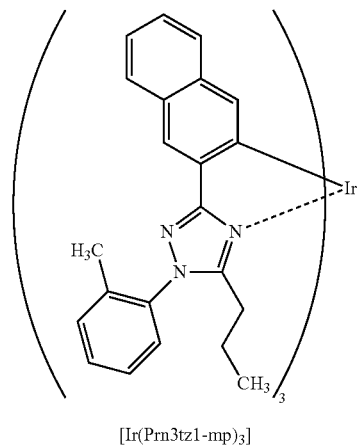

(116)

[Ir(Prn3tz1-mp)₃]

Step 1: Synthesis of N-(1-ethoxy-2-naphthylidene)butyramide

First, 5 g of ethyl 2-naphthalenecarboximidate hydrochloride, 50 mL of toluene, and 4.3 g of triethylamine (Et₃N) were put into a 300-mL three-neck flask and the mixture was stirred at room temperature for 10 minutes. With a 50-mL dropping funnel, a mixed solution of 2.3 g of butyryl chloride and 30 mL of toluene was added dropwise to this mixture, and the mixture was stirred at room temperature for 41.5 hours. After a predetermined time elapsed, the reaction mixture was suction-filtered, and the filtrate was concentrated to give N-(1-ethoxy-2-naphthylidene)butyramide (a yellow oily substance, 100% yield). The synthesis scheme of Step 1 is shown in (F-1) below.

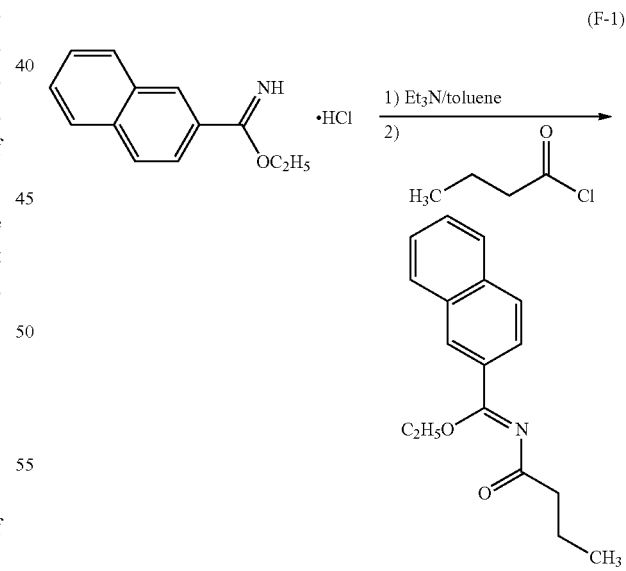

(F-1)

Step 2: Synthesis of 1-Methylphenyl-3-(2-naphthyl)-5-propyl-1H-1,2,4-triazole (Abbreviation: HPrn3tz1-mp)

Next, 4.0 g of o-tolyl hydrazine hydrochloride and 100 mL of carbon tetrachloride were put into a 300-mL three-neck flask, 3.0 g of triethylamine (Et₃N) was added dropwise to this mixture little by little, and the mixture was stirred at room temperature for 1 hour. After a predetermined time elapsed, 6.8 g of N-(1-ethoxy-2-naphthylidene)butyramide obtained in Step 1 above was added to the mixture, and the mixture was stirred at room temperature for 24 hours. After a predetermined time elapsed, water was added to the reacted solution and the mixture was stirred. The aqueous layer of this mixture was subjected to extraction with chloroform, and the obtained solution of the extract and the organic layer were combined and washed with saturated saline, and anhydrous magnesium sulfate was added for drying. The obtained mixture was gravity-filtered, and the filtrate was concentrated to give an oily substance. The obtained oily substance was purified by silica gel column chromatography. As the developing solvent, a mixed solvent of hexane and ethyl acetate in a ratio of 10:1 (v/v) was used. The obtained fraction was concentrated, so that 1-methylphenyl-3-(2-naphthyl)-5-propyl-1H-1,2,4-triazole (abbreviation: HPrn3tz1-mp) was obtained (a pale red solid, 36% yield). The synthesis scheme of Step 2 is shown in (F-2) below.

(F-2)

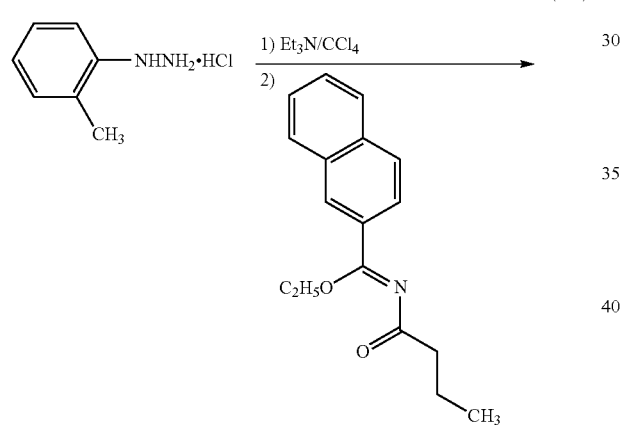

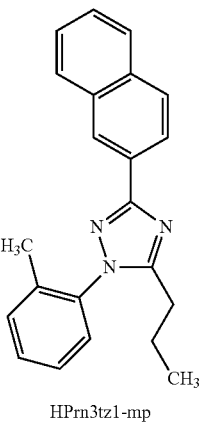

HPrn3tz1-mp

Step 3: Synthesis of Di-μ-chloro-tetrakis{3-[1-(2-methylphenyl)-5-propyl-1H-1,2,4-triazol-3-yl-κN4]-2-naphthalenyl-κC}diiridium(III) (Abbreviation: [Ir(Prn3tz1-mp)₂Cl]₂)

Then, 0.8 g of HPrn3tz1-mp which is the ligand obtained in Step 2 above, 0.35 g of iridium chloride hydrate, 12 mL of 2-ethoxyethanol, and 4 mL of water were put into a 50-mL recovery flask and the air in the flask was replaced with argon. This reaction container was subjected to microwaves under conditions of 100 W and 100° C. for 1 hour to cause a reaction. After a predetermined time elapsed, the obtained reaction mixture was suction-filtered and the obtained solid was washed with ethanol to give a dinuclear complex [Ir(Prn3tz1-mp)₂Cl]₂ (yellow powder, 93% yield). The synthesis scheme of Step 3 is shown in (F-3) below.

(F-3)

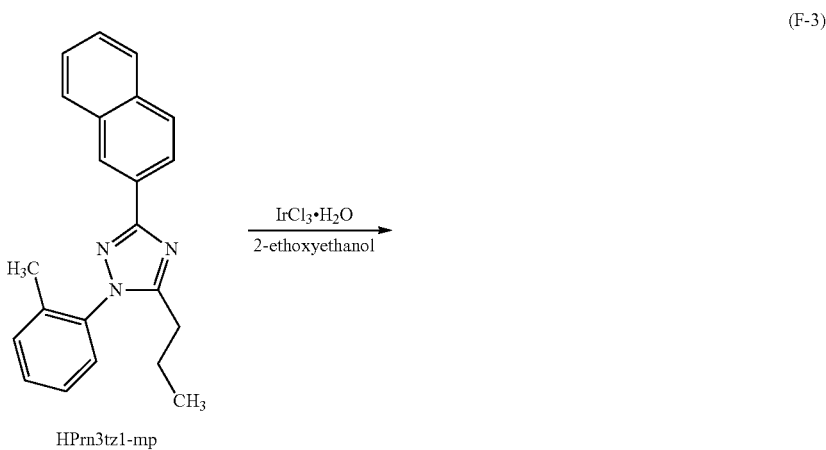

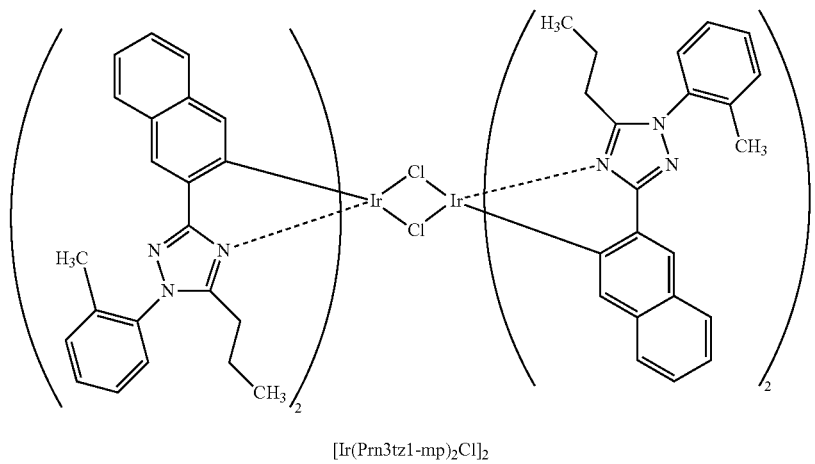

[Ir(Prn3tz1-mp)₂Cl]₂

Step 4: Synthesis of Tris{3-[1-(2-methylphenyl)-5-propyl-1H-1,2,4-triazol-3-yl-κN4]-2-naphthalenyl-κC}iridium(III) (Abbreviation: [Ir(Prn3tz1-mp)₃])

Then, 0.96 g of [Ir(Prn3tz1-mp)₂Cl]₂ which is the dinuclear complex obtained in Step 3 above, 2.1 g of HPrn3tz1-mp which is the ligand obtained in Step 2 above, and 0.56 g of silver trifluoromethanesulfonate (TfOAg) were put into a reaction container provided with a three-way cock and a cold tube, and the air in the flask was replaced with argon. The mixture was heated and stirred at 170° C. for 45 hours. The obtained mixture was dissolved in dichloromethane and suction filtration was carried out to remove insoluble solids. The obtained filtrate was washed with water and saturated saline, and anhydrous magnesium sulfate was added to the organic layer for drying. This mixture was gravity-filtered, and the filtrate was concentrated to give an oily substance. This oily substance was purified by silica gel column chromatography. As the developing solvent, a mixed solvent of dichloromethane and hexane in a ratio of 5:1 (v/v) was used. The obtained fraction was concentrated to obtain a solid. This solid was washed with ethanol, and the obtained solid was recrystallized with a mixed solvent of dichloromethane and ethanol to give [Ir(Prn3tz1-mp)₃] (abbreviation), the organometallic complex of one embodiment of the present invention (yellow powder, 10% yield). The synthesis scheme of Step 4 is shown in (F-4) below.

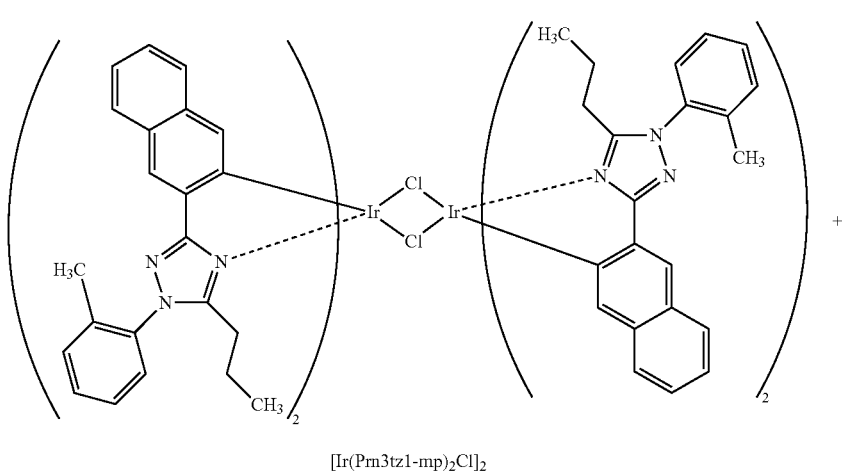

(F-4)

[Ir(Prn3tz1-mp)₂Cl]₂

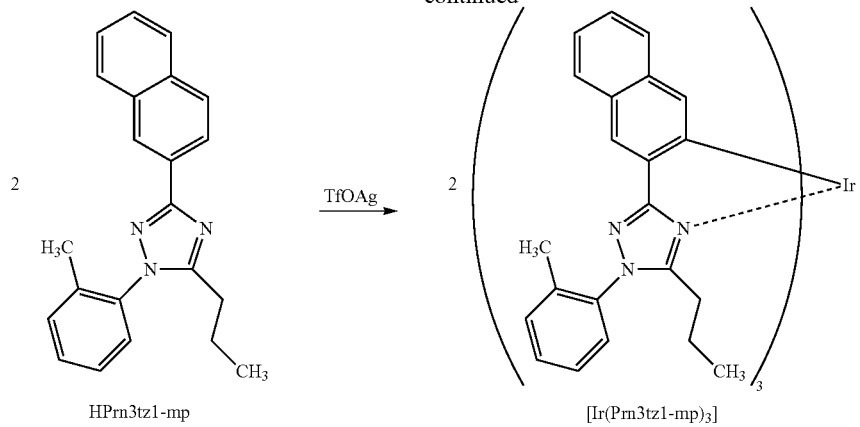

HPrn3tz1-mp → [Ir(Prn3tz1-mp)₃]

(TfOAg)

Figure 18:
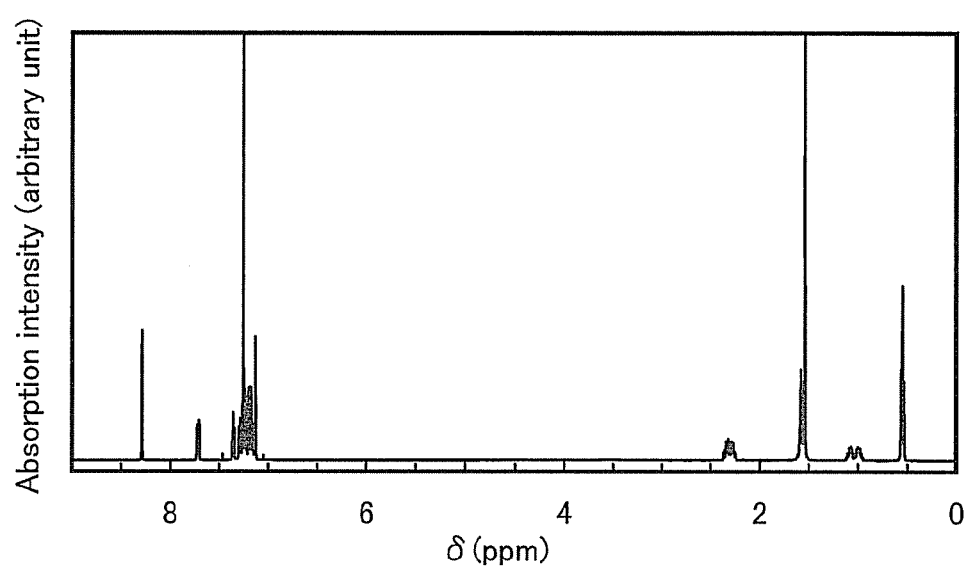
FIG. 18 is a $^1$H NMR chart of an organometallic complex represented by Structural Formula (116).

An analysis result by nuclear magnetic resonance spectrometry (¹H NMR) of the pale yellow powder obtained in Step 4 above is described below. The ¹H NMR chart is shown in FIG. 18. These results revealed that [Ir(Prn3tz1-mp)₃] (abbreviation), the organometallic complex of one embodiment of the present invention which is represented by Structural Formula (116), was obtained in Synthesis Example 6.

¹H NMR data of the obtained substance are as follows:

¹H-NMR. δ (CDCl₃): 0.54 (t, 9H), 0.93-1.13 (m, 6H), 1.58 (s, 9H), 2.24-2.37 (m, 6H), 7.13-7.29 (m, 21H), 7.35 (t, 3H), 7.71 (d, 3H), 8.29 (s, 3H).

Figure 19:
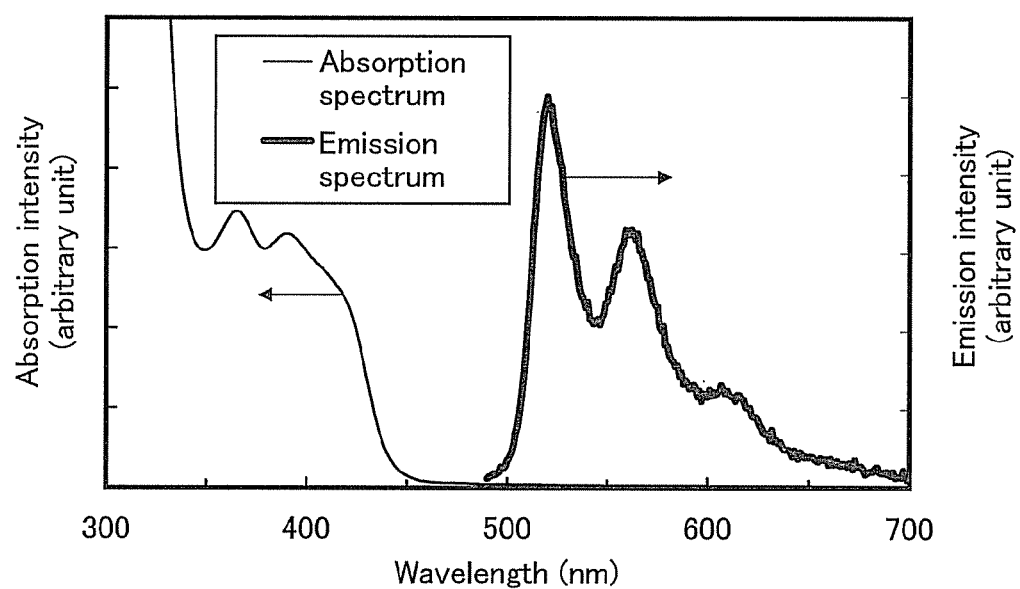
FIG. 19 shows an ultraviolet-visible absorption spectrum and an emission spectrum of an organometallic complex represented by Structural Formula (116) in a dichloromethane solution.

Next, an ultraviolet-visible absorption spectrum (hereinafter, simply referred to as absorption spectrum) and an emission spectrum of [Ir(Prn3tz1-mp)₃] (abbreviation) in a dichloromethane solution were measured. The absorption spectrum was measured with the use of an ultraviolet-visible light spectrophotometer (V-550, manufactured by JASCO Corporation) in the state where a dichloromethane solution (0.087 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.087 mmol/L) was put in a quartz cell at room temperature. FIG. 19 shows measurement results of the absorption spectrum and emission spectrum. The horizontal axis represents wavelength and the vertical axes represent absorption intensity and emission intensity. In FIG. 19, two solid lines are shown; a thin line represents the absorption spectrum, and a thick line represents the emission spectrum. Note that the absorption spectrum in FIG. 19 is a result obtained by subtraction of a measured absorption spectrum of only dichloromethane that was put in a quartz cell from the measured absorption spectrum of the dichloromethane solution (0.087 mmol/L) in a quartz cell.

As shown in FIG. 19, [Ir(Prn3tz1-mp)₃] (abbreviation), the organometallic complex of one embodiment of the present invention, has emission peaks at 520 nm and 562 nm, and yellow light was observed from the dichloromethane solution.

Example 7

Synthesis Example 7

This example specifically illustrates a synthesis example of tris{4-phenyl-2-[1-(2-methylphenyl)-5-propyl-1H-1,2,4-triazol-3-yl-κN4]phenyl-κC}iridium(III) (another name: tris [3-(3-biphenyl)-1-(2-methylphenyl)-5-propyl-1H-1,2,4-triazolato] abbreviation: [Ir(Pr5b3tz1-mp)₃]), the organometallic complex of one embodiment of the present invention which is represented by Structural Formula (118) in Embodiment 1. A structure of [Ir(Pr5b3tz1-mp)₃] (abbreviation) is shown below.

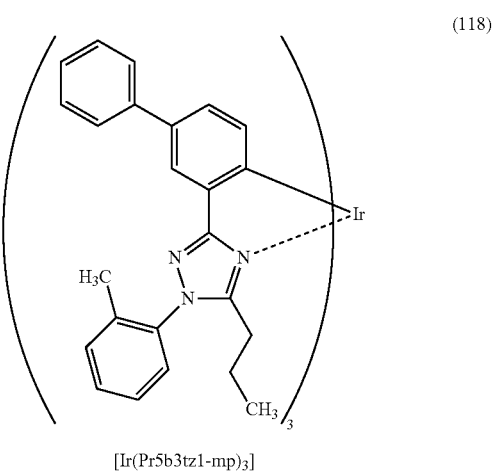

(118)

[Ir(Pr5b3tz1-mp)₃]

Step 1: Synthesis of N-(1-ethoxy-3-bromobenzylidene)butyramide

First, 10 g of ethyl 3-bromobenzimidate hydrochloride, 100 mL of toluene, and 8.9 g of triethylamine (Et₃N) were put into a 300-mL three-neck flask and the mixture was stirred at room temperature for 10 minutes. With a 50-mL dropping funnel, a mixed solution of 4.7 g of butyryl chloride and 30 mL of toluene was added dropwise to this mixture, and the mixture was stirred at room temperature for 24 hours. After a predetermined time elapsed, the reaction mixture was suction-filtered, and the filtrate was concentrated to give N-(1-ethoxy-3-bromobenzylidene)butyramide (a yellow oily substance, 93% yield). The synthesis scheme of Step 1 is shown in (G-1) below.

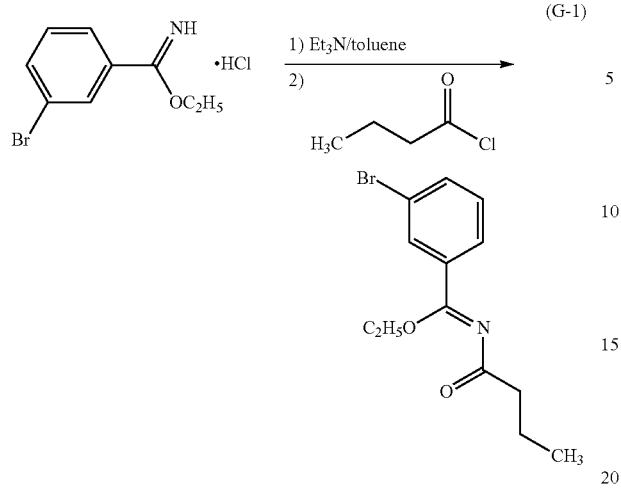

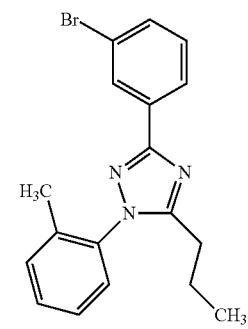

Step 3: Synthesis of 3-(3-Biphenyl)-1-(2-methylphenyl)-5-propyl-1H-1,2,4-triazole (Abbreviation: HPr5b3tz1-mp)

Next, 12 g of 3-(3-bromophenyl)-1-(2-methylphenyl)-5-propyl-1H-1,2,4-triazole obtained in Step 2 above, 4.8 g of phenylboronic acid, 0.30 g of tri(ortho-tolyl)phosphine, 100 mL of toluene, 15 mL of ethanol, and 39 mL of 2M aqueous solution of potassium carbonate were put into a 200-mL three-neck flask, and the air in the flask was replaced with nitrogen. To this mixture was added 0.073 g (0.33 mmol) of palladium(II) acetate, and the mixture was heated and stirred at 80° C. for 10 hours. The aqueous layer of the obtained reacted solution was subjected to extraction with toluene, and the obtained solution of the extract and the organic layer were combined and washed with a saturated aqueous solution of sodium hydrogen carbonate and saturated saline. Anhydrous magnesium sulfate was added to the organic layer for drying, and the resulting mixture was gravity-filtered to give filtrate. The obtained filtrate was concentrated to give an oily substance. This oily substance was purified by flash column chromatography. As the developing solvent, a mixed solvent of hexane and ethyl acetate in a ratio of 5:1 (v/v) was used. The obtained fraction was concentrated, so that 3-(3-biphenyl)-1-(2-methylphenyl)-5-propyl-1H-1,2,4-triazole (abbreviation: HPr5b3tz1-mp) was obtained (a pale yellow oily substance, 84% yield). The synthesis scheme of Step 3 is shown in (G-3) below.

Step 2: Synthesis of 3-(3-Bromophenyl)-1-(2-methylphenyl)-5-propyl-1H-1,2,4-triazole Next, 6.5 g of o-tolyl hydrazine hydrochloride and 100 mL of carbon tetrachloride were put into a 200-mL three-neck flask, 4.1 g of triethylamine (Et$_3$N) was added dropwise to this mixture little by little, and the mixture was stirred at room temperature for 1 hour. After a predetermined time elapsed, 12 g of N-(1-ethoxy-3-bromobenzylidene)butyramide obtained in Step 1 above was added to the mixture, and the mixture was stirred at room temperature for 48 hours. After the reaction, water was added to the reaction mixture and the aqueous layer was subjected to extraction with chloroform. The organic layer and the obtained solution of the extract were combined and washed with water and saturated saline. Anhydrous magnesium sulfate was added to the organic layer for drying and the obtained mixture was concentrated to give an oily substance. The obtained oily substance was purified by flash column chromatography. As the developing solvent, a mixed solvent of hexane and ethyl acetate in a ratio of 5:1 (v/v) was used. The obtained fraction was concentrated to give 3-(3-bromophenyl)-1-(2-methylphenyl)-5-propyl-1H-1,2,4-triazole (a red oily substance, 80% yield). The synthesis scheme of Step 2 is shown in (G-2) below.

Step 4: Synthesis of Di-μ-chloro-tetrakis{4-phenyl-2-[1-(2-methylphenyl)-5-propyl-1H-1,2,4-triazol-3-yl-κN4]phenyl-κC}diiridium(III) (Abbreviation: [Ir(Pr5b3tz1-mp)₂Cl]₂)

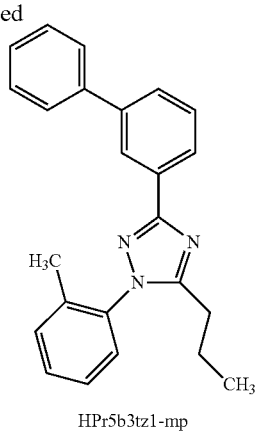

HPr5b3tz1-mp

Then, 1.5 g of HPr5b3tz1-mp which is the ligand obtained in Step 3 above, 0.61 g of iridium chloride hydrate, 12 mL of 2-ethoxyethanol, and 4 mL of water were put into a 50-mL recovery flask and the air in the flask was replaced with argon. This reaction container was subjected to microwaves under conditions of 100 W and 100° C. for 1.5 hour to cause a reaction. The obtained reaction mixture was suction-filtered and the obtained solid was washed with ethanol to give a dinuclear complex [Ir(Pr5b3tz1-mp)₂Cl]₂ (yellow brown powder, 8.4% yield). The synthesis scheme of Step 4 is shown in (G-4) below.

(G-4)

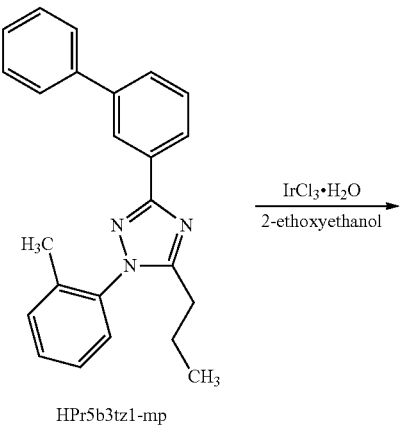

HPr5b3tz1-mp

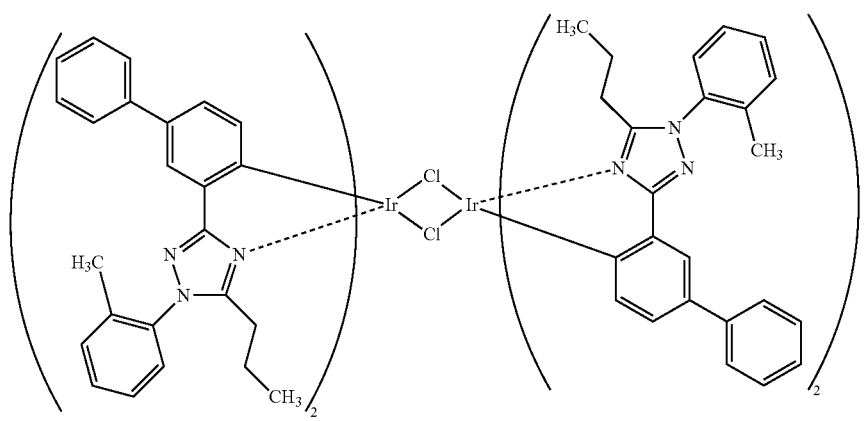

[Ir(Pr5b3tz1-mp)₂Cl]₂

Step 5: Synthesis of Tris{4-phenyl-2-[1-(2-methylphenyl)-5-propyl-1H-1,2,4-triazol-3-yl-κN4]phenyl-κC}iridium(III) (Abbreviation: [Ir(Pr5b3tz1-mp)$_3$])

Then, 0.60 g of [Ir(Pr5b3tz1-mp)$_2$Cl]$_2$ which is the dinuclear complex obtained in Step 4 above, 1.7 g of HPr5b3tz1-mp which is the ligand, and 0.39 g of silver trifluoromethanesulfonate (TfOAg) were put into a reaction container provided with a three-way cock and a cold tube, and the mixture was heated and stirred in a nitrogen atmosphere at 170° C. for 42 hours. The obtained reaction mixture was dissolved in dichloromethane and insoluble solids were removed. The obtained filtrate was washed with water and saturated saline, and anhydrous magnesium sulfate was then added to the organic layer for drying. The obtained mixture was gravity-filtered, and the filtrate was concentrated to give a solid. This solid was purified by silica gel column chromatography. As the developing solvent, a mixed solvent of dichloromethane and hexane in a ratio of 2:1 (v/v) was used. The obtained fraction was concentrated to obtain a solid. This solid was recrystallized with a mixed solvent of dichloromethane and ethanol to give [Ir(Pr5b3tz1-mp)$_3$] (abbreviation), the organometallic complex of one embodiment of the present invention (pale yellow powder, 48% yield). The synthesis scheme of Step 5 is shown in (G-5) below.

Figure 20:
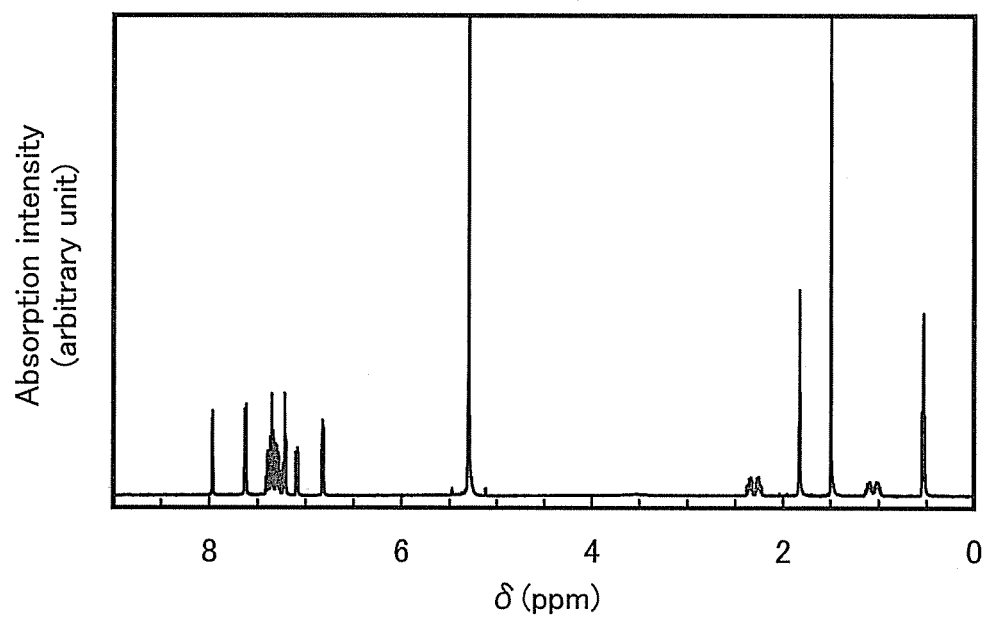
FIG. 20 is a $^1$H NMR chart of an organometallic complex represented by Structural Formula (118).

An analysis result by nuclear magnetic resonance spectrometry ($^1$H NMR) of the pale yellow powder obtained in Step 5 above is described below. The $^1$H NMR chart is shown in FIG. 20. These results revealed that [Ir(Pr5b3tz1-mp)$_3$], the organometallic complex of one embodiment of the present invention which is represented by Structural Formula (118), was obtained in Synthesis Example 7.

$^1$H-NMR. δ (CD$_2$Cl$_2$): 0.54 (t, 9H), 0.99-1.14 (m, 6H), 1.83 (s, 9H), 2.22-2.38 (m, 6H), 6.82 (d, 3H), 7.09 (dd, 3H), 7.21-7.23 (t, 6H), 7.27-7.41 (m, 15H), 7.62 (d, 6H), 7.97 (d, 3H).

Figure 21:
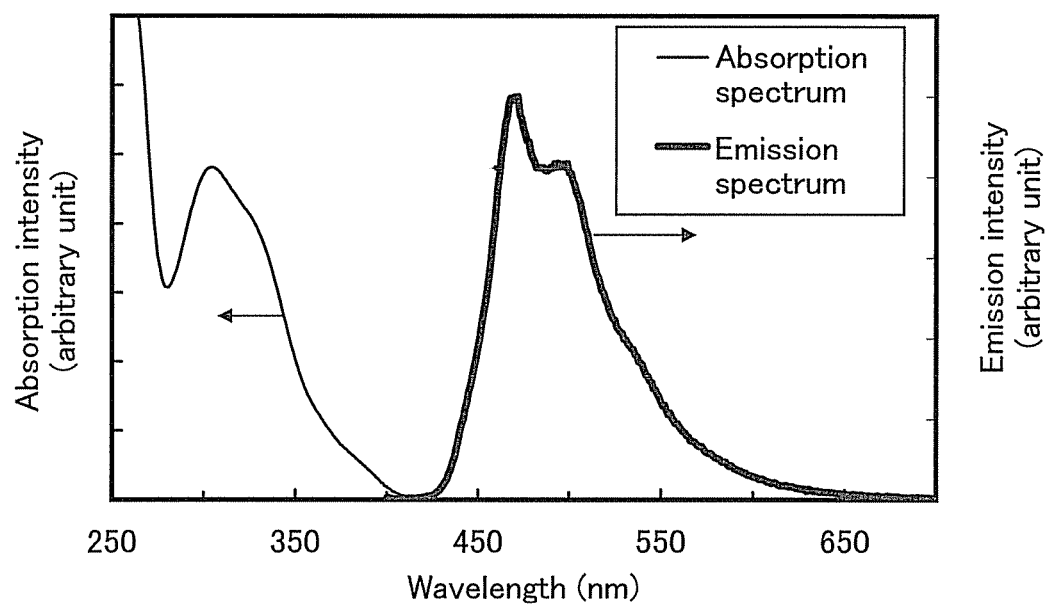
FIG. 21 shows an ultraviolet-visible absorption spectrum and an emission spectrum of an organometallic complex represented by Structural Formula (118) in a dichloromethane solution.

Next, an ultraviolet-visible absorption spectrum (hereinafter, simply referred to as absorption spectrum) and an emission spectrum of [Ir(Pr5b3tz1-mp)$_3$] (abbreviation) in a dichloromethane solution were measured. The absorption spectrum was measured with the use of an ultraviolet-visible light spectrophotometer (V-550, manufactured by JASCO Corporation) in the state where a dichloromethane solution (0.041 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.041 mmol/L) was put in a quartz cell at room temperature. FIG. 21 shows measurement results of the absorption spectrum and emission spectrum. The horizontal axis represents wavelength and the ver-

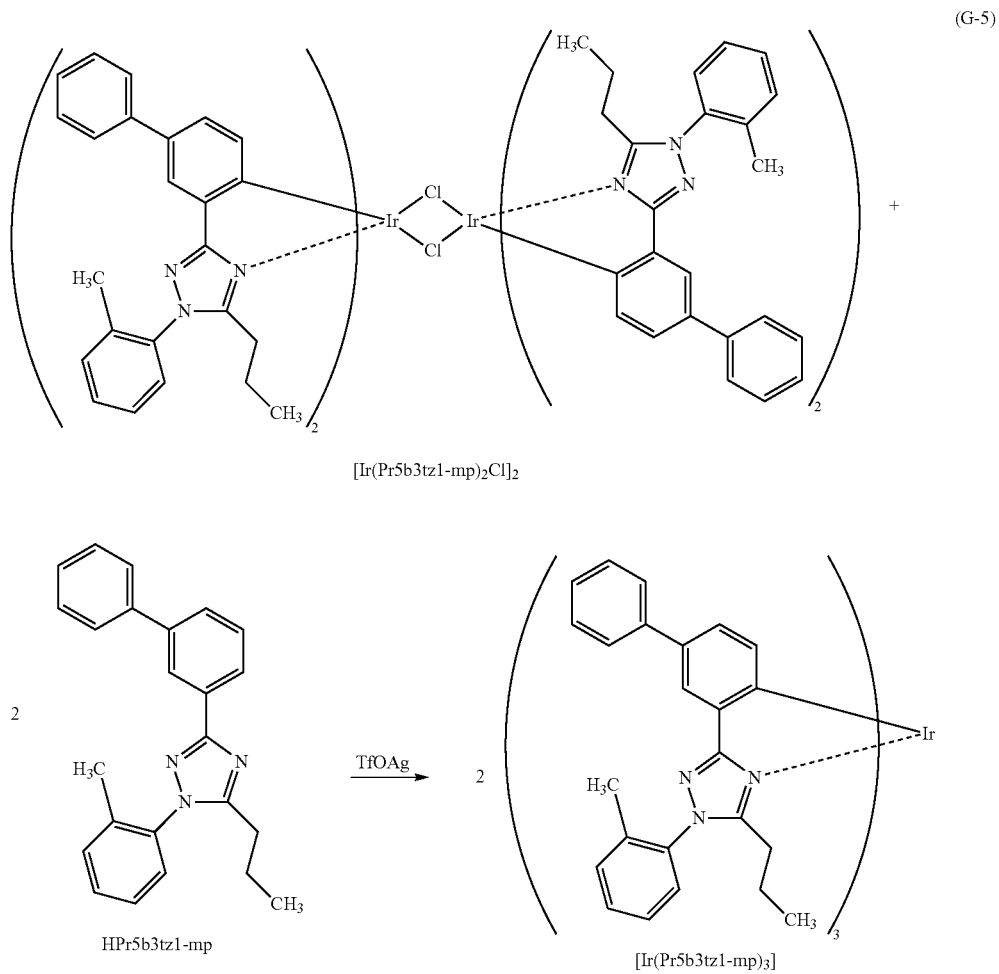

(G-5)

tical axes represent absorption intensity and emission intensity. In FIG. 21, two solid lines are shown; a thin line represents the absorption spectrum, and a thick line represents the emission spectrum. Note that the absorption spectrum in FIG. 21 is a result obtained by subtraction of a measured absorption spectrum of only dichloromethane that was put in a quartz cell from the measured absorption spectrum of the dichloromethane solution (0.041 mmol/L) in a quartz cell.

As shown in FIG. 21, [Ir(Pr5b3tz1-mp)$_3$], the organometallic complex of one embodiment of the present invention, has emission peaks at 469 nm and 497 nm, and light-blue light was observed from the dichloromethane solution.

Example 8

In this example, Light-emitting Element 1 in which the organometallic complex represented by Structural Formula (116) in Embodiment 1 and Example 6 is used for a light-emitting layer was evaluated. Chemical formulae of materials used in this example are shown below.

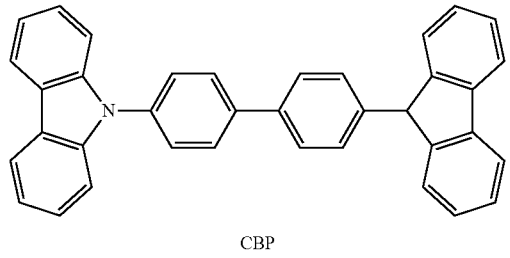

CBP

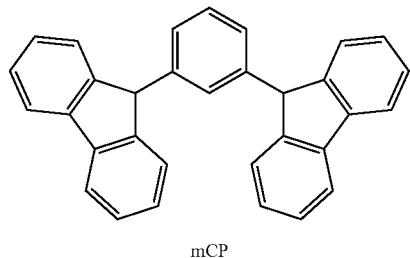

mCP

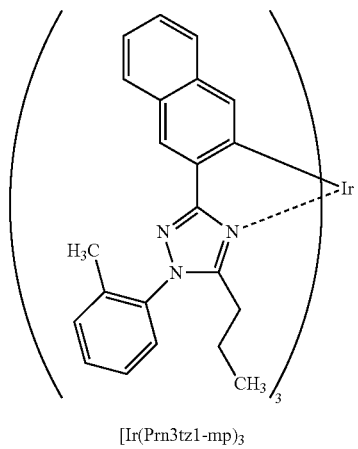

[Ir(Prn3tz1-mp)$_3$]

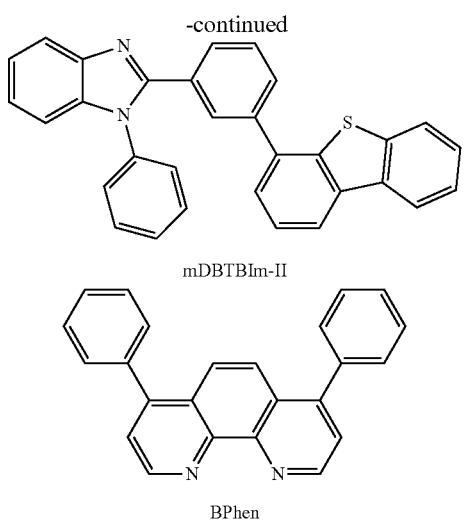

mDBTBIm-II

BPhen

Figure 22:
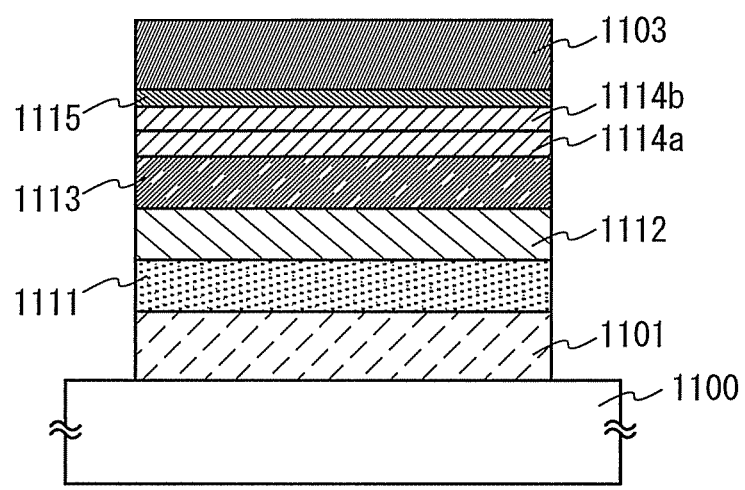
FIG. 22 illustrates a light-emitting element of an example.

Light-emitting Element 1 is described with reference to FIG. 22. A method for fabricating Light-emitting Element 1 of this example is described below.

(Light-Emitting Element 1)

First, silicon, or an indium oxide-tin oxide compound containing silicon oxide (ITO-SiO$_2$, hereinafter abbreviated to ITSO) was deposited by a sputtering method over a substrate 1100, so that a first electrode 1101 was formed. Note that the composition ratio of the target used was In$_2$O$_3$:SnO$_2$:SiO$_2$=85:10:5 [wt %]. The thickness of the first electrode 1101 was 110 nm and the electrode area was 2 mm×2 mm. Here, the first electrode 1101 is an electrode that functions as an anode of the light-emitting element.

Next, as pretreatment for forming the light-emitting element over the substrate 1100, the surface of the substrate was washed with water, baked at 200° C. for 1 hour, and subjected to UV ozone treatment for 370 seconds.

After that, the substrate 1100 was transferred into a vacuum evaporation apparatus where the pressure had been reduced to approximately 10$^{-4}$ Pa, and subjected to vacuum baking at 170° C. for 30 minutes in a heating chamber of the vacuum evaporation apparatus, and then the substrate 1100 was cooled down naturally for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about 10$^{-4}$ Pa. Then, 4,4'-di(N-carbazolyl)biphenyl (abbreviation: CBP) and molybdenum oxide were co-evaporated to form a hole-injection layer 1111 on the first electrode 1101. The thickness of the hole-injection layer 1111 was 60 nm, and the weight ratio of CBP (abbreviation) to molybdenum oxide was adjusted to 4:2 (=CBP:molybdenum oxide). Note that the co-evaporation method refers to an evaporation method in which evaporation is carried out from a plurality of evaporation sources at the same time in one treatment chamber.

Next, on the hole-injection layer 1111, a film of 1,3-bis(N-carbazolyl)benzene (abbreviation: mCP) was formed to a thickness of 20 nm, whereby a hole-transport layer 1112 was formed.

Further, mCP (abbreviation) and tris{3-[1-(2-methylphenyl)-5-propyl-1H-1,2,4-triazol-3-yl-κN4]-2-naphthalenyl-κC}iridium(III), (another name: tris[1-(2-methylphenyl)-3-(2-naphthyl)-5-propyl-1H-1,2,4-triazolato]iridium(III), abbreviation: [Ir(Prn3tz1-mp)$_3$]) synthesized in Example 6 were co-evaporated to form a light-emitting layer 1113 on the hole-transport layer 1112. Here, the weight ratio of mCP (abbreviation) to [Ir(Prn3tz1-mp)$_3$] (abbreviation) was adjusted to 1:0.06 (=mCP:[Ir(Prn3tz1-mp)$_3$]). The thickness of the light-emitting layer 1113 was 30 nm.

Note that [Ir(Prn3tz1-mp)$_3$] (abbreviation) is an organometallic complex of one embodiment of the present invention and is a guest material (dopant) in the light-emitting layer 1113.

Next, on the light-emitting layer 1113, a film of 2-[3-(dibenzothiophen-4-yl)phenyl]-1-phenyl-1H-benzimidazole (abbreviation: mDBTBIm-II) was formed to a thickness of 20 nm to form a first electron-transport layer 1114a.

After that, on the first electron-transport layer 1114a, a bathophenanthroline (abbreviation: BPhen) film was formed to a thickness of 15 nm, whereby a second electron-transport layer 1114b was formed.

Further, on the second electron-transport layer 1114b, a lithium fluoride (LiF) film was formed to a thickness of 1 nm by evaporation, whereby an electron-injection layer 1115 was formed.

Lastly, an aluminum film was formed to a thickness of 200 nm by evaporation as a second electrode 1103 functioning as a cathode. Thus, Light-emitting Element 1 of this example was fabricated.

Table 1 shows an element structure of Light-emitting Element 1 formed as described above.

TABLE 1

| | First Electrode | Hole-injection Layer | Hole-transport Layer | Light-emitting Layer | First Electron-transport Layer | Second Electron-transport Layer | Electron-injection Layer | Second Electrode |
|---|---|---|---|---|---|---|---|---|
| Light-emitting Element 1 | ITSO 110 nm | CBP:MoOx (=4:2) 60 nm | mCP 20 nm | mCP:Ir(Prn3tz1-mp)$_3$ (=1:0.06) 30 nm | mDBTBIm-II 20 nm | BPhen 15 nm | LiF 1 nm | Al 200 nm |

Then, in a glove box containing a nitrogen atmosphere, Light-emitting Element 1 was sealed so as not to be exposed to the air (specifically, a sealant was applied onto an outer edge of the element and heat treatment was performed at 80° C. for 1 hour at the time of sealing). After that, operation characteristics of Light-emitting Element 1 were measured. Note that the measurement was carried out at room temperature (in an atmosphere kept at 25° C.).

Figure 23:
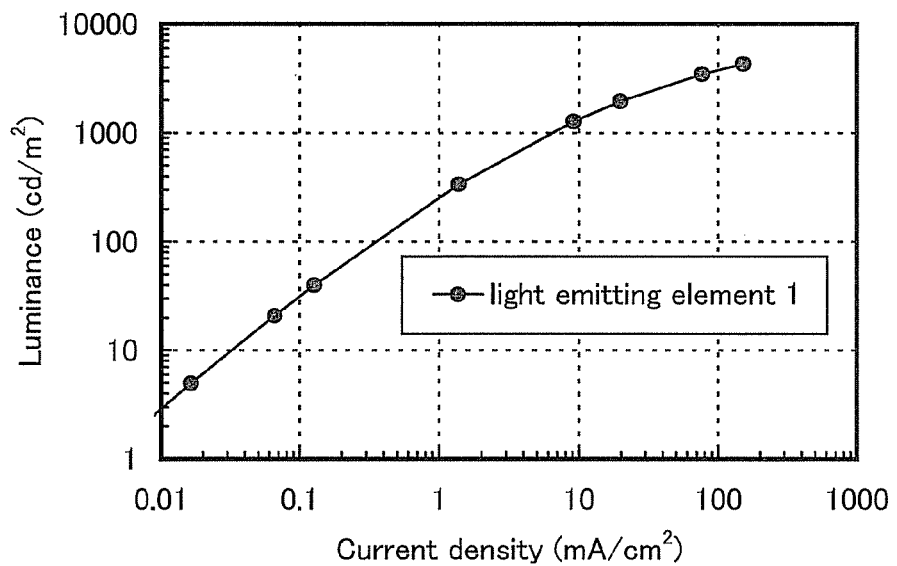
FIG. 23 shows current density vs. luminance characteristics of Light-emitting Element 1.
Figure 24:
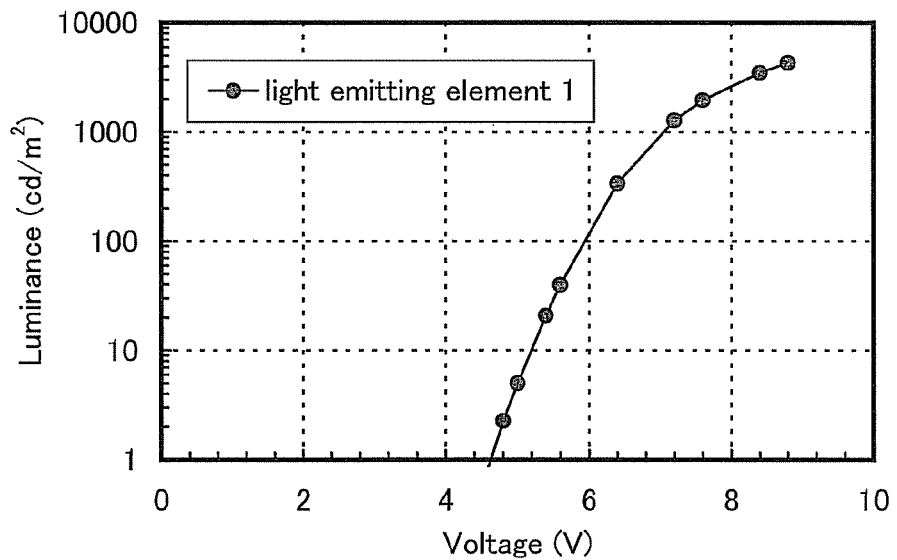
FIG. 24 shows voltage vs. luminance characteristics of Light-emitting Element 1.
Figure 25:
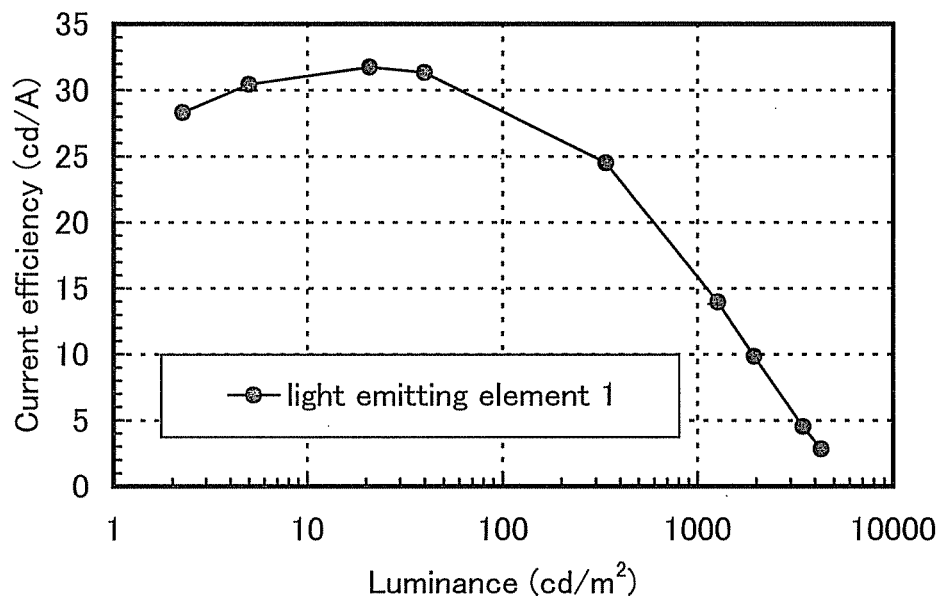
FIG. 25 shows luminance vs. current efficiency characteristics of Light-emitting Element 1.
Figure 26:
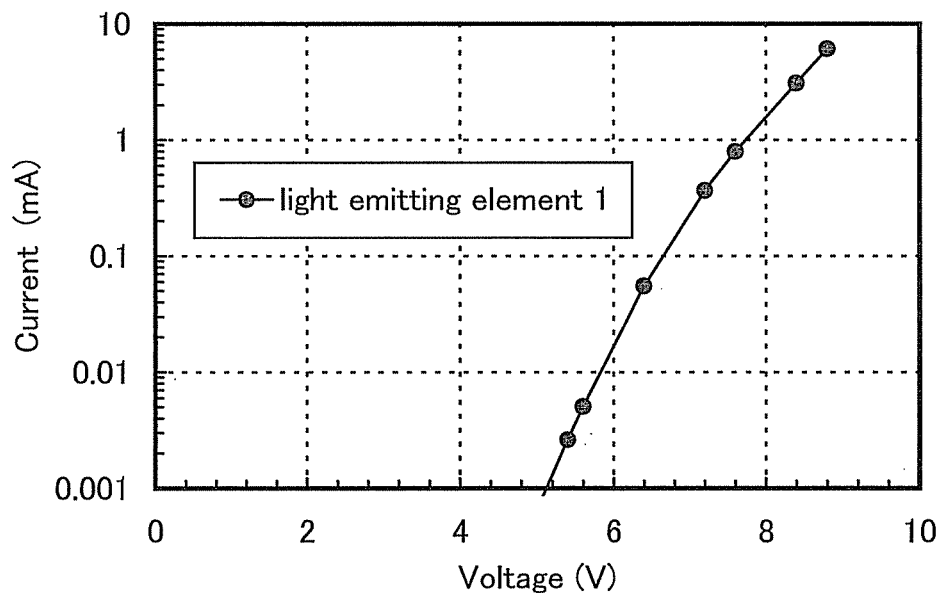
FIG. 26 shows voltage vs. current characteristics of Light-emitting Element 1.

FIG. 23 shows current density vs. luminance characteristics of Light-emitting Element 1. In FIG. 23, the horizontal axis represents current density (mA/cm$^2$) and the vertical axis represents luminance (cd/m$^2$). Further, FIG. 24 shows voltage vs. luminance characteristics of Light-emitting Element 1. In FIG. 24, the horizontal axis represents voltage (V) and the vertical axis represents luminance (cd/m$^2$). In addition, FIG. 25 shows luminance vs. current efficiency characteristics of Light-emitting Element 1. In FIG. 25, the horizontal axis represents luminance (cd/m$^2$) and the vertical axis represents current efficiency (cd/A). In addition, FIG. 26 shows voltage vs. current characteristics of Light-emitting Element 1. In FIG. 26, the horizontal axis represents voltage (V) and the vertical axis represents current (mA).

FIG. 23 and FIG. 25 show that Light-emitting Element 1 is a light-emitting element with high efficiency. Further, FIG. 23, FIG. 24, and FIG. 26 show that Light-emitting Element 1 is a light-emitting element with low drive voltage and low power consumption.

Next, Table 2 shows the voltage (V), current density (mA/cm$^2$), CIE chromaticity coordinates (x, y), luminance (cd/m$^2$), current efficiency (cd/A), and external quantum efficiency (%) of Light-emitting Element 1 at a luminance of 1275 cd/m$^2$.

TABLE 2

| | Voltage (V) | Current Density (mA/cm$^2$) | CIE Chromaticity Coordinates | | Luminance (cd/m$^2$) | Current Efficiency (cd/A) | External Quantum Efficiency (%) |
|---|---|---|---|---|---|---|---|
| | | | x | y | | | |
| Light-emitting Element 1 | 7.2 | 9.1 | 0.37 | 0.61 | 1275 | 14 | 4.2 |

Figure 27:
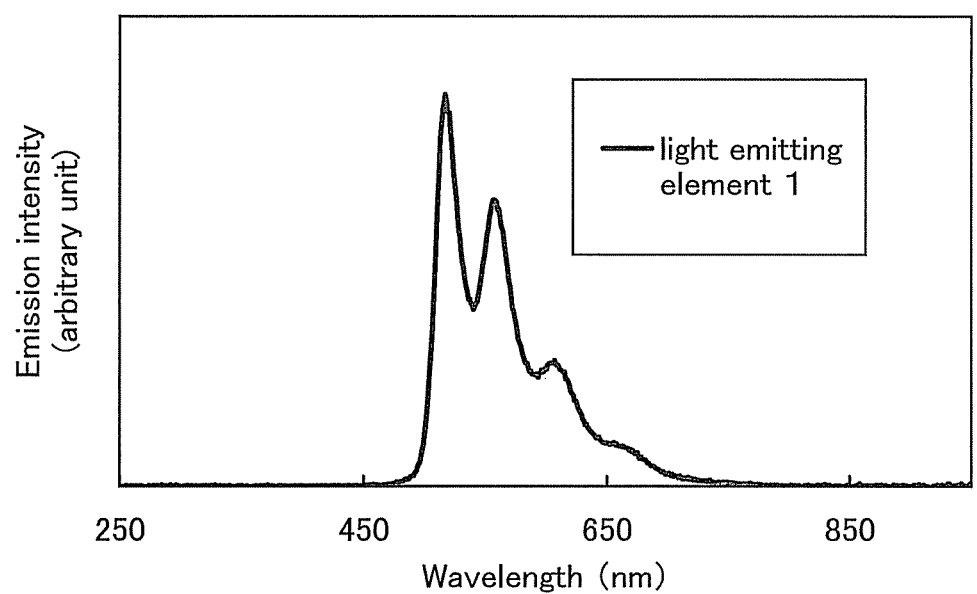
FIG. 27 shows an emission spectrum of Light-emitting Element 1.

FIG. 27 shows an emission spectrum when a current was supplied at a current density of 2.5 mA/cm$^2$ to Light-emitting Element 1. As shown in FIG. 27, the emission spectrum of Light-emitting Element 1 has peaks at 517 nm, 557 nm, and 609 nm.

In addition, as shown in Table 2, the CIE chromaticity coordinates of Light-emitting Element 1 were (x, y)=(0.37, 0.61) at a luminance of 1275 cd/m$^2$. These results show that light originating from the dopant was obtained.

As described above, it was shown that Light-emitting Element 1 in which [Ir(Prn3tz1-mp)$_3$] (abbreviation) which is an organometallic complex of one embodiment of the present invention is used for the light-emitting layer can efficiently emit light in a wavelength band of blue-green. This indicates that [Ir(Prn3tz1-mp)$_3$] (abbreviation) can be favorably used as a guest material of a light-emitting material which emits light in a wavelength band of blue to yellow.

Example 9

In this example, Light-emitting Element 2 having a different structure from Light-emitting Element 1 described in Example 8 was evaluated. Chemical formulae of materials used in this example are shown below.

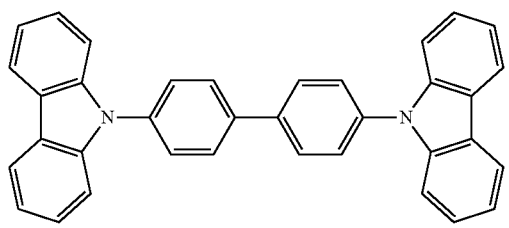

CBP

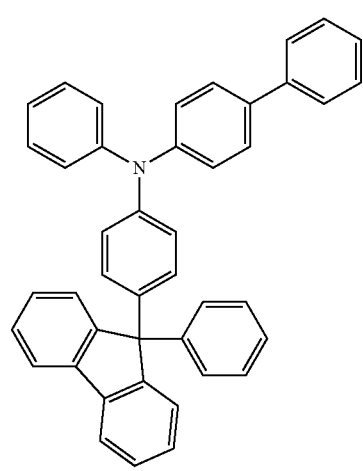

BPAFLP

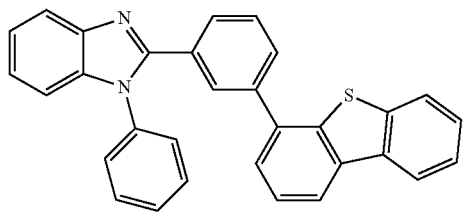

mDBTBIm-II

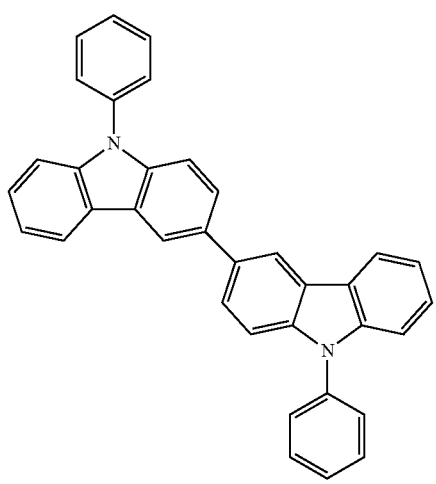

PCCP

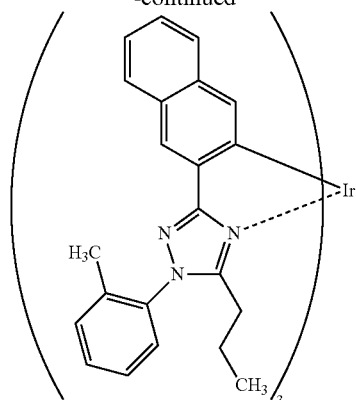

[Ir(Prn3tz1-mp)₃]

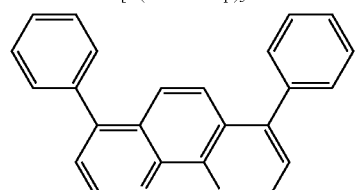

BPhen

Figure 28:
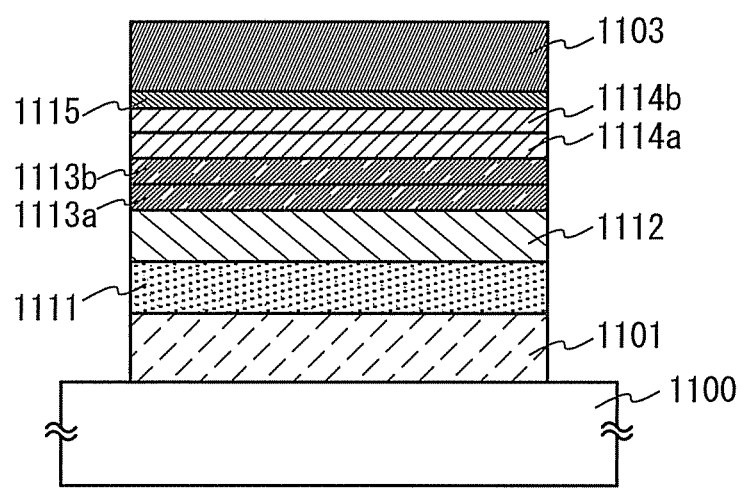
FIG. 28 illustrates a light-emitting element of an example.

Light-emitting Element 2 is described with reference to FIG. 28. A method for fabricating Light-emitting Element 2 of this example is described below.

(Light Emitting Element 2)

First, silicon, or an indium oxide-tin oxide compound containing silicon oxide (ITO-SiO₂, hereinafter abbreviated to ITSO) was deposited by a sputtering method over the substrate 1100, so that the first electrode 1101 was formed. Note that the composition ratio of the target used was $In_2O_3:SnO_2:SiO_2=85:10:5$ [wt %]. The thickness of the first electrode 1101 was 110 nm and the electrode area was 2 mm×2 mm. Here, the first electrode 1101 is an electrode that functions as an anode of the light-emitting element.

Next, as pretreatment for forming the light-emitting element over the substrate 1100, the surface of the substrate was washed with water, baked at 200° C. for 1 hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down naturally for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, 4,4'-di(N-carbazolyl)biphenyl (abbreviation: CBP) and molybdenum oxide were co-evaporated to form the hole-injection layer 1111 on the first electrode 1101. The thickness of the hole-injection layer 1111 was 60 nm, and the weight ratio of CBP (abbreviation) to molybdenum oxide was adjusted to 4:2 (=CBP:molybdenum oxide).

Next, 4-phenyl-4'-(9-phenylfluoren-9-yl)triphenylamine (abbreviation: BPAFLP) was formed to a thickness of 20 nm on the hole-injection layer 1111, whereby the hole-transport layer 1112 was formed.

Further, 2-[3-(dibenzothiophen-4-yl)phenyl]-1-phenyl-1H-benzimidazole (abbreviation: mDBTBIm-II), 9-phenyl-9H-3-(9-phenyl-9H-carbazol-3-yl)-carbazole (abbreviation: PCCP), and tris{3-[1-(2-methylphenyl)-5-propyl-1H-1,2,4-triazol-3-yl-κN4]-2-naphthalenyl-κC}iridium(III), (another name: tris[1-(2-methylphenyl)-3-(2-naphthyl)-5-propyl-1H-1,2,4-triazolato] abbreviation: [Ir(Prn3tz1-mp)$_3$]) synthesized in Example 6 were co-evaporated to form a first light-emitting layer 1113a on the hole-transport layer 1112. Here, the weight ratio of mDBTBIm-II (abbreviation) to PCCP (abbreviation) and [Ir(Prn3tz1-mp)$_3$] (abbreviation) was adjusted to 1:0.3:0.06 (=mDBTBIm-II:PCCP:[Ir(Prn3tz1-mp)$_3$]). The thickness of the first light-emitting layer 1113a was 20 nm.

Next, on the first light-emitting layer 1113a, mDBTBIm-II (abbreviation) and [Ir(Prn3tz1-mp)$_3$] (abbreviation) were co-evaporated to form a second light-emitting layer 1113b. Here, the weight ratio of mDBTBIm-II (abbreviation) to [Ir(Prn3tz1-mp)$_3$] (abbreviation) was adjusted to 1:0.06 (=mDBTBIm-II:[Ir(Prn3tz1-mp)$_3$]). The thickness of the second light-emitting layer 1113b was set to 20 nm.

Note that [Ir(Prn3tz1-mp)$_3$] (abbreviation) is an organometallic complex of one embodiment of the present invention and is a guest material (dopant) in each of the first light-emitting layer 1113a and the second light-emitting layer 1113b.

Next, on the second light-emitting layer 1113b, a film of mDBTBIm-II (abbreviation) was formed to a thickness of 15 nm to form the first electron-transport layer 1114a.

After that, on the first electron-transport layer 1114a, a bathophenanthroline (abbreviation: BPhen) film was formed to a thickness of 20 nm, whereby the second electron-transport layer 1114b was formed.

Further, on the second electron-transport layer 1114b, a lithium fluoride (LiF) film was formed to a thickness of 1 nm by evaporation, whereby the electron-injection layer 1115 was formed.

Lastly, an aluminum film was formed to a thickness of 200 nm by evaporation as the second electrode 1103 functioning as a cathode. Thus, Light-emitting Element 2 of this example was fabricated.

Table 3 shows an element structure of Light-emitting Element 2 formed as described above.

TABLE 3

| | First Electrode | Hole-injection Layer | Hole-transport Layer | First Light-emitting Layer | Second Light-emitting Layer | First Electron-transport Layer | Second Electron-transport Layer | Electron-injection Layer | Second Electrode |
|---|---|---|---|---|---|---|---|---|---|
| Light-emitting Element 2 | ITSO 110 nm | CBP:MoOx (=4:2) 60 nm | BPAFLP 20 nm | mDBTBIm-II:PCCP: Ir(Prn3tz1-mp)$_3$ (=1:0.3:0.06) 20 nm | mDBTBIm-II: Ir(Prn3tz1-mp)$_3$ (=1:0.06) 20 nm | mDBTBIm-II 15 nm | BPhen 20 nm | LiF 1 nm | Al 200 nm |

Then, in a glove box containing a nitrogen atmosphere, Light-emitting Element 2 was sealed so as not to be exposed to the air (specifically, a sealant was applied onto an outer edge of the element and heat treatment was performed at 80° C. for 1 hour at the time of sealing). After that, operation characteristics of Light-emitting Element 2 were measured. Note that the measurement was carried out at room temperature (in an atmosphere kept at 25° C.).

Figure 29:
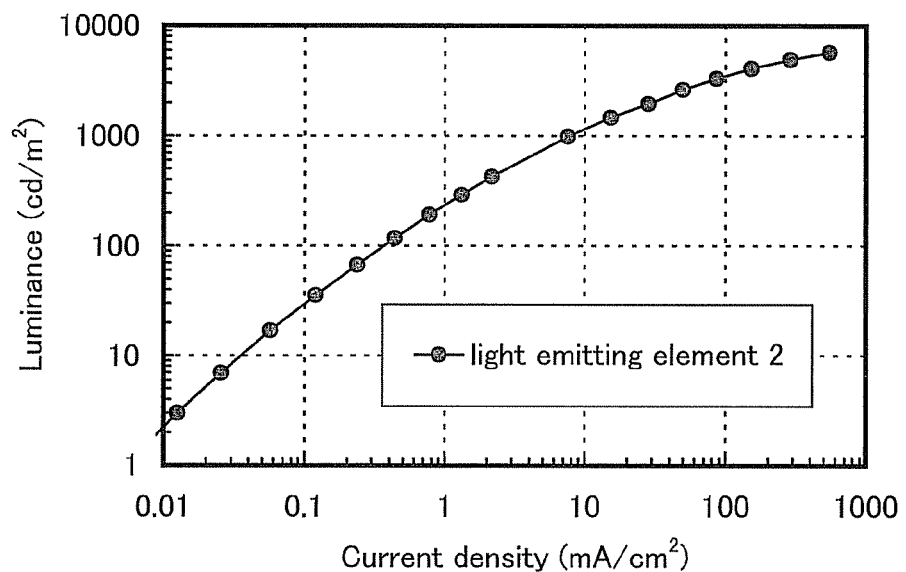
FIG. 29 shows current density vs. luminance characteristics of Light-emitting Element 2.
Figure 30:
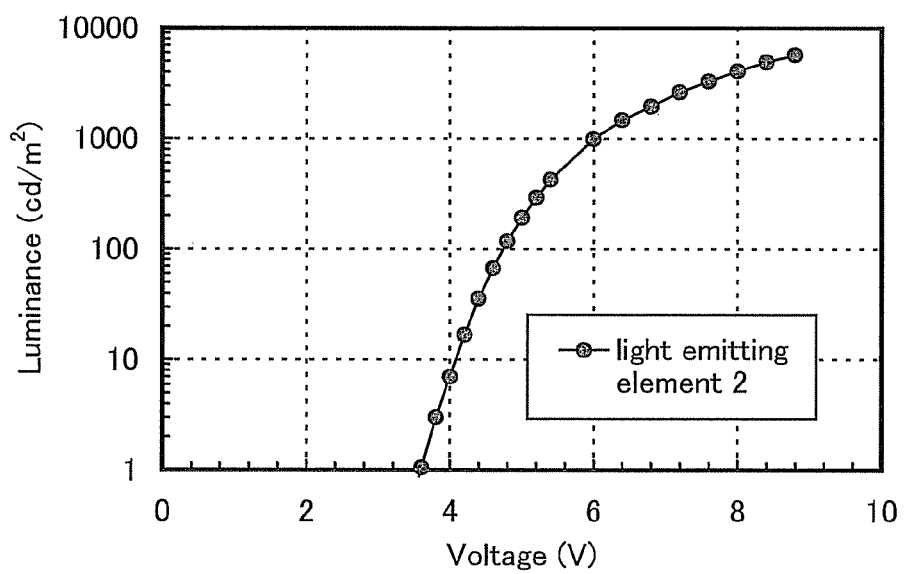
FIG. 30 shows voltage vs. luminance characteristics of Light-emitting Element 2.
Figure 31:
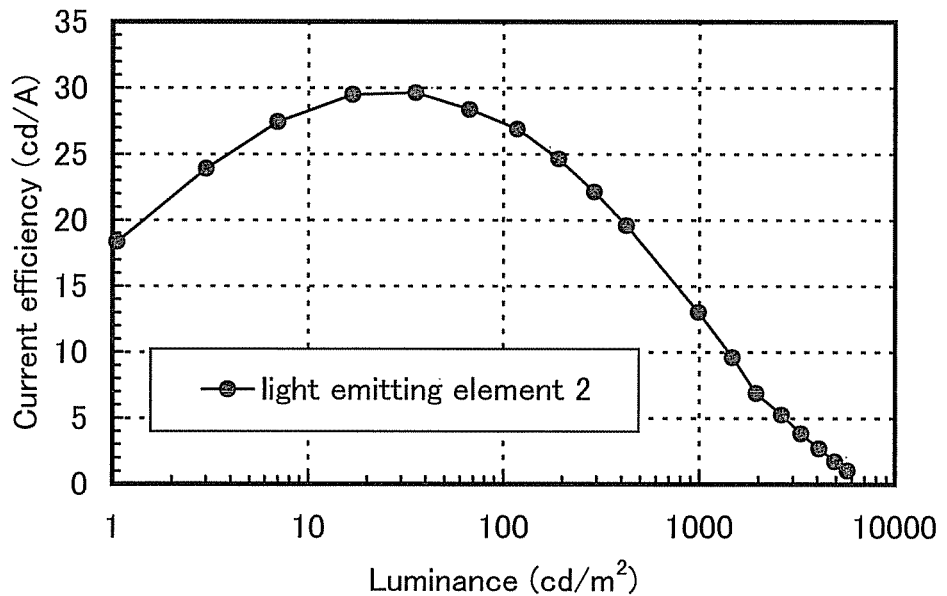
FIG. 31 shows luminance vs. current efficiency characteristics of Light-emitting Element 2.
Figure 32:
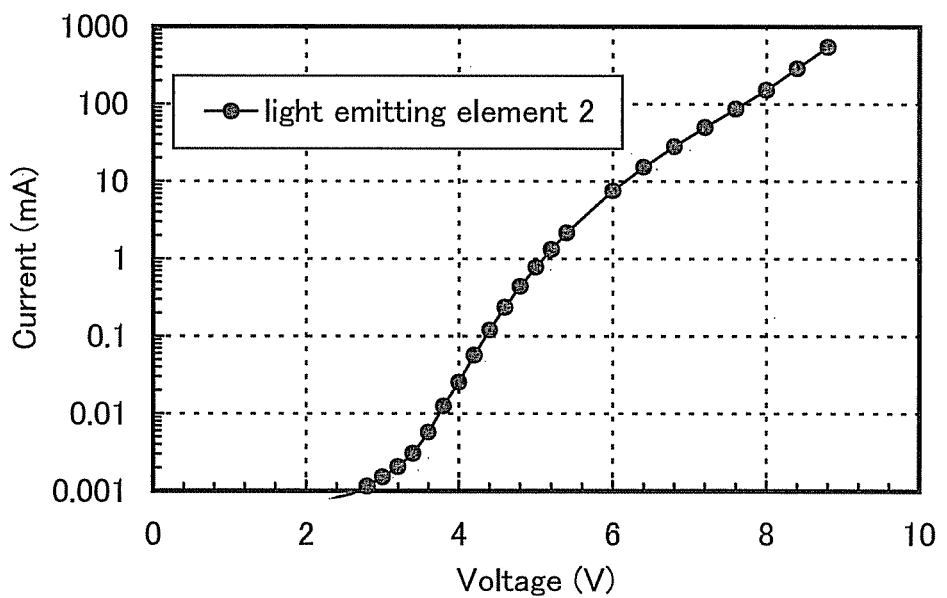
FIG. 32 shows voltage vs. current characteristics of Light-emitting Element 2.

FIG. 29 shows current density vs. luminance characteristics of Light-emitting Element 2. In FIG. 29, the horizontal axis represents current density (mA/cm$^2$) and the vertical axis represents luminance (cd/m$^2$). Further, FIG. 30 shows voltage vs. luminance characteristics of Light-emitting Element 2. In FIG. 30, the horizontal axis represents voltage (V) and the vertical axis represents luminance (cd/m$^2$). In addition, FIG. 31 shows luminance vs. current efficiency characteristics of Light-emitting Element 2. In FIG. 31, the horizontal axis represents luminance (cd/m$^2$) and the vertical axis represents current efficiency (cd/A). In addition, FIG. 32 shows voltage vs. current characteristics of Light-emitting Element 2. In FIG. 32, the horizontal axis represents voltage (V) and the vertical axis represents current (mA).

FIG. 29 and FIG. 31 show that Light-emitting Element 2 is a light-emitting element with high efficiency. Further, FIG. 29, FIG. 30, and FIG. 32 show that Light-emitting Element 2 is a light-emitting element with low drive voltage and low power consumption.

Next, Table 4 shows the voltage (V), current density (mA/cm$^2$), CIE, chromaticity coordinates (x, y), luminance (cd/m$^2$), current efficiency (cd/A), and external quantum efficiency (%) of Light-emitting Element 2 at a luminance of 989 cd/m$^2$.

TABLE 4

|  | Voltage (V) | Current Density (mA/cm$^2$) | CIE Chromaticity Coordinates x | CIE Chromaticity Coordinates y | Luminance (cd/m$^2$) | Current Efficiency (cd/A) | External Quantum Efficiency (%) |
|---|---|---|---|---|---|---|---|
| Light-emitting Element 2 | 6.0 | 7.6 | 0.36 | 0.61 | 989 | 13 | 3.9 |

Figure 33:
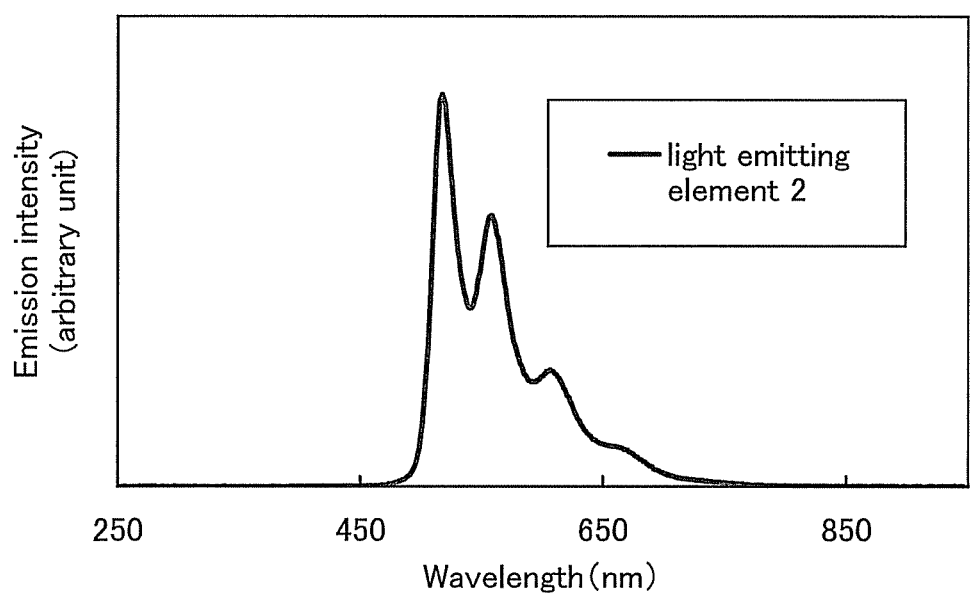
FIG. 33 shows an emission spectrum of Light-emitting Element 2.

FIG. 33 shows an emission spectrum when a current was supplied at a current density of 2.5 mA/cm$^2$ to Light-emitting Element 2. As shown in FIG. 33, the emission spectrum of Light-emitting Element 2 has peaks at 518 nm, 559 nm, and 607 nm.

In addition, as shown in Table 4, the CIE chromaticity coordinates of Light-emitting Element 2 were (x, y)=(0.36, 0.61) at a luminance of 989 cd/m$^2$. These results show that light originating from the dopant was obtained.

As described above, it was shown that Light-emitting Element 1 in which [Ir(Prn3tz1-mp)$_3$] (abbreviation) which is an organometallic complex of one embodiment of the present invention is used for the light-emitting layer can efficiently emit light in a wavelength band of blue-green. This indicates that [Ir(Prn3tz1-mp)$_3$] (abbreviation) can be favorably used as a guest material of a light-emitting material which emits light in a wavelength band of blue to yellow.

Next, reliability testing of Light-emitting Element 2 was carried out. Results of the reliability testing are shown in FIG. 34.

Figure 34:
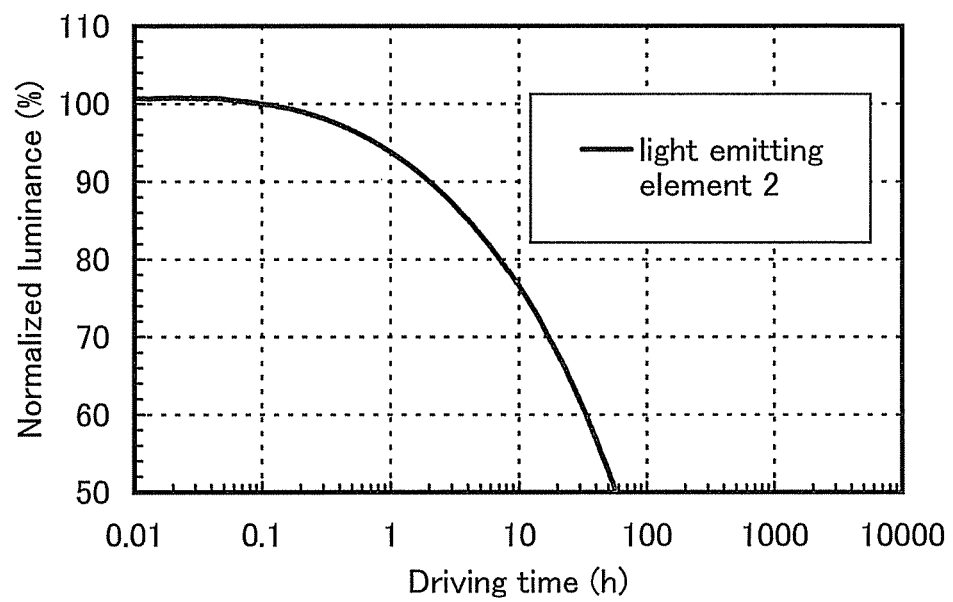
FIG. 34 shows driving time vs. normalized luminance characteristics of Light-emitting Element 2.

In FIG. 34, as the reliability testing, Light-emitting Element 2 was driven under the conditions where the initial luminance was set to 1000 cd/m$^2$ and the current density was constant. The horizontal axis represents driving time (h) of the element, and the vertical axis represents normalized luminance (%) on the assumption that the initial luminance is 100%. As shown in FIG. 34, it took about 57 hours of driving time for the normalized luminance of Light-emitting Element 2 to decline 50% or more.

FIG. 34 shows that Light-emitting Element 2 is a light-emitting element with a long lifetime.

The above results show that Light-emitting Element 2 in which [Ir(Prn3tz1-mp)$_3$] (abbreviation) which is a phosphorescent compound of one embodiment of the present invention is used for the light-emitting layer is a light-emitting element having high efficiency, low drive voltage, low power consumption, and a long lifetime.

Reference Example

The material used in Examples 8 and 9 will be described in this reference example.

Synthesis Example of mDBTBIm-II

A synthesis example of 2-[3-(dibenzothiophen-4-yl)phenyl]-1-phenyl-1H-benzimidazole (abbreviation: mDBTBIm-II), which was used as the material of Light-emitting Elements 1 and 2, is described.

Synthesis of 2-[3-(Dibenzothiophen-4-yl)phenyl]-1-phenyl-1H-benzimidazole (abbreviation: mDBT-BIm-II)

Into a 50-mL three-neck flask were put 1.2 g (3.3 mmol) of 2-(3-bromophenyl)-1-phenyl-1H-benzimidazole, 0.8 g (3.3 mmol) of dibenzothiophene-4-boronic acid, and 50 mg (0.2 mmol) of tri(ortho-tolyl)phosphine. The air in the flask was replaced with nitrogen. To this mixture were added 3.3 mL of a 2.0 mmol/L potassium carbonate aqueous solution, 12 mL of toluene, and 4 mL of ethanol. Under reduced pressure, the mixture was stirred to be degassed. Then, 7.4 mg (33 µmol) of palladium(II) acetate was added to this mixture, and the mixture was stirred at 80° C. for 6 hours under a nitrogen stream.

After a predetermined time elapsed, the aqueous layer of the obtained mixture was subjected to extraction with toluene. The obtained solution of the extract and the organic layer were combined, washed with saturated saline, and then dried with magnesium sulfate. This mixture was separated by gravity filtration, and the filtrate was concentrated to give an oily substance. This oily substance was purified by silica gel column chromatography. The silica gel column chromatography was carried out using toluene as a developing solvent. The obtained fraction was concentrated to give an oily substance. This oily substance was purified by high performance liquid chromatography. The high performance liquid chromatography was performed using chloroform as a developing solvent. The obtained fraction was concentrated to give an oily substance. This oily substance was recrystallized with a mixed solvent of toluene and hexane, so that the objective substance was obtained as 0.8 g of pale yellow powder in 51% yield. The synthesis scheme is shown in the following formula.

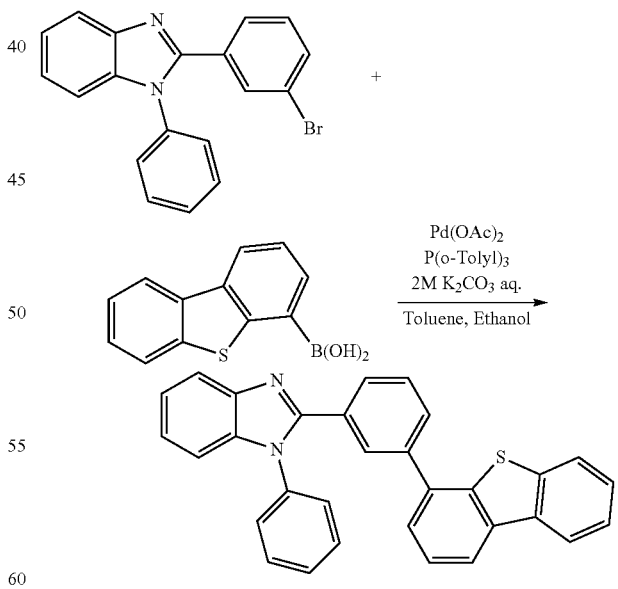

By a train sublimation method, 0.8 g of the obtained pale yellow powder was purified. In the sublimation purification, the pale yellow powder was heated at 215° C. under a pressure of 3.0 Pa with a flow rate of argon gas of 5 mL/min. After the sublimation purification, 0.6 g of white powder which was the objective substance was obtained in 82% yield.

A nuclear magnetic resonance (NMR) method identified this compound as 2-[3-(dibenzothiophen-4-yl)phenyl]-1-phenyl-1H-benzimidazole (abbreviation: mDBTBIm-II), which was the substance to be produced.

$^1$H NMR data of the obtained substance are as follows:

$^1$H NMR (CDCl$_3$, 300 MHz): δ (ppm)=7.23-7.60 (m, 13H), 7.71-7.82 (m, 3H), 7.90-7.92 (m, 2H), 8.10-8.17 (m, 2H)

This application is based on Japanese Patent Application serial no. 2011-125640 filed with Japan Patent Office on Jun. 3, 2011, the entire contents of which are hereby incorporated by reference.

What is claimed is:

1. An organometallic complex comprising a structure represented by General Formula (G1),

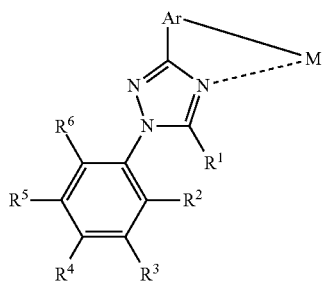

wherein:

Ar represents an arylene group comprising 6 to 13 carbon atoms,

R$^1$ represents an alkyl group comprising 1 to 4 carbon atoms,

R$^2$, R$^3$, R$^5$ and R$^6$ separately represent any of hydrogen, an alkyl group comprising 1 to 4 carbon atoms, and an unsubstituted phenyl group, R$^4$ represents any of hydrogen, a methyl group, an ethyl group, a propyl group, and an isopropyl group, M is a central metal and represents a Group 9 element, and wherein at least one of R$^2$, R$^3$, R$^5$, and R$^6$ represents the alkyl group comprising 1 to 4 carbon atoms or the unsubstituted phenyl group.

2. The organometallic complex according to claim 1, wherein the central metal M is iridium.

3. The organometallic complex according to claim 1, wherein the arylene group further comprises a substituent.

4. A light-emitting element comprising the organometallic complex according to claim 1 between a pair of electrodes.

5. A light-emitting device comprising the light-emitting element according to claim 4.

6. An electronic device comprising the light-emitting element according to claim 4.

7. A lighting device comprising the light-emitting element according to claim 4.

8. A light-emitting element comprising a light-emitting layer between a pair of electrodes,
wherein the light-emitting layer comprises the organometallic complex according to claim 1.

9. An organometallic complex represented by General Formula (G2),

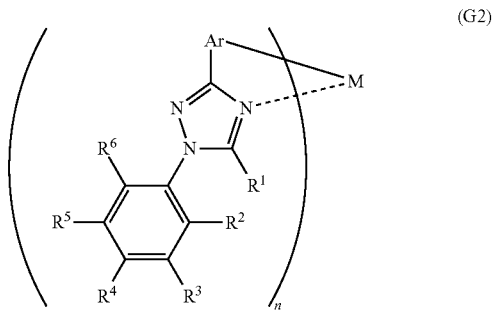

wherein:

Ar represents an arylene group comprising 6 to 13 carbon atoms,

R$^1$ represents an alkyl group comprising 1 to 4 carbon atoms,

R$^2$, R$^3$, R$^5$ and R$^6$ separately represent any of hydrogen, an alkyl group comprising 1 to 4 carbon atoms, and an unsubstituted phenyl group, R$^4$ represents any of hydrogen, a methyl group, an ethyl group, a propyl group, and an isopropyl group, M is a central metal and represents a Group 9 element or a Group 10 element, n=3 hen the central metal M is the Group 9 element, and n=2 when the central metal M is the Group 10 element, and wherein at least one of R$^2$, R$^3$, R$^5$, and R$^6$ represents the alkyl group comprising 1 to 4 carbon atoms or the unsubstituted phenyl group.

10. The organometallic complex according to claim 9, wherein the central metal M is iridium.

11. The organometallic complex according to claim 9, wherein the central metal M is platinum.

12. The organometallic complex according to claim 9, wherein the arylene group further comprises a substituent.

13. A light-emitting element comprising the organometallic complex according to claim 9 between a pair of electrodes.

14. A light-emitting device comprising the light-emitting element according to claim 13.

15. An electronic device comprising the light-emitting element according to claim 13.

16. A lighting device comprising the light-emitting element according to claim 13.

17. A light-emitting element comprising a light-emitting layer between a pair of electrodes,
wherein the light-emitting layer comprises the organometallic complex according to claim 9.

18. An organometallic complex represented by General Formula (G3),

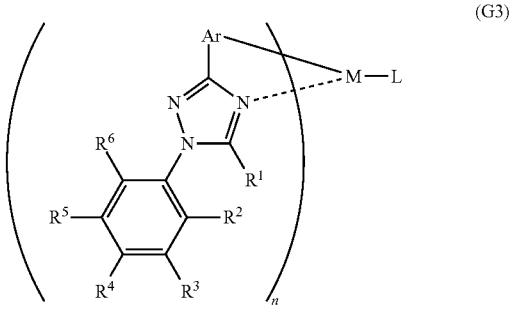

(G3)

wherein:

Ar represents an arylene group comprising 6 to 13 carbon atoms, $R^1$ represents an alkyl group comprising 1 to 4 carbon atoms, $R^2$, $R^3$, $R^5$ and $R^6$ separately represent any of hydrogen, an alkyl group comprising 1 to 4 carbon atoms, and an unsubstituted phenyl group, $R^4$ represents any of hydrogen, a methyl group, an ethyl group, a propyl group, and an isopropyl group, M is a central metal and represents a Group 9 element or a Group 10 element, n=2 when the central metal M is the Group 9 element, and n=1 when the central metal M is the Group 10 element, L represents a monoanionic bidentate ligand, and wherein at least one of $R^2$, $R^3$, $R^5$, and $R^6$ represents the alkyl group comprising 1 to 4 carbon atoms or the unsubstituted phenyl group.

19. The organometallic complex according to claim 18, wherein the central metal M is iridium.

20. The organometallic complex according to claim 18, wherein the central metal M is platinum.

21. The organometallic complex according to claim 18, wherein the arylene group further comprises a substituent.

22. A light-emitting element comprising the organometallic complex according to claim 18 between a pair of electrodes.

23. A light-emitting device comprising the light-emitting element according to claim 22.

24. An electronic device comprising the light-emitting element according to claim 22.

25. A lighting device comprising the light-emitting element according to claim claim 22.

26. A light-emitting element comprising a light-emitting layer between a pair of electrodes, wherein the light-emitting layer comprises the organometallic complex according to claim 18.

27. An organometallic complex comprising a structure represented by General Formula (G4),

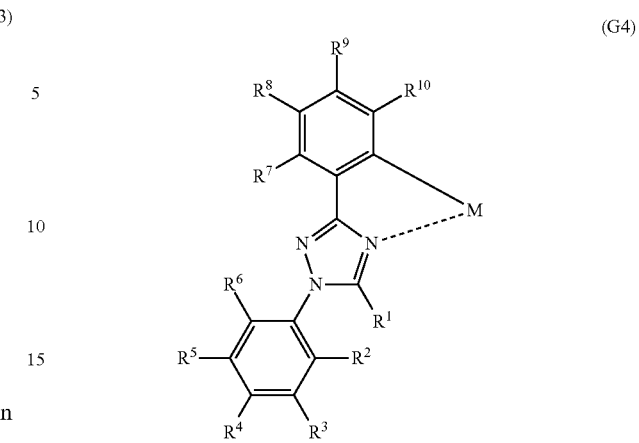

(G4)

wherein:

$R^1$ represents an alkyl group comprising 1 to 4 carbon atoms, $R^2$, $R^3$, $R^5$ and $R^6$ separately represent any of hydrogen, an alkyl group comprising 1 to 4 carbon atoms, and an unsubstituted phenyl group, $R^4$ represents any of hydrogen, a methyl group, an ethyl group, a propyl group, and an isopropyl group, $R^7$ to $R^{10}$ separately represent any of hydrogen, an alkyl group comprising 1 to 4 carbon atoms, an alkoxy group comprising 1 to 4 carbon atoms, an alkylthio group comprising 1 to 4 carbon atoms, a haloalkyl group comprising 1 to 4 carbon atoms, a halogen, and a phenyl group, M is a central metal and represents a Group 9 element or a Group 10 element, and wherein at least one of $R^2$, $R^3$, $R^5$, and $R^6$ represents the alkyl group comprising 1 to 4 carbon atoms or the unsubstituted phenyl group.

28. The organometallic complex according to claim 27, wherein the central metal M is iridium.

29. The organometallic complex according to claim 27, wherein the central metal M is platinum.

30. A light-emitting element comprising the organometallic complex according to claim 27 between a pair of electrodes.

31. A light-emitting device comprising the light-emitting element according to claim 30.

32. An electronic device comprising the light-emitting element according to claim 30.

33. A lighting device comprising the light-emitting element according to claim 30.

34. A light-emitting element comprising a light-emitting layer between a pair of electrodes, wherein the light-emitting layer comprises the organometallic complex according to claim 27.

35. An organometallic complex represented by General Formula (G5),

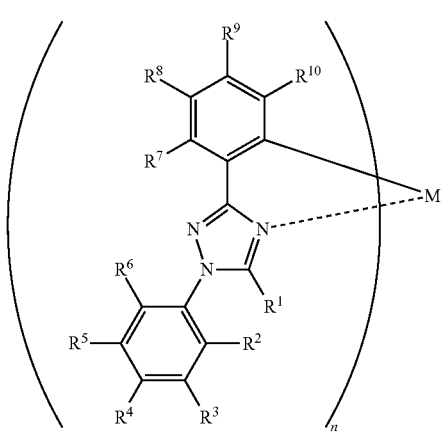

(G5)

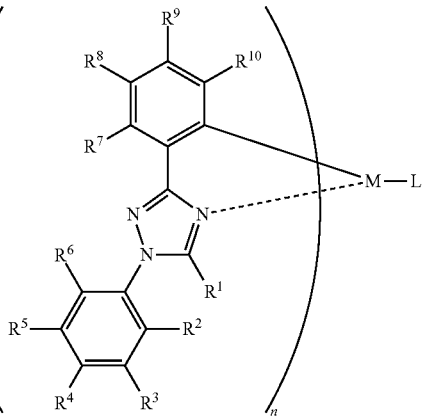

(G6)

wherein:
R¹ represents an alkyl group comprising 1 to 4 carbon atoms,
R², R³, R⁵ and R⁶ separately represent any of hydrogen, an alkyl group comprising 1 to 4 carbon atoms, and an unsubstituted phenyl group,
R⁴ represents any of hydrogen, a methyl group, an ethyl group, a propyl group, and an isopropyl group,
R⁷ to R¹⁰ separately represent any of hydrogen, an alkyl group comprising 1 to 4 carbon atoms, an alkoxy group comprising 1 to 4 carbon atoms, an alkylthio group comprising 1 to 4 carbon atoms, a haloalkyl group comprising 1 to 4 carbon atoms, a halogen, and a phenyl group,
M is a central metal and represents a Group 9 element or a Group 10 element,
n=3 when the central metal M is the Group 9 element, and n=2 when the central metal M is the Group 10 element, and
wherein at least one of R², R³, R⁵, and R⁶ represents the alkyl group comprising 1 to 4 carbon atoms or the unsubstituted phenyl group.

36. The organometallic complex according to claim 35, wherein the central metal M is iridium.

37. The organometallic complex according to claim 35, wherein the central metal M is platinum.

38. A light-emitting element comprising the organometallic complex according to claim 35 between a pair of electrodes.

39. A light-emitting device comprising the light-emitting element according to claim 38.

40. An electronic device comprising the light-emitting element according to claim 38.

41. A lighting device comprising the light-emitting element according to claim 38.

42. A light-emitting element comprising a light-emitting layer between a pair of electrodes,
wherein the light-emitting layer comprises the organometallic complex according to claim 35.

43. An organometallic complex represented by General Formula (G6), wherein:
R¹ represents an alkyl group comprising 1 to 4 carbon atoms,
R², R³, R⁵ and R⁶ separately represent any of hydrogen, an alkyl group comprising 1 to 4 carbon atoms, and an unsubstituted phenyl group,
R⁴ represents any of hydrogen, a methyl group, an ethyl group, a propyl group, and an isopropyl group,
R⁷ to R¹⁰ separately represent any of hydrogen, an alkyl group comprising 1 to 4 carbon atoms, an alkoxy group comprising 1 to 4 carbon atoms, an alkylthio group comprising 1 to 4 carbon atoms, a haloalkyl group comprising 1 to 4 carbon atoms, a halogen, and a phenyl group,
M is a central metal and represents a Group 9 element or a Group 10 element,
n=2 when the central metal M is the Group 9 element, and n=1 when the central metal M is the Group 10 element,
L represents a monoanionic bidentate ligand, and
wherein at least one of R², R³, R⁵, and R⁶ represents the alkyl group comprising 1 to 4 carbon atoms or the unsubstituted phenyl group.

44. The organometallic complex according to claim 43, wherein the central metal M is iridium.

45. The organometallic complex according to claim 43, wherein the central metal M is platinum.

46. A light-emitting element comprising the organometallic complex according to claim 43 between a pair of electrodes.

47. A light-emitting device comprising the light-emitting element according to claim 46.

48. An electronic device comprising the light-emitting element according to claim 46.

49. A lighting device comprising the light-emitting element according to claim 46.

50. A light-emitting element comprising a light-emitting layer between a pair of electrodes,
wherein the light-emitting layer comprises the organometallic complex according to claim 43.

51. An organometallic complex comprising:
a metal; and
a 1-phenyl-3-aryl-1H-1,2,4-triazole derivative,
wherein the metal is a Group 9 element,
wherein nitrogen at the 4-position of the 1-phenyl-3-aryl-1H-1,2,4-triazole derivative is coordinated to the metal,
wherein an aryl group at the 3-position of the 1-phenyl-3-aryl-1H-1,2,4-triazole derivative is bonded to the metal, wherein a p-position of the 1-phenyl of the 1-phenyl-3-aryl-1H-1,2,4-triazole derivative is substituted by a methyl group, an ethyl group, a propyl group, or an isopropyl group or unsubstituted, wherein a 5-position of the triazole of the 1-phenyl-3-aryl-1H-1,2,4-triazole derivative is substituted by an alkyl group comprising 1 to 4 carbon atoms, and wherein at least one of 2-position, 3-position, 5-position, and 6-position of the 1-phenyl of the 1-phenyl-3-aryl-1H-1,2,4-triazole derivative is substituted by an alkyl group comprising 1 to 4 carbon atoms or an unsubstituted phenyl group.

52. A light-emitting element comprising an organometallic complex between a pair of electrodes, the organometallic complex comprising:

a metal; and a 1-phenyl-3-aryl-1H-1,2,4-triazole derivative, wherein the metal is a Group 9 element, wherein nitrogen at the 4-position of the 1-phenyl-3-aryl-1H-1,2,4-triazole derivative is coordinated to the metal, wherein an aryl group at the 3-position of the 1-phenyl-3-aryl-1H-1,2,4-triazole derivative is bonded to the metal, wherein a p-position of the 1-phenyl of the 1-phenyl-3-aryl-1H-1,2,4-triazole derivative is substituted by a methyl group, an ethyl group, a propyl group, or an isopropyl group or unsubstituted, wherein a 5-position of the triazole of the 1-phenyl-3-aryl-1H-1,2,4-triazole derivative is substituted by an alkyl group comprising 1 to 4 carbon atoms, and wherein at least one of 2-position, 3-position, 5-position, and 6-position of the 1-phenyl of the 1-phenyl-3-aryl-1H-1,2,4-triazole derivative is substituted by an alkyl group comprising 1 to 4 carbon atoms or an unsubstituted phenyl group.

\* \* \* \* \*